United States Patent [19]

Russell

[11] Patent Number: 5,294,621
[45] Date of Patent: Mar. 15, 1994

[54] THIENO TETRAHYDROPYRIDINES USEFUL AS CLASS III ANTIARRHYTHMIC AGENTS

[75] Inventor: Ronald K. Russell, Titusville, N.J.

[73] Assignee: Ortho Pharmaceutical Corporation, Raritan, N.J.

[21] Appl. No.: 958,197

[22] Filed: Oct. 7, 1992

[51] Int. Cl.⁵ ............... A61K 31/435; C07D 495/04
[52] U.S. Cl. .................................. 514/301; 546/114
[58] Field of Search ........................ 546/114; 514/301

[56] References Cited

U.S. PATENT DOCUMENTS 4,051,141 9/1977 Castaigne ........................ 546/114
4,075,340 2/1978 Maffrand ........................ 514/301
4,681,888 7/1987 Esanu ............................. 546/114

Primary Examiner—Bernard Dentz
Attorney, Agent, or Firm—Joseph J. Brindisi

[57] ABSTRACT

This invention relates to thieno tetrahydropyridine and isoquinoline derivative compounds which are useful as antiarrhythmic agents, pharmaceutical compositions comprising such compounds, novel intermediates for their preparation and their methods of use. More particularly these thieno tetrahydropyridine and isoquinoline derivative compounds have been demonstrated to increase the effective refractory period (ERP) of isolated perfused cardiac tissue in vitro.

17 Claims, No Drawings

THIENO TETRAHYDROPYRIDINES USEFUL AS CLASS III ANTIARRHYTHMIC AGENTS

FIELD OF THE INVENTION

This invention relates to thieno tetrahydropyridine and isoquinoline derived compounds which are useful as antiarrhythmic agents, novel intermediates for their preparation and their methods of use. More particularly these thieno tetrahydropyridine and isoquinoline derived compounds have been demonstrated to increase the effective refractory period (ERP) of isolated superfused cardiac tissue in vitro which makes these compounds useful as antiarrhythmic agents.

BACKGROUND OF THE INVENTION

It has been estimated that in persons between the ages of 35 and 64 years of age, nearly 1 death in three is due to coronary heart disease Gordon, T.; Kannel, W. B. *J. Amer. Med. Assoc.*, 1971, 215,1617] and there are approximately 400,000 sudden cardiac deaths annually in the United States alone [Green, H. L.; et al, *Amer. J. Cardiology*, 1989, 63, 1]. Over the last few years, development of drugs to treat cardiac arrhythmias (sudden cardiac death) has received much attention [Steinberg, M. I.; Lacefield, W. B.; Robertson, D. W. Class I and III Antiarrhythmic Drugs. In *Ann. Reports in Med. Chem.*, Bailey, D. M., Ed.; Academic Press, Inc.: Orlando, 1986; 21, pp 95–108; Arrowsmith, J. E.; Cross, P. E. Antiarrhythmic Agents. In *Ann. Reports in Med. Chem.*, Bristol, J. A., Ed.; Academic Press, Inc.: San Diego, 1990; 25, pp 79–88]. A classification of these drugs has been presented by Vaughan Williams [Vaughan Williams, E. M. *J. Clin. Pharmacol.*, 1984, 24, 129] which is based on their electrophysiological effects on cardiac tissue.

Class I agents and subclasses (Ia, Ib, Ic) are defined as antiarrhythmic agents which have inhibitory effects on the sodium channel which result in a reduction of conduction velocity in the cardiac tissue. The Class I agents are currently the most widely used for antiarrhythmic therapy. Recent results of the Cardiac Arrhythmia Suppression Trial (CAST), [*N. Engl. J. Med.*, 1989, 321, 4061], have raised concerns about the Class IC subtype (e.g. flecainide) and suggest that antiarrhythmic drugs having other mechanisms of action should be considered.

Specific Class III antiarrhythmic drugs (e.g. d-sotalol) do not affect cardiac sodium channels or conduction velocity. These agents selectively prolong the cardiac action potential duration and thereby increase the effective refractory period (ERP). Prolongation of refractoriness is an effective means of preventing or terminating atrial and ventricular arrhythmias, the latter of which can be life threatening.

The discovery and development of new Class III antiarrhythmic agents which may be effective for the prevention of sudden cardiac death is desirable and is an object of the present invention.

It is therefore an object of the invention to provide novel compounds which are useful as antiarrhythmic agents. Additional objects and advantages of the invention will be set forth, in part, in the description which follows and in part will be obvious from this description, or may be learned by practice of the invention. The objects and advantages of the invention are realized and obtained by means of the methods, and the combinations particularly pointed out in the appended claims.

SUMMARY OF THE INVENTION

To achieve the object in accordance with the purposes of the invention, as embodied and fully described herein, the invention comprises novel compounds which are ring-fused tetrahydropyridine derivatives of the

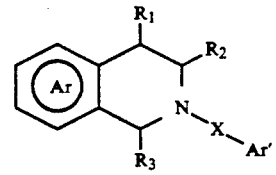

where
Ar may be heterocyclic (e.g. pyridine, thiophene, furan, pyrrole, etc), substituted heterocyclic or

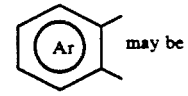  may be

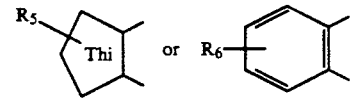

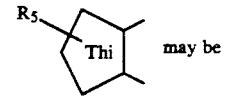  may be

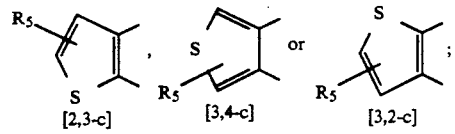

$R_1$ may be hydrogen or $C_1$–$C_3$ alkyl, preferably, hydrogen or methyl;

$R_2$ May be hydrogen, $C_1$–$C_6$ alkyl, $C_3$–$C_7$ or branched chain alkyl, preferably, hydrogen or $C_1$–$C_4$ alkyl;

$R_3$ may be hydrogen, $C_1$–$C_6$ alkyl, $C_3$–$C_7$ branched chain alkyl, thiophene, aryl or substituted aryl wherein the aryl substituents are $C_1$–$C_6$ alkyl or $C_1$–$C_6$ alkoxy (e.g., phenyl, or substituted phenyl); preferably, hydrogen, $C_1$–$C_6$ alkyl, branched propyl, phenyl, thiophene or 4-methoxy-phenyl;

$R_4$ may be hydrogen, $C_1$–$C_5$ alkyl, $C_3$–$C_7$ branched chain alkyl, halogen, $C_1$–$C_3$ alkoxy, nitro, amino, imidazole, cyano, $CO_2R_1$, $SO_2R_1$, $CF_3$, $NHCOR_8$, $NR_7SO_2R_8$, $CH_2SO_2R_1$, $CH_2PO(OR_1)_2$ or $CH_2$-imidazo, preferably, hydrogen, chloro, fluoro, methyl, methoxy, nitro, amino, cyano, $NHCOCH_3$, $NHSO_2CH_3$ or $CO_2CH_3$;

X may be $CH_2$, $(CH_2)_n$, $(CH_2)_nO$, $(CH_2)_mNR_7CO$, $(CH_2)_mNR_7SO_2$, $(CH_2)_mNHCH_2$,

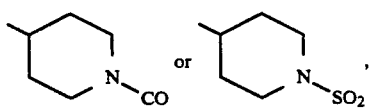

preferably, $(CH_2)_n$, $(CH_2)_2O$, $(CH_2)_mNR_7CO$, $(CH_2)_mNR_7SO_2$ or $(CH_2)_mNHCH_2$;

$R_5$ may be hydrogen, halogen or nitro;

$R_6$ may be hydrogen, $C_1$-$C_4$ alkyl, $C_3$-$C_6$ branched chain alkyl, halogen, $C_1$-$C_3$ alkoxy, preferably, hydrogen or methoxy; $R_7$ may be hydrogen or $C_1$-$C_3$ alkyl, preferably, hydrogen, methyl or ethyl;

$R_8$ may be hydrogen, $CF_3$, $C_1$-$C_4$ alkyl, $C_3$-$C_5$ branched chain alkyl, aryl or substituted aryl (preferably, phenyl or substituted phenyl) wherein the aryl substituents are halogen, $C_1$-$C_6$ alkyl or $C_1$-$C_6$ alkoxy;

n may be 2–5, preferably 2–4; and m may be 2–4, preferably 2 or 3.

When $R_1$ is alkyl then $R_2$ is hydrogen and when $R_1/R_3$ or $R_2/R_3$ are both alkyl, then diastereoisomers are possible such that $R_1/R_3$ may be cis or trans and $R_2/R_3$ may be cis or trans:

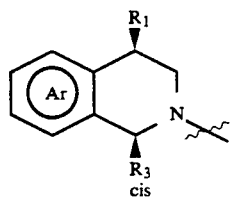

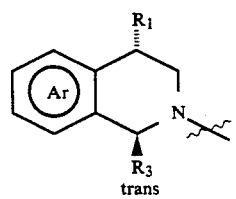

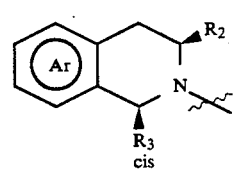

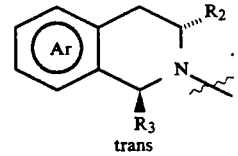

The compounds of the above formula are useful as agents which increase the effective refactory period (ERP) and may serve as agents for the prevention of sudden cardiac death.

As embodied and fully described herein, the invention further comprises a method of increasing the ERP in a patient and reducing the incidents of sudden cardiac death comprising the step of administering an ERP increasing effective amount of a ring-fused tetrahydropyridine derivative as described above to a patient in danger of suffering sudden As embodied and fully described herein, the invention further comprises novel intermediate compounds which are useful for preparing the thieno tetrahydropyridine derivatives described above. These novel intermediate compounds have the formula:

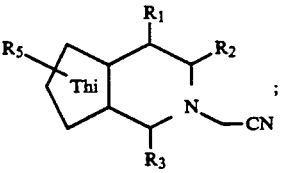

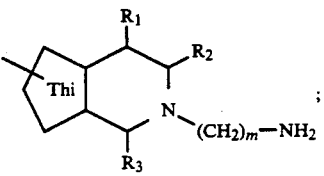

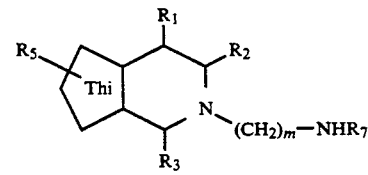

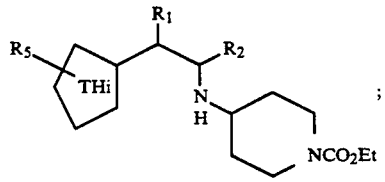

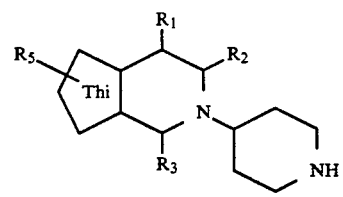

wherein 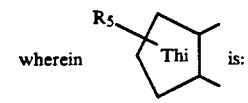 is:

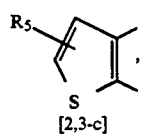

[2,3-c]

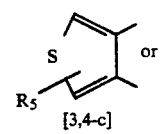

[3,4-c]

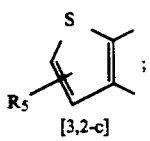

[3,2-c]

$R_1$ is hydrogen and $C_1$-$C_3$ alkyl;

$R_2$ is hydrogen, $C_1$-$C_6$ alkyl, $C_3$-$C_7$ or branched chain alkyl;

$R_3$ is hydrogen, $C_1$-$C_6$ alkyl, $C_3$-$C_7$ branched chain alkyl, thiophene, aryl or substituted aryl (preferably, phenyl or substituted phenyl) wherein the aryl substituents are $C_1$-$C_6$ alkyl or $C_1$-$C_6$ alkoxy;

$R_5$ is hydrogen, halogen or nitro;

$R_7$ is hydrogen or $C_1$-$C_3$ alkyl; and m is 2–4; and when $R_1$ is alkyl and $R_2$ is hydrogen and when $R_1/R_3$ or $R_2/R_3$ are both alkyl, then diastereoisomers are possible such that $R_1/R_3$ is cis or trans and $R_2/R_3$ is cis or trans:

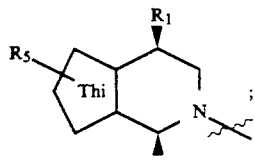
cis

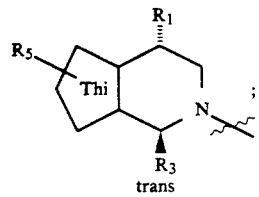
trans

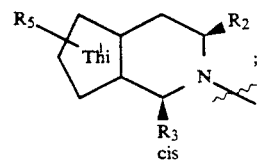
cis

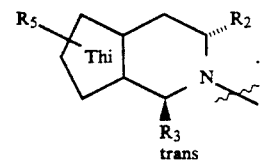
trans

It is to be understood that both the foregoing general and the following detailed description are exemplary and explanatory only and are not intended to be restrictive of the invention as claimed.

DETAILED DESCRIPTION OF THE PREFERRED EMBODIMENTS OF THE INVENTION

Reference will now be made in detail to present preferred embodiments of the invention, examples of which are illustrated in the following examples section.

In accordance with the invention novel compounds, compositions and methods are provided to achieve the objects in accordance with the purposes of the invention, as embodied and fully described herein. The invention provides novel ring-fused tetrahydropyridine derivatives, i.e. thieno tetrahydropyridines and isoquinoline derivatives of the above formula that increase the effective refactory period (ERP) of isolated perfused cardiac tissue in vitro.

Compounds of the above formula can be prepared according to the reaction Schemes identified below:

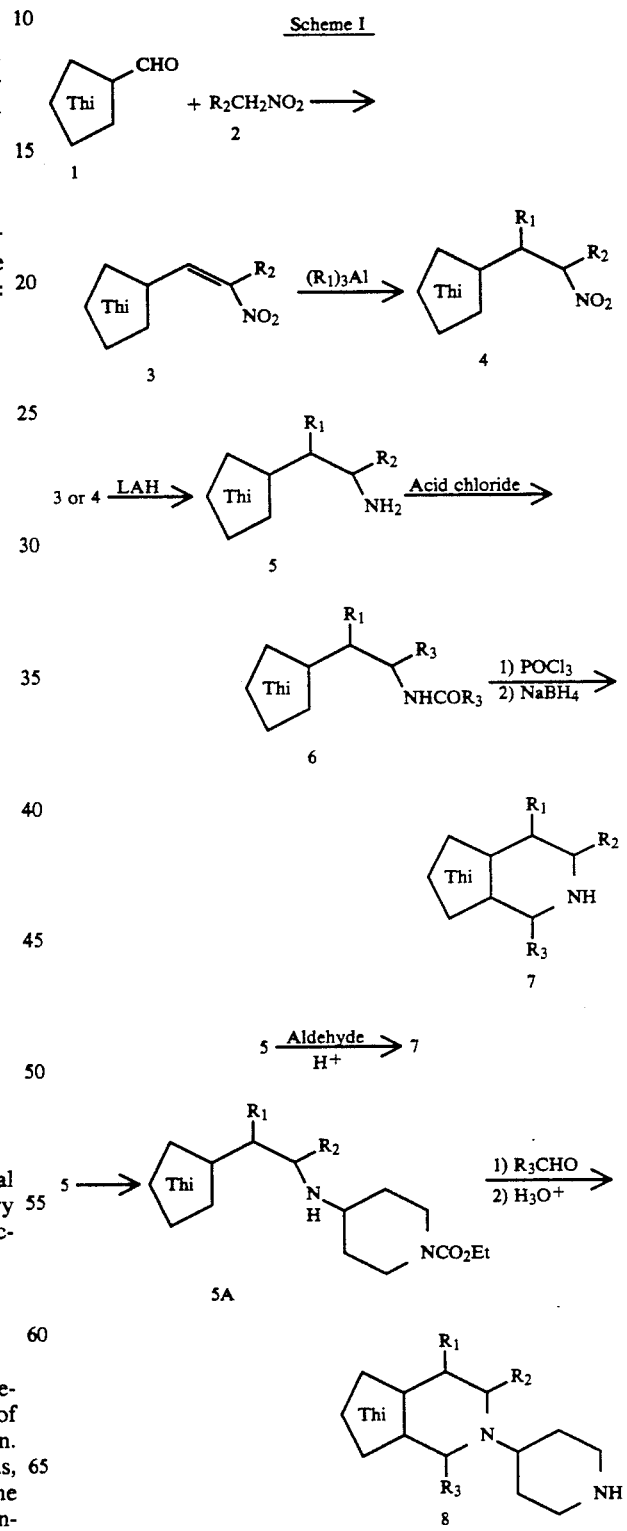

-continued
Scheme I
7 → 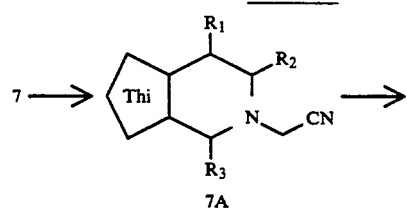 →
7A
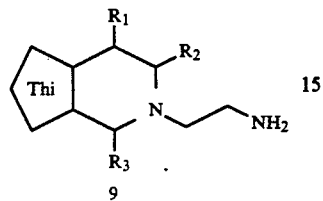
9
7 For m > 2 → 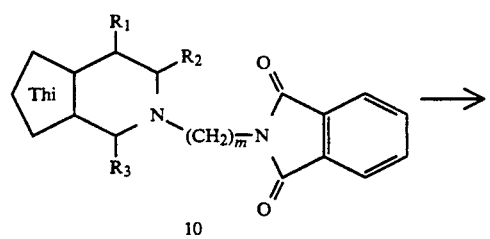
10
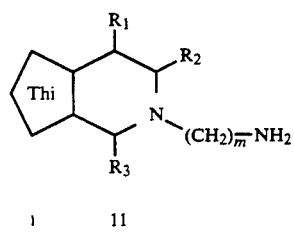
11
9 or 11 For R₇ ≠ H → 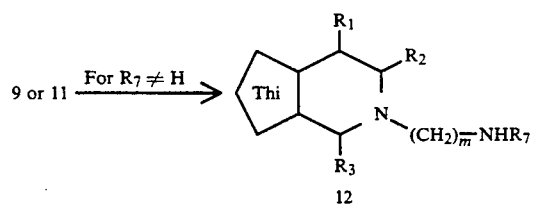
12
7 → 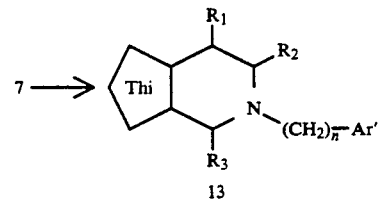
13
7 → 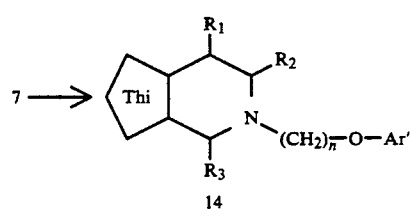
14
-continued
Scheme I
12 → 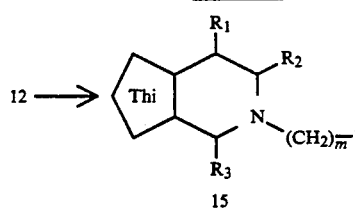
15
12 → 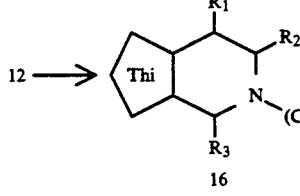
16
12 → 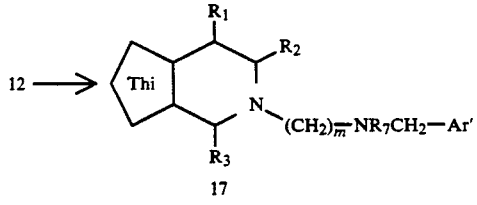
17
8 → 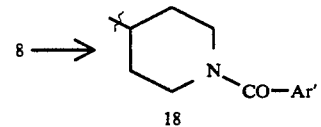
18
8 → 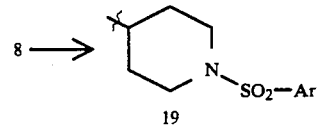
19
When Ar' is 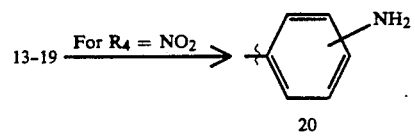
13-19 For R₄ = NO₂ → 
20
20 → 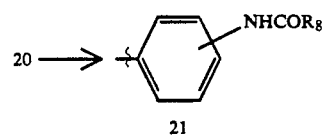
21
20 → 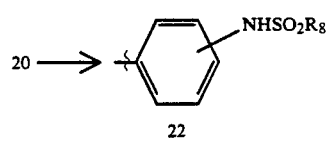
22

-continued
Scheme I

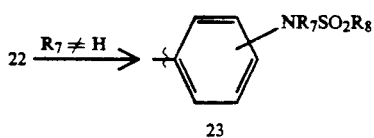

Scheme II

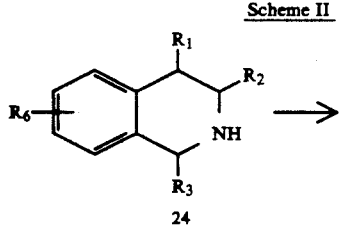

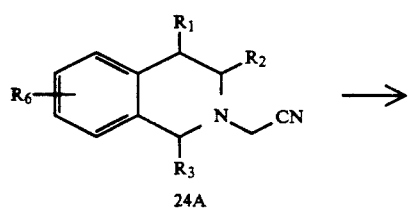

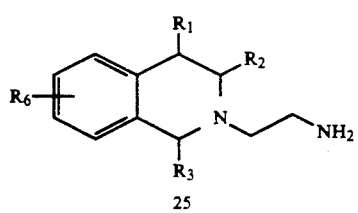

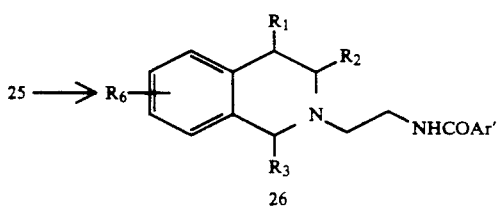

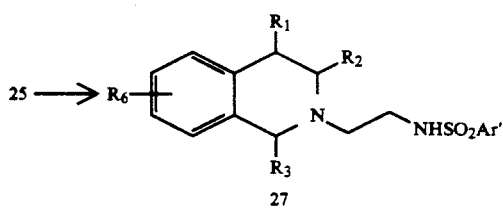

When Ar' is

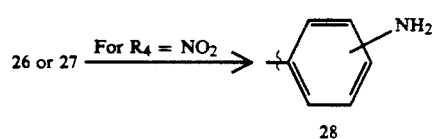

-continued
Scheme II

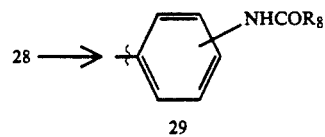

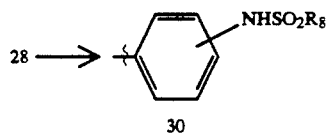

The synthesis outlined above in Scheme I begins with the Henry reaction between the commercially available thiophene-2-carboxaldehyde, thiophene-3-carboxaldehyde or 2-chlorothiophene-3-carboxaldehyde [Campaigne, E.; LeSuer, W. M. *J. Amer. Chem. Soc.*, 1949, 71, 333], a suitable nitroalkane 2 such as nitromethane, nitroethane, nitrobutane or nitrohexane and with a suitable catalyst such as methylamine hydrochloride/sodium acetate/acetic acid or benzylamine/acetic acid present whereby the mixture may be warmed to 55°–60° C. for 6 to 16 hours. This nitroalkene 3 is reacted with a commercially available trialkylaluminum such as trimethylaluminum, triethylaluminum or tripropylaluminum in an inert solvent such as hexane or toluene under nitrogen at 5°–25° C. to provide nitroalkene 4. The nitro compounds 3 or 4 are then reduced with lithium aluminum hydride in an inert solvent such as ether, tetrahydrofuran or dioxane under nitrogen to provide the aminoethylthiophene 5. The aminoethylthiophenes 5 are reacted with a suitable acid chloride such as acetyl chloride, propionyl chloride, hexanoyl chloride, isobutyryl chloride, benzoyl chloride, anisoyl chloride, 4-chlorobenzoyl chloride or 2-thiophenecarbonyl chloride in an inert solvent such as ether, methylene chloride, chloroform or toluene and with an HCl scavenger such as triethylamine, pyridine or sodium bicarbonate and a catalyst such as 4-dimethylaminopyridine present to produce the amides 6.

These amides 6 are cyclized to the tetrahydropyridines 7 by the Bischler-Napieralski reaction using phosphorous oxychloride either neat or in an inert solvent such as benzene or toluene present and at room temperature (rt) to 120° C. for 2-24 hours. The resulting intermediate dihydropyridine compounds are reduced to 7 with a suitable reducing agent such as sodium borohydride in an inert solvent such as methanol or ethanol in a pH range of 2-4 at 0° C. to rt for 4-24 hours. An alternative synthesis of 7 can be accomplished by the Pictet-Spengler reaction where the amine 5 is reacted with a carboxaldehyde such as formaldehyde, benzaldehyde or a substituted benzaldehyde an inert solvent such as water, methanol or ethanol and a suitable mineral acid such as hydrochloric acid. If the mineral acid is left out, an intermediate triazine is isolated. This material is then reacted with a mineral acid such as hydrochloric acid in an inert solvent such as ethanol or 2-propanol to afford the tetrahydropyridine compound 7. A third alternative synthesis of the tetrahydropyridine ring is accomplished by reacting 5 with a suitable ketone such as 1-carboethoxy-4-piperidone with a mild reducing agent such as sodium cyanoborohydride in an inert solvent such as methanol or ethanol at rt for 2-6 hours. This intermediate N-alkylated material is reacted with a suitable aldehyde such as formaldehyde in glacial acetic acid at 40°-60° C. The material 5A is reacted with a suitable mineral acid such as hydrochloric acid in an inert solvent such as glacial acetic acid at 100°-120° C. for 20-24 hours to produce the amino compound 8.

The amines 7 are reacted with an excess of either chloroacetonitrile or bromoacetonitrile in an inert solvent such as acetonitrile, 2-propanol, acetone or tetrahydrofuran in the presence of a base such as triethylamine, pyridine, sodium bicarbonate or sodium carbonate to afford the cyanomethyl intermediates 7A. These intermediates are reduced with lithium aluminum hydride in an inert solvent such as ether, tetrahydrofuran or dioxane at rt to 60° C. for 2-20 hours to afford the primary amines 9. To produce longer chain compounds 11 (m>2), the amine 7 is reacted with an appropriate phthalimide such as N-(3-bromopropyl)phthalimide or N-(4-bromobutyl)phthalimide and with a suitable base such as sodium bicarbonate in an inert solvent such as dimethylformamide at 50°-90° C. for 18-24 hours. The phthalimides 10 are reacted with hydrazine hydrate in a suitable solvent such as methanol or ethanol at 50°-80° C. for 18-24 hours to afford 11.

The secondary amines 12 are prepared by reductive amination methods using an alkyl carboxaldehyde or ketone such as formaldehyde or acetone and a reducing agent such as sodium cyanoborohydride in an inert solvent such as methanol or ethanol at rt for 12 to 24 hours under an inert atmosphere such as nitrogen. Alternatively, the amines 9 or 11 are reacted with either a chloroformate or an acid chloride in a suitable solvent such as methylene chloride and these intermediate urethanes or amides are reduced with a suitable reagent such as lithium aluminum hydride in an inert solvent such as tetrahydrofuran at 50°-75° C.

The amines 7 are treated with a suitable 4-nitrophenyl alkyl p-toluenesulfonate (or methanesultonate) or 4-nitrophenyl alkyl halide such as 4-nitrophenethyl p-toluenesulfonate, 4-(4-nitrophenyl)-1-butyl p-toluenesulfonate, 4-(4-nitrophenyl)-1-butyl methanesulfonate, 4-nitrophenethyl bromide or 4-(4-nitrophenyl)-1-butyl bromide in an inert solvent such as acetonitrile, acetone, 2-butanone or tetrahydroturan in the presence of a catalyst such as sodium iodide or potassium iodide and a base such as triethylamine, pyridine, sodium bicarbonate or sodium carbonate to produce the nitrophenyl compounds 13 (Ar'=4-nitrophenyl). The amines 7 are also reacted with P-toluenesulfonylalkyl (or methanesulfonylalkyl) or haloalkyl 4-nitrophenylethers such as 2-(4-nitrophenoxy)ether p-toluenesulfonate, p-bromo-4-nitrophenetole or 3-chloropropyl-4-nitrophenyl ether in an inert solvent such as acetonitrile, acetone, 2-butanone or tetrahydrofuran at 50°-100° C. in the presence of a catalyst such as sodium iodide or potassium iodide and a base such as triethylamine, pyridine, sodium bicarbonate or sodium carbonate to afford the phenyl ether compounds 14 (Ar'=4-nitrophenyl).

The amines 12 are treated with appropriate acid halide [commercially available (e.g. Aldrich Chemical Company, Inc.) or prepared from the corresponding carboxylic acids (mixed anhydride method or thionyl chloride method)] such as benzoyl chloride, 2-, 3- or 4-nitrobenzoyl chloride, 2-, 3- or 4-chlorobenzoyl chloride, 2-, 3- or 4-fluorobenzoyl chloride, o-, m- or p-anisoyl chloride, p-toluoyl chloride, 4-trifluoromethylbenzoyl chloride, 4-cyanobenzoyl chloride, 4-carbomethoxybenzoyl chloride, 4-carboxy-N,N-diethylbenzenesulfonamide, 4-(methylsulfonyl)benzoic acid, 2,4-difluorobenzoyl chloride, 3,4-dichlorobenzoyl chloride, 2,3,4,5,6-pentafluorobenzoyl chloride, picolinoyl chloride, nicotinoyl chloride, isonicotinoyl chloride, 2-thiophenecarbonyl chloride or 5-nitro-2-thiophenecarbonyl chloride in an inert solvent such as methylene chloride, chloroform, ether or toluene either with or without the presence of a catalytic amount of 4-dimethylaminopyridine and an HCl scavenger such as triethylamine, pyridine or sodium bicarbonate to produce the amides 15.

Alternatively, the amines 12 are reacted with trimethylaluminum in an inert solvent such as benzene, toluene or hexane under an inert atmosphere such as nitrogen and then treated with the appropriate methyl or ethyl benzoates such as methyl 4-(aminosulfonyl)benzoate, methyl 4-[(imidazol-1-yl)methyl]benzoate, diethyl (4-methoxycarbonylphenyl)methyl phosphonate, methyl 4-(methanesulfonylmethyl)benzoate or ethyl 4-(imidazol-1-yl)benzoate at 50°-60° C. for 16-24 hours.

Similar to the preparation of 15,12 is treated with 2- or 4-nitrobenzenesulfonyl chloride or 2-chlorobenzenesulfonyl chloride to produce the sulfonamides 16.

The amines 12 are reacted with benzyl halides, e.g. 4-nitrobenzyl chloride, a base such as sodium bicarbonate and sodium iodide in an inert solvent such as 2-propanol at reflux to afford 17. Alternatively, the amides 15 are reduced to the benzyl amines 17 with a suitable hydride reducing agent such as diborane in an inert solvent such as tetrahydrofuran at 60°-80° C. for 12-24 hours under an inert atmosphere such as nitrogen.

The cyclic amine 8 is converted to its carboxamide 18 as described above for the conversion of 12 to 15 and 8 is converted to the sulfonamide 19 as described for the conversion of 12 to 16. The phenyl nitro compounds 13-19 are converted to the aminobenzenes 20 by any number of reducing methods such as iron in acetic acid, iron in dimethylformamide, ammonium formate with palladium black (or palladium on carbon), formic acid with palladium black (or palladium on carbon), nickel (II) chloride/sodium borohydride or palladium on carbon under a hydrogen atmosphere. These aminobenzenes are then converted to their corresponding amides 21 using a suitable acid chloride such as acetyl chloride, propionyl chloride, hexanoyl chloride, isobutyryl chloride, trimethylacetyl chloride, trifluroacetyl chloride or benzoyl chloride in an inert solvent such as methylene chloride, chloroform or toluene either in the presence or absence of an HCl scavenger such as triethylamine, pyridine or sodium bicarbonate.

In a fashion similar to that described for the conversion of 12 to sulfonamides 16, the sulfonamides 22 are prepared using the necessary sulfonyl chlorides such as methanesulfonyl chloride, chloromethylsulfonyl chloride, ethanesulfonyl chloride, butanesulfonyl chloride, benzenesulfonyl chloride or 4-chlorobenzenesulfonyl chloride. These sulfonamides are reacted with a strong base such as sodium hydride in an inert solvent such as dimethylformamide or tetrahydrofuran and then treated with an alkylating agent such a methyl iodide at 0° C. to rt for 12-24 hours under an inert atmosphere to afford 23.

The preparation of the isoquinoline series is shown in Scheme II. This synthesis begins with the commercially available isoquinolines 24 or with isoquinolines that are prepared by the series of steps shown in Scheme I to convert 5 to 7 starting from commercially available phenethylamines such as 3-methoxyphenethylamine. The isoquinoline 24 is converted to the aminoethyl compound 25 in the same fashion as described for the conversion of 7 to 9 in Scheme 1. This material is then converted to the carboxamides 26 and sulfonamides 27 in the same fashion as 12 was converted to 15 and 16, respectively. Reduction of 26 (or 27) when $R_4=NO_2$ is accomplished by the same procedure as described for the conversion of 13-19 to 20 in Scheme 1. These aminobenzenes are converted to their corresponding amides 29 or sulfonamides 30 using the same procedures as described above for the conversion of 20 to 21 or 22, respectively.

The invention will now be illustrated by examples. The examples are not intended to be limiting of the scope of the present invention. In conjunction with the detailed and general description above, the examples provide further understanding of the present invention and outline a process for producing the compounds of the invention.

The following examples represent preferred embodiments of the compounds, compositions, processes and methods of the invention for satisfying the stated objects of the invention.

EXAMPLES

The following processes and procedures for preparing the compounds of the present invention correspond to those reaction schemes illustrated above. The procedures below describe with particularity the various chemical reactions and procedures utilized. Any methods, starting materials or reagents which are not particularly described are those which are known or would be generally known and available to those skilled in the art. Exemplitive compounds of the invention produced in accordance with the above-described reaction schemes are identified below by Example Numbers 1-189.

PREPARATION OF INTERMEDIATES 3-9

General Procedure for the Preparation of Nitroalkenes 3

Commercially available thiophene-2- or thiophene-3-carboxaldehyde (1 eq) was dissolved in the nitroalkane (4 eq) and treated with methylamine hydrochloride (0.4 eq), sodium acetate (0.4 eq) and glacial acetic acid (0.4 eq). This mixture was warmed to 55°-60° C. for 6 to 16 hours. After the volatiles had been removed under reduced pressure, the residue was treated with water. If a solid did not form, the aqueous mixture was extracted with $CH_2Cl_2$ and the combined extract was dried ($Na_2SO_4$). Solvent removal produced the desired thiophene compound 3.

2-(2-Nitro-1-propenyl)thiophene

Prepared in quantitative yield. A sample was recrystallized from ether/hexane; mp 68°-70° C.

2-(2-Nitro-1-pentenyl)thiophene

Prepared in 93% yield. A sample was recrystallized from hexane to afford a bright yellow solid; mp 25°-25.5° C.; IR (KBr) 2963, 2933, 2873, 1637, 1514,1501,1463,1436,1421,1377,1332,1304,1278,1242,12-15,1054, 1009, 860 and 710 cm$^{-1}$.

Elemental analysis calculated (Anal. Calc'd) for: $C_9H_{11}NO_2S$: C,54.80;H,5.62;N,7.10. Found: C, 54.889 H, 5.58; N, 7.12.

3-(2-Nitro-1-propenyl)thiophene

Prepared in 94% yield. A sample was recrystallized from 2-propanol; mp 68°-69° C.

Anal. Calc'd for $C_7H_6NO_2S$: C, 49.68; H, 4.17; N, 8.28. Found: C, 49.69, H, 4.22; N, 8.05.

3-(2-Nitro-1-pentenyl)thiophene

Prepared as a yellow solid in 91% yield; mp 52°-54.5° C.; IR (KBr) 3113, 3103,2962,2948,2928,2871,1642,1517,1504,1434,1338,13-07,1276, 1250, 1168, 941, 866, 795 and 631 cm$^{-1}$.

Anal. Calc'd for $C_9H_{11}NO_2S$: C, 54.81; H, 5.62; N, 7.10. Found: C, 54.84; H, 5.60; N, 7.00.

3-(2-Nitroethenyl)thiophene

When $R_2$ Was H the thiophene-3-carboxaldehyde (1 eq) was dissolved in 2-propanol and treated with nitromethane (1 eq), benzylamine (0.065 eq) and glacial acetic acid (0.1 3 eq). After a 60 min reflux period, the mixture was cooled and the solid was collected and washed with ice-cold ether to afford the product (56%); mp 94.5°-96.5° C.

2-Chloro-3-(2-nitro-1-propenyl)thiophene

The title compound was prepared in 58% yield starting with 2-chlorothiophene-3-carboxaldehyde. A sample was recrystallized from $CH_2Cl_2$/ether/hexane to afford a bright yellow solid; mp 73°-76° C.; IR (KBr) 1645, 1500, 1415, 1305, 1255, 1095, 1035, 935, 735 and 620 cm$^{-1}$.

Anal. Calc'd for $C_7H_6ClNO_2S$: C, 41.29; H, 2.97; N, 6.88; S, 15.74. Found: C, 41.14, H, 3.03; N, 6.64; S, 15.77.

General Procedure for the Preparation of Nitroalkanes 4

3-(1-Nitro-2-propyl)thiophene

When $R_2$ was H, the 3-(2-nitroethenyl)thiophene (1 eq) was suspended in hexane, cooled to 5° C. in an ice bath under nitrogen and slowly treated with 2N trimethylaluminum in hexane (2.6 eq). After 30 min, the solution was quenched with 3N HCl, diluted with ether and filtered. The organic layer was dried ($Na_2SO_4$) and condensed under reduced pressure to afford the crude product. This material was purified by flash silica gel column chromatography using 70% hexane in $CH_2Cl_2$. The product was obtained as a colorless oil (80%); MH$^+$ at m/z 172.

General Procedure for the Preparation of Aminoalkenes 5

A THF or ether solution of the nitro compounds 3 or 4 (1 eq) was slowly added to an excess of LAH (2-4 eq) in either THF or ether under nitrogen (cooling may be necessary). The reaction mixture was then either stirred at rt for 16 hours or warmed to reflux for 4-6 hours and then carefully quenched with a freshly prepared saturated $Na_2SO_4$ Solution. The solid was removed and washed several times with solvent. The combined filtrate was condensed in vacuo to afford the crude product.

2-(2-Amino-1-propyl)thiophene hydrochloride

This material was prepared in 64% yield starting with 2-(2-nitro-1-propenyl)thiophene. A portion of this amine was treated with HCl/2-propanol/ether to afford the hydrochloride salt; mp 143°-145.5° C.

2-(2-Amino-1-pentyl)thiophene

This material was prepared in 80% yield starting with 2-(2-nitro-1-pentenyl)thiophene; MH$^+$ at m/z 170.

3-(2-Aminoethyl)thiophene hydrochloride

This material was prepared in 77% yield starting with 3-(2-nitroethenyl)thiophene. A portion of this amine was treated with HCl/2-propanol to afford the hydrochloride salt; mp 208°-211.5° C.

Anal. Calc'd for $C_6H_9NS.HCl$: C, 44.03; H, 6.16;N, 8.56; S, 19.59. Found: C, 44.03; H, 6.21; N, 8.53; S, 19.39.

3-(2-Amino-1-propyl)thiophene hydrochloride

This material was prepared in 91% yield starting with 3-(2-nitro-1-propenyl)thiophene. A portion of this material was treated with HCl/2-propanol/ether to afford the hydrochloride salt; mp 135°–136.5° C.

3-(1-Amino-2-propyl)thiophene hydrochloride

This material was prepared in 98% yield starting with 3-(1-nitro-2-propyl)thiophene; MH+ at m/z 142. This amine was treated with HCl/2-propanol/ether to afford the hydrochloride salt; mp 95 (softens) 103.5°–104.5° C.; IR (KBr) 2998, 2977, 2941, 2894, 2823, 2711, 2707, 2602, 1602, 1527, 1475, 1453, 1085, 988, 773 and 685 cm$^{-1}$.

Anal. Calc'd for $C_7H_{11}NS \cdot HCl$: C, 47.31; H, 6.81; N, 7.88. Found: C, 47.64; H, 6.89; N, 7.87.

2-Chloro-3-(2-Amino-1-propyl)thiophene

This material was prepared in 98% yield starting with 2-chloro-3-(2-nitro-1-propenyl)thiophene; MH+ at m/z 176.

3-(2-Amino-1-pentyl)thiophene oxalate

This material was prepared in 96% yield starting with 3-(2-nitro-1-pentenyl)thiophene; MH+ at m/z 170. This amine was treated with oxalic acid in acetone/ether to afford the oxalate salt; mp 90.5 (shrinks) 95°–99° C.; IR (KBr) 3184, 3089, 3015, 3006, 2960, 2933, 2875, 1741, 1733, 1719, 1702, 1652, 1635, 1617, 1590, 1560, 1540, 1500, 1467, 1404, 1279, 1219, 1122, 1112, 780 and 720 cm$^{-1}$. Anal. Calc'd for $C_9H_{15}NS \cdot C_2H_2O_4 \cdot \frac{1}{4}H_2O$: C, 50.09; H, 6.69; N, 5.31. Found: C, 50.39; H, 6.60; N, 5.30.

General Procedure for the Preparation of Amides 6 (Table I)

A CH$_2$Cl$_2$ solution of the aminoethylthiophene 5 (1 eq), triethylamine (1.4 eq) and 4-dimethylaminopyridine (0.1 eq) at 0° C. under nitrogen was treated slowly with a CH$_2$Cl$_2$ solution of the necessary acid chloride (1.2 eq). After this mixture had stirred at 0° C. (or rt) overnight, it was quenched with aqueous citric acid. The CH$_2$Cl$_2$ layer was washed with brine and dried (Na$_2$SO$_4$) and then condensed in vacuo to afford the crude amide in quantitative yield. This material was either used directly in the next step or purified by flash silica gel chromatography (see Table I for specific examples).

General Procedure for the Preparation of Cyclic Amines 7 ($R_3=H$) from Amines 5 (Table II)

The amine 5 (10 mmol) was slurried in water (3 ml) and treated with formaldehyde (37% wt percent in water, 11 mmol). This solution was placed in a 90° C. oil bath for 3 hours under nitrogen. The aqueous mixture was extracted with ether and the combined organic extract was dried (MgSO$_4$). Solvent removal produced the crude hexahydrotriazine intermediate which was treated with HCl/isopropanol (80 mmol) and placed in a 50°–55° C. oil bath for 6 hours. The resulting beige solid was isolated and washed with ether (see Table I for specific examples).

General Procedure for the Preparation of Cyclic Amines 7 from Amides 6 (Tables II & III)

A dry toluene or xylene (12.5 ml) solution of the amide 6 (10 mmol) was treated dropwise with POCl$_3$ (20–50 mmol) under nitrogen at rt. The reaction was stirred at rt for 16 hours (alternatively, the POCl$_3$ reaction was warmed to reflux for 3–5 hours) and then the solvents were carefully removed under vacuum. The dark residue was dissolved in EtOH (12.5 ml) and cooled in an ice-bath. The pH of the solution was adjusted to 2–3 with 2N NaOH and then slowly treated with NaBH$_4$ (20 mmol). This mixture was stirred at rt for 16 hours, carefully quenched with 2N HCl and condensed in vacuo. The acidic aqueous residue was warmed on a steambath for 15–30 min and cooled. Some of the compounds in Table II crystallized at this point as their hydrochloride salts. The filtrate was treated with NaOH to afford a basic solution that was extracted with CH$_2$Cl$_2$. The combined extract was washed with brine and dried (Na$_2$SO$_4$). Solvent removal produced the crude material that was purified by flash silica gel chromatography using 1–5% MeOH in CH$_2$Cl$_2$. The column chromatography allowed isolation of the trans isomers reported in Table III.

If after the above steambath stage nothing crystallized, then the entire residue was treated with NaOH until basic and extracted with CH$_2$Cl$_2$. The combined extract was washed with brine and dried (Na$_2$SO$_4$). Solvent removal produced the crude material that was either treated with HCl/2-propanol (excess) or purified by flash silica gel chromatography using 1–5% MeOH in CH$_2$Cl$_2$.

General Procedure for the Preparation of Cyanomethyl Compounds 7A or 24A from Cyclic Amines 7 or 24

The amine 7 or 24 (free base or HCl salt, 10 mmol) and an excess of NaHCO$_3$ (30 mmol) in 2-propanol (20 mmol) were treated with chloroacetonitrile (100 mmol) under nitrogen. This mixture was warmed to reflux for 4 hours, the solvent was removed under vacuum and the dark residue was purified by flash silica gel chromatography using 15% EtOAc in hexane. The desired compound 7A or 24A was obtained as a yellow oil (For 7A: see Table IV & V for specific examples).

General Procedure for the Preparation of Aminoethyl Compounds 9 or 25

The cyanomethyl compound 7A or 24A from above (10 mmol) in THF (15 ml) was slowly added to a mixture of LAH (20 mmol) in THF (15 ml). This mixture was placed in a 50° C. oil bath for 4 hours and then carefully quenched with a freshly prepared saturated aqueous Na$_2$SO$_4$ solution. The precipitate was removed and leached with hot THF. The combined filtrate was condensed under reduced pressure to afford the crude aminoethyl compound 9 or 25 as an oil (For 9: see Table VI & VII for specific examples).

TABLE I

Aminoethyl Thiophenes 6 Intermediates

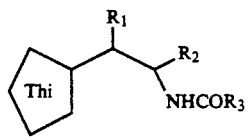

6

| | $R_1$ | $R_2$ | $R_3$ | % Yield | Physical Appearance | Mp (°C.) | Mass Spec and/or IR (KBr, cm$^{-1}$) |
|---|---|---|---|---|---|---|---|
| 6d | H | H | $CH_3$ | 33 | tan solid | 69–72 | 3280, 3100, 1635, 1550, 800, 780, 600 |
| 6e | H | H | $C_4H_9$ | 94 | light brown solid | 47–50 | 3320, 2970, 2940, 1650, 1550, 785 |
| 6f | H | H | $C_6H_{13}$ | 100 | dark solid | — | MH$^+$ at m/z 240 |
| 6g | H | H | $C_6H_5$ | 100 | beige solid | 107–108 | 3350, 1640, 1545, 1080, 780, 700 |
| 6h | H | $CH_3$ | $CH_3$ | 95 | yellow liquid | | MH$^+$ at m/z 184 |
| 6i | H | $CH_3$ | $C_4H_9$ | 75 | orange liquid | | (neat) 3300, 2995, 2970, 2910, 1650, 1560, 1465, 1395, 1280, 1245, 790, 755 |
| 6j | H | $CH_3$ | $C_6H_{13}$ | 100 | orange oil | | MH$^+$ at m/z 254; IR (neat) 3300, 2960, 2940, 2860, 1640, 1550, 1450, 780 |
| 6k | H | $CH_3$ | $C_6H_5$ | 100 | off-white solid | — | — |
| 6l | H | $CH_3$ | 4-OMeC$_6$H$_4$ | 91 | white solid | — | MH$^+$ at m/z 276; IR 3290, 3100, 2970, 1630, 1550, 1500, 1350, 1310, 1260, 1180, 1120, 1030, 850 |
| 6m | H | $CH_3$ | 4-ClC$_6$H$_4$ | 72 | white solid | — | MH$^+$ at m/z 280; IR 3320, 1640, 1530, 1480, 1310, 1150, 1090, 840, 780 |
| 6n | H | $CH_3$ | 2-thienyl | 100 | yellow oil | | MH$^+$ at m/z 252; IR (neat) 3300, 3100, 2990, 2920, 1630, 1540, 1450, 1420, 1270, 1140, 1080, 860 |
| 6o | H | $C_3H_7$ | $CH_3$ | 100 | brown oil | | — |
| 6p | $CH_3$ | H | $CH_3$ | 71 | liquid | | MH$^+$ at m/z 184; IR (neat) 3300, 3100, 2920, 1650, 1550, 1370, 1280, 850, 780 |
| 6u | H | $CH_3$ | $CH_3$ | 72 | orange oil | | — |
| 6v | H | $CH_3$ | $CH_3$ | 64 | dark liquid | | MH$^+$ at m/z 218; IR (neat) 3300, 3100, 2990, 2940, 1645, 1550, 1380, 1300, 1150, 1030, 835, 735, 700, 675 |

TABLE II

Thiophenes Intermediates 7

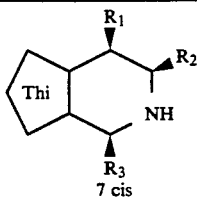

7 cis

| | $R_1$ | $R_2$ | $R_3$ | % Yield | Physical Appearance | Mp (°C.) | Salt | Mass Spec and/or IR (KBr, cm$^{-1}$) |
|---|---|---|---|---|---|---|---|---|
| Thi = 2,3-dimethyl-thiophene | | | | | | | | |
| 7a | H | H | H | 59 | beige solid | 210–213 | HCl | 2730, 1445, 1435, 720, 710 |
| 7b | H | CH$_3$ | H | 60 | tan solid | 243–245 | HCl | 2720, 2620, 2550, 1445, 1135, 1075, 835, 730, 715 |
| 7c | H | C$_4$H$_9$ | H | 85 | off-white solid | 173–174.5 | HCl | 2910, 2700, 2580, 2460, 1580, 1430, 1320, 830, 700 |
| 7d | H | H | CH$_3$ | 65 | light brown solid | 229–230.5 | HCl | 2780, 2730, 1450, 1430, 1375, 1295, 725 |
| 7e | H | H | C$_4$H$_9$ | 96 | dark liquid | | | MH$^+$ at m/z 196; IR (neat) 2930, 1465, 1450, 1430, 700 |
| 7f | H | H | C$_6$H$_{13}$ | 57 | white solid | 161–164 | HCl | 2920, 2770, 2720, 2695, 2500, 1465, 1430, 1035, 720 |
| 7g | H | H | C$_6$H$_5$ | 46 | white solid | 116–120 | — | 3250, 2900, 2810, 1445, 1100, 865, 730, 705, 675 |
| 7h-cis | H | CH$_3$ | CH$_3$ | 50 | white solid | 289.5–290.5 | HCl | 2940, 2740, 2510, 2470, 1600, 1585, 1375, 1050, 735 |
| 7i-cis | H | CH$_3$ | C$_4$H$_9$ | 95 | liquid | | | MH$^+$ at m/z 210; IR (neat) 2940, 2900, 1660, 1450, 1370, 1160, 700 |
| 7j-cis | H | CH$_3$ | C$_6$H$_{13}$ | 23 | white solid | 222–223 | HCl | 2940, 2700, 2510, 1460, 710 |
| 7k-cis | H | CH$_3$ | C$_6$H$_5$ | 77 | white solid | 158 darkens 161–163 | HCl | 3450, 2920, 2720, 2620, 2520, 1460, 1430, 1295, 1150, 740, 720, 705, 555 |
| 7l-cis | H | CH$_3$ | 4-OMeC$_6$H$_4$ | 34 | white solid | 91–93.5 | — | 3340, 2980, 2860, 1620, 1520, 1250, 1040 |
| 7m-cis | H | CH$_3$ | 4-ClC$_6$H$_4$ | 59 | white solid | 197–199 | C$_2$H$_2$O$_4$ | 3440, 2700, 1590, 1490, 1280, 1190 |
| 7n-cis | H | CH$_3$ | 2-thienyl | 93 | white solid | 209.5–211 | C$_2$H$_2$O$_4$ | 3000, 1740, 1640, 1400, 1290, 1180, 710 |
| 7o-cis | H | C$_3$H$_7$ | CH$_3$ | 78 | white solid | 243–245.5 | HCl | 3110, 2540, 2480, 1590, 1580, 1450, 1430, 1370, 730 |
| 7p-cis | CH$_3$ | H | CH$_3$ | | Not Isolated Pure | | | MH$^+$ at m/z 168; |
| Thi = 2,3-dimethyl-thiophene (other isomer) | | | | | | | | |
| 7t | H | H | H | 47 | white solid | | | J. P. Maffrand and F. Eloy, J. Heterocyclo. Chem., 1976, 13, 1347 |
| 7u-cis | H | CH$_3$ | CH$_3$ | 42 | pale peach-colored solid | 279–281 (dec) | HCl | 2950, 2740, 2470, 1600, 1585, 1460, 1425, 1385, 1065, 855, 740, 685, 625, 375, 305 |

TABLE II-continued

Thiophenes Intermediates 7

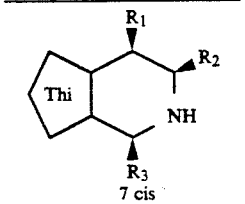

7 cis

| | $R_1$ | $R_2$ | $R_3$ | % Yield | Physical Appearance | Mp (°C.) | Salt | Mass Spec and/or IR (KBr, cm$^{-1}$) |
|---|---|---|---|---|---|---|---|---|
| 7v-cis | 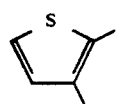 | H | CH$_3$ | CH$_3$ | 12 | light yellow liquid | | | MH$^+$ at m/z 202 |

TABLE III

Thiophenes Intermediates 7

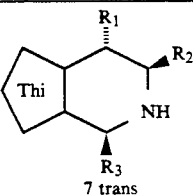

7 trans

| | $R_1$ | $R_2$ | $R_3$ | % Yield | Physical Appearance | Mp (°C.) | Salt | Mass Spec and/or IR (KBr, cm$^{-1}$) |
|---|---|---|---|---|---|---|---|---|
| 7h-trans | | H | CH$_3$ | CH$_3$ | 1.5 | white solid | 272–273 | HCl | 2940, 2800, 2740, 2700, 2450, 1590, 1445, 1380, 1325, 1145, 735, 725, 410 |
| 7j-trans | | H | CH$_3$ | C$_6$H$_{13}$ | 9.6 | tan material | — | | MH$^+$ at m/z 238; IR 2950, 2910, 2850, 1650, 1450, 1370, 1025, 725, 695 |
| 7k-trans | | H | CH$_3$ | C$_6$H$_5$ | 20 | white solid | 150 darkens 155-157 | HCl | 2960, 2910, 2660, 2520, 1575, 1455, 1070, 960, 785, 765, 725, 705, 620, 570, 325 |
| 7j-trans | | H | CH$_3$ | 4-OMeC$_6$H$_4$ | 9 | liquid | | | MH$^+$ at m/z 260; IR (neat) 2980, 2920, 2840, 1610, 1510, 1450, 1240, 1170, 1030, 830, 700 |
| 7m-trans | | H | CH$_3$ | 4-ClC$_6$H$_4$ | 9 | yellow solid | | | MH$^+$ at m/z 264; IR 3340, 1490, 1410, 1350, 1090, 820, 720 |
| 7p-trans | | CH$_3$ | H | CH$_3$ | | Not Isolated Pure | | | MH$^+$ at m/z 168; |
| 7u-trans | 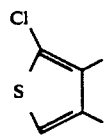 | H | CH$_3$ | CH$_3$ | | | | | Not Characterized |

TABLE III-continued

Thiophenes Intermediates 7

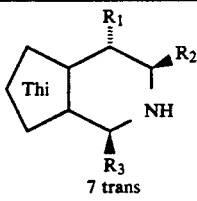

7 trans

| | R₁ | R₂ | R₃ | % Yield | Physical Appearance | Mp (°C.) | Salt | Mass Spec and/or IR (KBr, cm⁻¹) |
|---|---|---|---|---|---|---|---|---|
| 7v-trans | H | CH₃ | CH₃ | 13 | light yellow liquid | | | MH⁺ at m/z 202 |

TABLE IV

Thiophenes Cyanomethyl Intermediates

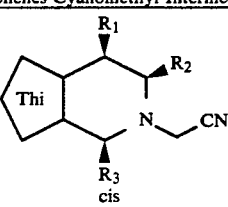

cis

| | R₁ | R₂ | R₃ | % Yield | Physical Appearance | Mp (°C.) | Salt | Mass Spec and/or IR (neat, cm⁻¹) |
|---|---|---|---|---|---|---|---|---|
| a | H | H | H | 93 | yellow oil | | | MH⁺ at m/z 179; IR 2940, 2830, 1450, 1330, 1150, 715 |
| b | H | CH₃ | H | 100 | light yellow oil | | | MH⁺ at m/z 193 |
| c | H | C₄H₉ | H | 90 | tan oil | | | MH⁺ at m/z 235; IR 2990, 2760, 1440, 1380, 1260, 1150, 1110, 730, 700 |
| d | H | H | CH₃ | 84 | light yellow oil | | | MH⁺ at m/z 193 |
| e | H | H | C₄H₉ | 80 | dark liquid | | | MH⁺ at m/z 235; IR 2930, 2860, 1450, 1320, 1135, 1100, 860, 710 |
| f | H | H | C₆H₁₃ | 65 | light orange liquid | | | 2920, 2850, 1460, 1325, 1135, 1100, 866, 710 |
| g | H | H | C₆H₅ | 77 | brown solid | 111–111.5 | | (KBr) 2810, 2230, 1450, 1420, 1130, 1100, 895, 750, 715, 700 |
| h-cis | H | CH₃ | CH₃ | 74 | white solid | 168–170 (dec) | HCl | (KBr) 3060, 2930, 1455, 1435, 1385, 1260, 1150, 1145, 970, 835, 780, 750 |
| i-cis | H | CH₃ | C₄H₉ | 65 | liquid | | | MH⁺ at m/z 249; IR 2980, 2940, 2890, 1700, 1480, 1430, 1390, 1190, 1120, 750 |
| j-cis | H | CH₃ | C₆H₁₃ | 54 | liquid | | | MH⁺ at m/z 277; IR 2920, 2840, 1450, 1420, 1370, 1170, 1100, 730 |
| k-cis | H | CH₃ | C₆H₅ | 88 | pale purple solid | — | | — |
| l-cis | H | CH₃ | 4-OMeC₆H₄ | 91 | liquid | | | MH⁺ at m/z 299; IR 2980, 2840, 1610, 1500, 1420, 1240, 1180, 1210, 1030, 840, 740 |

TABLE IV-continued

Thiophenes Cyanomethyl Intermediates

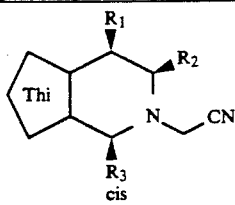
cis

| | $R_1$ | $R_2$ | $R_3$ | % Yield | Physical Appearance | Mp (°C.) | Salt | Mass Spec and/or IR (neat, cm$^{-1}$) |
|---|---|---|---|---|---|---|---|---|
| m-cis | H | CH$_3$ | 4-ClC$_6$H$_4$ | 62 | liquid | | | MH$^+$ at m/z 303; IR 3000, 2960, 1600, 1490, 1430, 1330, 1190, 1090, 810, 730 |
| n-cis | H | CH$_3$ | 2-thienyl | 93 | white solid | 209.5–211 | C$_2$H$_2$O$_4$ | (KBr) 3100, 2500, 1740, 1640, 1400, 1290, 1180, 710 |
| o-cis | H | C$_3$H$_7$ | CH$_3$ | 27 | tan oil | | | — |
| p-cis | CH$_3$ | H | CH$_3$ | | | | | Not Characterized |

![thiophene with methyl groups]

| | | | | | | | | |
|---|---|---|---|---|---|---|---|---|
| t | H | H | H | 100 | brown oil | | | MH$^+$ at m/z 179 |
| u-cis | H | CH$_3$ | CH$_3$ | 36 | yellow solid | — | | — |

![chlorothiophene with methyl groups]

| | | | | | | | | |
|---|---|---|---|---|---|---|---|---|
| v-cis | H | CH$_3$ | CH$_3$ | 84 | green solid | | | MH$^+$ at m/z 241; IR (KBr) 2990, 1465, 1430, 1385, 1185, 1015, 865, 840 |

TABLE V

Thiophenes Cyanomethyl Intermediates

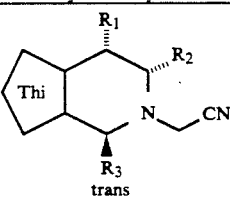
trans

| | $R_1$ | $R_2$ | $R_3$ | % Yield | Physical Appearance | Mp (°C.) | Mass Spec and/or IR (neat, cm$^{-1}$) |
|---|---|---|---|---|---|---|---|

![thiophene with methyl groups]

| | | | | | | | |
|---|---|---|---|---|---|---|---|
| h-trans | H | CH$_3$ | CH$_3$ | | | | Not Characterized |
| j-trans | H | CH$_3$ | C$_6$H$_{13}$ | 59 | liquid | | MH$^+$ at m/z 277; IR 2960, 2920, 2850, 1450, 1370, 1140, 1120, 700 |
| k-trans | H | CH$_3$ | C$_6$H$_5$ | 34 | white solid | — | — |
| l-trans | H | CH$_3$ | 4-OMeC$_6$H$_4$ | 92 | liquid | | MH$^+$ m/z 299; IR 2990, 2940, 2850, 1610, 1510, 1460, 1240, 1180, 1040, 840, 740 |
| m-trans | H | CH$_3$ | 4-ClC$_6$H$_4$ | 93 | liquid | | MH$^+$ at m/z 303; IR 3100, 3000, 2940, 1600, 1490, 1430, 1340, 1140, 1100, 880, 710 |
| p-trans | CH$_3$ | H | CH$_3$ | | | | Not Characterized |

TABLE V-continued

Thiophenes Cyanomethyl Intermediates

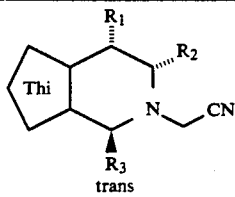

| | $R_1$ | $R_2$ | $R_3$ | % Yield | Physical Appearance | Mp (°C.) | Mass Spec and/or IR (neat, cm$^{-1}$) |
|---|---|---|---|---|---|---|---|
| u-trans | H | CH$_3$ | CH$_3$ | | | | Not Characterized |
| v-trans | H | CH$_3$ | CH$_3$ | 91 | dark liquid | | MH$^+$ at m/z 241; IR 3000, 1430, 1380, 1325, 1120, 1000, 860, 740 |

(u-trans: thiophene with methyl substituents; v-trans: chlorothiophene with methyl substituents)

TABLE VI

Thiophenes Intermediates 9

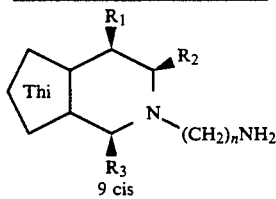

| | $R_1$ | $R_2$ | $R_3$ | n | % Yield | Physical Appearance | Mp (°C.) | Mass Spec and/or IR (neat, cm$^{-1}$) |
|---|---|---|---|---|---|---|---|---|
| 9a | H | H | H | 2 | 98 | yellow oil | | MH$^+$ at m/z 183; IR 3360, 2920, 2800, 1440, 1115, 885, 700 |
| 9b | H | CH$_3$ | H | 2 | 84 | tan oil | | MH$^+$ at m/z 197; IR 3380, 2980, 2930, 2840, 1590, 1450, 1370, 1140, 840, 700 |
| 9c | H | C$_4$H$_9$ | H | 2 | 87 | yellow oil | | MH$^+$ at m/z 239; IR 3100, 2680, 1570, 1450, 1350, 1130, 1090, 830, 690 |
| 9d | H | H | CH$_3$ | 2 | 98 | oil | | MH$^+$ at m/z 197; IR 2970, 2930, 1455, 1445, 1370, 1315, 860, 705 |
| 9e | H | H | C$_4$H$_9$ | 2 | 100 | oil | | MH$^+$ at m/z 239; IR 2930, 2860, 1460, 1005, 705 |
| 9f | H | H | C$_6$H$_{13}$ | 2 | 93 | light yellow oil | | MH$^+$ at m/z 267; IR 2920, 2850, 1460, 1100, 1000, 700 |
| 9g | H | H | C$_6$H$_5$ | 2 | 100 | yellow viscous oil | | MH$^+$ at m/z 259; IR 3390, 2970, 2940, 2820, 1455, 750, 715 |
| 9h-cis | H | CH$_3$ | CH$_3$ | 2 | 98 | yellow oil | | MH$^+$ at m/z 211 |
| 9i-cis | H | CH$_3$ | C$_4$H$_9$ | 2 | 90 | liquid | | MH$^+$ at m/z 253; IR 3380, 2960, 2920, 2870, 1590, 1460, 1380, 1160, 740, |

TABLE VI-continued

Thiophenes Intermediates 9

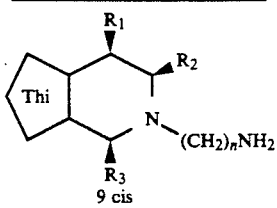

9 cis

| | R₁ | R₂ | R₃ | n | % Yield | Physical Appearance | Mp (°C.) | Mass Spec and/or IR (neat, cm⁻¹) |
|---|---|---|---|---|---|---|---|---|
| 9j-cis | H | CH₃ | C₆H₁₃ | 2 | 88 | liquid | | 710<br>MH⁺ at m/z 281; IR 3360, 2920, 2840, 1580, 1460, 1370, 700 |
| 9k-cis | H | CH₃ | C₆H₅ | 2 | 91 | yellow oil | | — |
| 9l-cis | H | CH₃ | 4-OMeC₆H₄ | 2 | 89 | liquid | | MH⁺ at m/z 303; IR 3400, 3040, 2750, 1620, 1510, 1460, 1310, 1250, 1040, 850, 720 |
| 9m-cis | H | CH₃ | 4-ClC₆H₄ | 2 | 100 | liquid | | MH⁺ at m/z 307; IR 3400, 2980, 2940, 1600, 1490, 1290, 1180, 1090, 1020, 840, 700 |
| 9n-cis | H | CH₃ | 2-thienyl | 2 | 96 | liquid | | MH⁺ at m/z 279; IR 3360, 3100, 3060, 2960, 2910, 2830, 1570, 1430, 1280, 1230, 1190, 1040, 700 |
| 9o-cis | H | C₃H₇ | CH₃ | 2 | 94 | tan material | | MH⁺ at m/z 239; IR (KBr) 2970, 2940, 2880, 1465, 1455, 1375, 1305, 1155, 1100, 1085, 835, 740, 710 |
| 9p-cis | CH₃ | H | CH₃ | 2 | 74 | colorless liquid | | MH⁺ at m/z 211; IR 3360, 3010, 3080, 2960, 2800, 1570, 1510, 1370, 1340, 1180, 840, 720 |
| 9q-cis | H | CH₃ | CH₃ | 3 | 100 | yellow oil | | MH⁺ at m/z 225 |
| 9r-cis | | CH₃ | CH₃ | 4 | 100 | solid | | MH⁺ at m/z 239; IR (KBr) 3640, 2360, 1650, 1580, 1480, 1450, 1380, 1310, 1240, 1040, 840, 710 |
| 9s-cis | H | C₃H₇ | CH₃ | 3 | 100 | yellow waxy solid | | — |

Thi =

<chemical structure: 2,3-dimethylthiophene>

| | R₁ | R₂ | R₃ | n | % Yield | Physical Appearance | Mp (°C.) | Mass Spec and/or IR (neat, cm⁻¹) |
|---|---|---|---|---|---|---|---|---|
| 9t | H | H | H | 2 | 72 | yellow material | | MH⁺ at m/z 183; IR (KBr) 3360, 2920, 2800, 1590, 1460, 1350, 1320, 1160, 1110, 830, 700 |
| 9u-cis | H | CH₃ | CH₃ | 2 | 96 | light yellow liquid | | — |

Thi =

<chemical structure: 2-chloro-3,4-dimethylthiophene>

| | R₁ | R₂ | R₃ | n | % Yield | Physical Appearance | Mp (°C.) | Mass Spec and/or IR (neat, cm⁻¹) |
|---|---|---|---|---|---|---|---|---|
| 9v-cis | H | CH₃ | CH₃ | 2 | 96 | light yellow liquid | | MH⁺ at m/z 245 |

TABLE VII

Thiophenes Intermediates 9

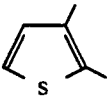

9 trans

| | R₁ | R₂ | R₃ | n | % Yield | Physical Appearance | Mp (°C.) | Mass Spec and/or IR (neat, cm⁻¹) |
|---|---|---|---|---|---|---|---|---|
| 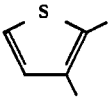 | | | | | | | | |
| 9h-trans | H | CH₃ | CH₃ | 2 | | | | Not Characterized |
| 9j-trans | H | CH₃ | C₆H₁₃ | 2 | 89 | liquid | | MH⁺ at m/z 281; IR 2960, 2920, 2840, 1580, 1450, 1370, 1140, 1110, 830, 700 |
| 9k-trans | H | CH₃ | C₆H₅ | 2 | 100 | red-brown oil | | — |
| 9l-trans | H | CH₃ | 4-OMeC₆H₄ | 2 | 80 | liquid | | MH⁺ at m/z 303; IR 3400, 2980, 2940, 2860, 1615, 1515, 1310, 1250, 1180, 1040, 840, 720 |
| 9m-trans | H | CH₃ | 4-ClC₆H₄ | 2 | 81 | liquid | | MH⁺ at m/z 307; IR 3400, 2980, 2940, 1600, 1490, 1450, 1380, 1190, 1020, 830, 720 |
| 9p-trans | CH₃ | H | CH₃ | 2 | 92 | yellow liquid | | MH⁺ at m/z 211; IR 3400, 3360, 3280, 3100, 3060, 2980, 2800, 1580, 1560, 1450, 1370, 1310, 1150, 1080, 820 |
| 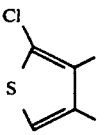 | | | | | | | | |
| 9u-trans | H | CH₃ | CH₃ | 2 | | | | Not Characterized |
| 9v-trans | H | CH₃ | CH₃ | 2 | 98 | yellow liquid | | MH⁺ at m/z 245 |

Method A: General Procedure for the Preparation of Benzamides 15 or 26

The amino compound 12 or 25 (10 mmol) in CH₂Cl₂ (30 mL) was treated with triethylamine (20 mmol) and 4-dimethylaminopyridine (2.5 mmol) under nitrogen. This ice-cold solution was slowly treated with the necessary benzoyl chloride or sulfonyl chloride (11 mmol) in CH₂Cl₂ (30 ml). The mixture was allowed to warm to rt and stirred for 16 hours. The dark CH₂Cl₂ solution was washed with water and dried (MgSO₄). Solvent removal produced the crude product 15 or 26 that was purified by flash silica gel chromatography using 1-5% methanol in CH₂Cl₂.

Method B: General Procedure for the Preparation of the Sulfonamides 16 or 27

The amino compound 12 or 25 (10 mmol) in CH₂Cl₂ (30 mL) was teated with triethylamine (20 mmol) and 4-dimethylaminopyridine (2.5-5 mmol) under nitrogen. This ice-cold solution was slowly treated with the necessary sulfonyl chloride (11 mmol) in CH₂Cl₂ (30 mL). The mixture was allowed to warm to rt and stirred for 16 hours. The CH₂Cl₂ solution was washed with water and saturated NaHCO₃ solution and dried (MgSO₄). Solvent removal produced the crude product 16 or 27 that was purified by flash silica gel chromatography using 0.5-5% methanol in CH₂Cl₂.

Method C: General Procedure for the Preparation of the Aminobenzenes 20 or 28 by Iron Reduction The benzamide 13-19 or 26(or 27) (R₄=NO₂) (10 mmol) was slurried with iron filings (50 mmol) in ethanol (150 mL) under nitrogen. This mixture was slowly treated with concentrated HCl (44 mL) and then placed in a 60° C. oil bath for 1 hour (or alternatively in glacial acetic acid at 60°-68° C. with no HCl added). The excess iron filings was removed by filtration and the filtrate was treated with 50% NaOH while cooling in an ice bath. The slurry (pH=10–12) was filtered through Celite 545 ® and the filtercake was leached with hot ethanol. The ethanol was removed in vacuo and the aqueous residue was extracted with $CH_2Cl_2$. The combined extract was dried ($MgSO_4$) and condensed in vacuo to afford the crude aminobenzene product 20 or 28.

Method D: General Procedure for the Preparation of the Aminobenzenes 20 or 28 by Nickel (II) Chloride Hexahydrate/$NaBH_4$ Reduction The benzamide 13–19 or 26(or 27) ($R_4=NO_2$) (10 mmol) and nickel (II) chloride hexahydrate (20 mmol) were dissolved in methanol (75 mL) under nitrogen. This solution was cooled to 0° C. and carefully treated with $NaBH_4$ (40 mmol). After the reaction had stirred at 0° C. for 30 min, it was allowed to warm to rt and stirred at rt for 30 min. The methanol was removed in vacuo and the dark residue was carefully dissolved in 6N HCl. The pH of the solution was adjusted to 11 with concentrated $NH_4OH$ and then extracted with $CH_2Cl_2$. The combined extract was dried ($MgSO_4$) and condensed in vacuo to afford the crude aminobenzene product 20 or 28.

Method E: General Procedure for the Preparation of the Amides 21 or 29

A $CH_2Cl_2$ solution (50 mL) of the aminobenzene compound 20 or 28 (10 mmol) was treated with triethylamine (30 mmol) and 4-dimethylaminopyridine (5 mmol) under nitrogen at 0° C. This solution was treated with the necessary acid chloride (11 mmol) in $CH_2Cl_2$ (5 mL) and the mixture was stirred at rt for 16 hours. The $CH_2Cl_2$ layer was washed with brine and dried ($MgSO_4$). Solvent removal produced the crude product 21 or 29 which was purified by the methods described in the Examples.

Method F: General Procedure for the Preparation of the Sulfonamides 22 or 30

The aminobenzene compound 20 or 28 (10 mmol) was dissolved in ice-cold $CH_2Cl_2$ (75 ml) and pyridine (0.85 mL) under nitrogen. This solution was treated with a $CH_2Cl_2$ solution (5 mL) of the necessary sulfonyl chloride (11 mmol). The mixture was stirred at 0° C. for 3 hours and then stirred at rt for 16 hours. The $CH_2Cl_2$ layer was washed with water and saturated $NaHCO_3$ and dried ($MgSO_4$). Solvent removal produced the crude product 22 or 30 which was purified by the methods described in the Examples.

EXAMPLE 1

4,5,6,7-Tetrahydro-6-[2-(6-nitrobenzamido)ethyl]-thieno[2,3-c]pyridine Hydrochloride Prepared by Method A using amine 9a (Table VI) and isolated in 85% yield as a dark red-orange material. This material was dissolved in 2-propanol and treated with 1.1 eq. of HCl/2-propanol to afford the HCl salt as a beige solid; mp 233°–236° C.; IR (KBr) 3280, 2360, 1630, 1590, 1525, 1510, 1335 and 725 $cm^{-1}$.

Anal. Calc'd for $C_{16}H_{17}N_3O_3S \cdot HCl$: C, 52.24; H, 4.93; N, 11.42. Found: C, 52.22; H, 5.02; N, 11.15.

EXAMPLE 2

6-[2-(6-Aminobenzamido)ethyl]-4,5,6,7-tetrahydro-thieno[2,3-c]pyridine

Prepared by Method C using the nitro compound in Example 1 and isolated in quantitive yield as a tacky yellow solid; $MH^+$ at m/z 302.

EXAMPLE 3

4,5,6,7-Tetrahydro-6-[2-(4-methanesulfonamidobenzamido)ethyl]-thieno[2 3-c]pyridine Prepared by Method F using the aminobenzene in Example 2 and methanesulfonyl chloride. The product was isolated as a white foam in 66% yield after flash silica gel chromatography using 1–5% methanol in $CH_2Cl_2$. This material was crystallized from 2-propanol to afford the title compound as a light yellow solid; mp 164°–166° C.; IR (KBr) 3410, 1640, 1605, 1500, 1335, 1305, 1145 and 965 $cm^{-1}$.

Anal. Calc'd for $C_{17}H_{21}N_3O_3S_2$: C,52.24;H,4.93;N,11.42. Found: C, 52.22; H, 5.02; N, 11.15.

EXAMPLE 4

4,5,6,7-Tetrahydro-5-methyl-6-[2-(4-nitrobenzamido)ethyl]thieno[2,3-c]pyridine Monooxalate Prepared by Method A using the amine 9b (Table VI) and isolated in yield as an orange oil. This material was dissolved in acetone and treated with 1.1 eq. of oxalic acid and ether to afford the oxalate salt as a light yellow solid; mp 180°–183° C.; IR (KBr) 3340, 2550, 1760, 1650 and 1300 $cm^{-1}$.

Anal. Calc'd for $C_{17}H_{19}N_3O_3S \cdot C_2H_2O_4 \cdot \frac{1}{4}H_2O$: C, 51.87; H, 4.92; N, 9.55. Found: C, 51.89; H, 4.84; N, 9.28.

EXAMPLE 5

5-Butyl-4,5,6,7-tetrahydro-6-[2-(4-nitrobenzamido)ethyl]thieno[[2,3-c]pyridine

Prepared by Method A using the amine 9b (Table VI) and isolated in 100% yield as an orange solid. This material was recrystallized from $CH_2Cl_2$/ether/hexane to produce the title compound as a yellow solid; mp 94.5°–96.5° C.; IR (KBr) 3240, 3020, 2890, 1610, 1570, 1530, 1490, 1320, 1280 and 670 $cm^{-1}$.

Anal. Calc'd for $C_{20}H_{25}N_3O_3S$: C, 62.00; H, 6.50; N, 10.85. Found: C, 61.86; H, 6.53; N, 10.88.

EXAMPLE 6

5-Butyl-4,5,6,7-tetrahydro-6-[2-(4-nitrobenzenesulfonamido)ethyl]-thieno[2,3-c]pyridine Monooxalate Prepared by Method B using the amine 9c (Table VI) and isolated in 100% yield as a yellow oil. This material was dissolved in acetone and treated with 1.1 eq. of oxalic acid to afford the oxalate salt as a white solid; mp 166°–168° C.; IR (KBr) 3100, 2950, 2920, 2860, 1750, 1640, 1520, 1340, 1250 and 740 $cm^{-1}$.

Anal. Calc'd for $C_{19}H_{25}N_3O_4S_2 \cdot C_2H_2O_4$: C, 49.12; H, 5.30; N, 8.18. Found: C, 49.23; H, 5.23; N, 8.11.

EXAMPLE 7

6-[2-(4-Aminobenzamido)ethyl]-5-butyl-4,5,6,7-tetrahydrothieno[2,3-c]pyridine

Prepared by Method D using the nitro compound in Example 5 and isolated in 99% yield as a yellow oil;

MH+ at m/z 358; IR (neat) 3370, 2920, 1640, 1500, 1270, 1180, 1090, 900 and 830 cm$^{-1}$.

EXAMPLE 8

6-[2-(4-Aminobenzenesulfonamido)ethyl]-5-butyl-4,5,6,7-tetrahydrothieno[2,3-c]pyridine Prepared by Method D using the nitro compound in Example 6 and isolated in 94% yield as a yellow oil; MH+ at m/z 394; IR (neat) 3460, 3360, 2940, 2840, 1630, 1590, 1450, 1380, 1300, 1140 and 800 cm$^{-1}$.

EXAMPLE 9

5-Butyl-4,5,6,7-tetrahydro-6-[2-(4-methanesulfonamidobenzamido)ethyl]thieno[2,3-c]pyridine Hydrochloride Prepared by Method F using the aminobenzene from Example 7 and methanesulfonyl chloride. The product was isolated as a white foam in 72% yield after flash silica gel chromatography using 0.5-2.5% methanol in CH$_2$Cl$_2$. This material was dissolved in 2-propanol and treated with HCl/2-propanol (1.1 eq) to afford the hydrochloride salt of the title compound as a white solid; mp 224.5°-229° C.; IR (KBr) 3300, 3100, 2960, 2580, 1650, 1600, 1500, 1340, 1300, 1150 and 960 cm$^{-1}$.

Anal. Calc'd for C$_{21}$H$_{29}$N$_3$O$_3$S$_2$.HCl: C, 53.44; H, 6.41; N, 8.90. Found: C, 53.41; H, 6.51; N, 8.79.

EXAMPLE 10

5- Butyl-4,5,6,7-tetrahydro-7-[2-(4-methanesulfonamido benzenesulfonamido)ethyl]thieno[2,3-c]pyridine Hydrochloride Prepared by Method F using the aminobenzene from Example 8 and methanesulfonyl chloride. The product was isolated as a white foam in 45% yield after flash silica gel chromatography using 0.5-2.5% methanol in CH$_2$Cl$_2$. This material was dissolved in 2-propanol and treated with HCl/2-propanol (1.1 eq) to afford the hydrochloride salt of the title compound as an off-white solid; mp 93°-96° C.; IR (KBr) 1600, 1500, 1420, 1150, 1090, 960 and 840 cm$^{-1}$.

Anal. Calc'd for C$_{20}$H$_{29}$N$_3$O$_4$S$_3$.HCl.$\frac{1}{2}$C$_3$H$_8$O.$\frac{1}{2}$H$_2$O: Calc'd: C, 47.60; H, 6.41; N, 7.75. Found: C, 47.56; H, 6.68; N, 7.64.

EXAMPLE 11

4,5,6,7-Tetrahydro-7-methyl-6-[2-(4-nitrobenzamido)ethyl]thieno[2,3-c]pyridine Hydrochloride Prepared by Method A using the amine 9d (Table VI) and isolated in 100% yield as a dark orange solid without column purification. This material was dissolved in methanol and treated with HCl/2-propanol (2 eq) to afford the title compound as its hydrochloride salt (light brown solid); mp 229°-231° C.; IR (KBr) 3300, 2560, 2540, 1670, 1540, 1520, 1350, 1290, 870 and 730 cm$^{-1}$.

Anal. Calc'd for C$_{17}$H$_{19}$N$_3$O$_3$S.HCl.$\frac{1}{2}$H$_2$O: C, 52.85; H, 5.35; N, 10.88. Found: C, 52.54; H, 5.32; N, 10.63.

EXAMPLE 12

6-[2-(4-Aminobenzamido)ethyl]-4,5,6,7-tetrahydro-7-methylthieno[2,3-c]pyridine

Prepared by Method C using the nitro compound in Example 11 and isolated in 100% yield as a light yellow-orange viscous material; MH+ at m/z 316; IR (neat) 3340, 3220, 2960, 2920, 2830, 1625, 1600, 1500, 1285, 1180, 840, 735 and 700 cm$^{-1}$.

EXAMPLE 13

4,5,6,7-Tetrahydro-6-[2-(4-methanesulfonamidobenzamido)ethyl]-7-methylthieno[2,3-c]pyridine Hydrochloride Prepared by Method F using the aminobenzene from Example 12 and methanesulfonyl chloride. The product was isolated as a beige foam in 65% yield after flash silica gel chromatography using 2-5% methanol in CH$_2$Cl$_2$. This material was dissolved in 2-propanol and treated with HCl/2-propanol (1.2 eq) to afford the hydrochloride salt of the title compound as a white foamy solid; mp 114 (softens) 124°-134° C.; IR (KBr) 2920, 1645, 1605, 1500, 1330, 1300, 1145 and 965 cm$^{-1}$.

Anal. Calc'd for C$_{18}$H$_{23}$N$_3$O$_3$S$_2$.HCl: C, 50.28; H, 5.63; N, 9.77. Found: C, 49.84; H, 5.78; N, 9.46.

EXAMPLE 14

7-Butyl-4,5,6,7-tetrahydro-6-[2-(4-nitrobenzamido)ethyl]thieno[2,3-c]pyridine Monooxalate Prepared by Method A using the amine 9e (Table VI) and isolated as a yellow-orange liquid (88% yield) after silica gel chromatography (10-50% EtOAc in hexane). This material was dissolved in acetone and treated with oxalic acid (1.1 eq) to afford the title compound as a white solid; mp 177°-179° C.; IR (KBr) 3300, 1650, 1600, 1525, 1345, 1300 and 710 cm$^{-1}$.

Anal. Calc'd for C$_{20}$H$_{25}$N$_3$O$_3$S.C$_2$H$_2$O$_4$: C, 55.33; H, 5.70; N, 8.80. Found: C, 55.35; H, 5.50; N, 8.59.

EXAMPLE 15

6-[2-(4-Aminobenzamido)ethyl]-7-butyl-4,5,6,7-tetrahydro thieno[2,3-c]pyridine

Prepared by Method D using the nitro compound in Example 14 and isolated in 72% yield as a clear waxy material after silica gel chromatography (60-100% EtOAc in hexane); MH+ at m/z 358; IR (neat) 3340, 3220, 2920, 1630, 1600, 1490, 1280, 1180, 835, 765, and 700 cm$^{-1}$.

EXAMPLE 16

7-Butyl-4,5,6,7-tetrahydro-6-[2-(4-methanesulfonamidobenzamido)ethyl]thieno[2,3-c]pyridine Prepared by Method F using the aminobenzene from Example 15 and methanesulfonyl chloride. The product was isolated as a white solid after flash silica gel chromatography using CH$_2$Cl$_2$/Methanol/NH$_4$OH (97.5/2.25/0.25 to 95.75/4/0.25). This material was recrystallized from EtOAc/ether to afford the title compound as an near-white solid (80%); mp 98°-105° C.; IR (KBr) 3420, 2930, 1635, 1610, 1553, 1505, 1340, 1310 and 1155 cm$^{-1}$.

Anal. Calc'd for C$_{21}$H$_{29}$N$_3$O$_3$S$_2$: C, 57.90; H, 6.71; N, 9.65. Found: C, 58.06; H, 7.03; N, 9.56.

EXAMPLE 17

7-Butyl-4,5,6,7-tetrahydro-6-[3-(4-nitrophenoxy)propyl]thieno[2,3-c]pyridine

An acetonitrile solution (40 mL) of cyclic amine 7e (Table II) (1.45 g, 7.42 mmol) was reacted with 1-(3-chloropropoxy)-4-nitrobenzene [prepared by reacting 4-nitrophenol (1 eq) with 1-bromo-3-chloropropane (1.5 eq) in methyl ethyl ketone with K$_2$CO$_3$ (2 eq) present]. The product was isolated as a yellow oil (93%) which was crystallized from ether/hexane; mp 37.5°-38.5° C.; IR (KBr) 1611, 1595,1500,1469, 1344,1302, 1262, 1180, 1114, 848 and 752 cm$^{-1}$] (3.20 g, 15 mmol), NaI (2.23 g, 15 mmol) and K$_2$CO$_3$ (5.13 g, 37 mmol) at reflux for 16 hours under nitrogen. The solvent was removed in vacuo and the residue was slurried in water. The product was extracted into CH$_2$Cl$_2$ and the combined extract was washed with brine and dried (MgSO$_4$). Solvent removal produced a yellow oil (5.17 g) that was purified by flash silica gel chromatography using 10-20% EtOAc in hexane. There was obtained a green oil (1.85 g, 67%) that was crystallized from ether/hexane to afford the title compound as a yellow solid; mp 72°-75° C.; IR (KBr) 2930, 2850, 1590, 1500, 1325, 1255, 1105, 1025, 940, 840, 750, 700 and 655 cm$^{-1}$.

Anal. Calc'd for C$_{20}$H$_{26}$N$_2$O$_3$S: C, 64.15; H, 7.00; N, 7.48. Found: C, 64.27; H, 7.33; N, 7.43.

EXAMPLE 18

6-[3-(4-Aminophenoxy)propyl]-7-butyl-4,5,6,7-tetrahydrothieno[2,3-c]pyridine

Prepared by Method D using the nitro compound in Example 17 and isolated in 84% yield as a yellow oil after silica gel chromatography using 0.5-2.5% MeOH in CH$_2$Cl$_2$; MH+ at m/z 345; IR (neat) 3415, 3350, 2930, 2860, 1640, 1500, 1460, 1240 and 820 cm$^{-1}$.

EXAMPLE 19

7-Butyl-4,5,6,7-tetrahydro-6-[3-(4-methanesulfonamidophenoxy)propyl]thieno[2,3-c]pyridine Monooxalate Prepared by Method F using the aminobenzene from Example 18 and methanesulfonyl chloride. The product was isolated as a pink oil after flash silica gel chromatography using 0.5-4% MeOH in CH$_2$Cl$_2$. This material was dissolved in acetone and treated with oxalic acid (1.1 eq). The oxalate salt was isolated as an off-white solid (86%); mp 165.5°-169° C.; IR (KBr) 3170, 2930, 2870, 1640, 1625, 1505, 1320, 1235, 1140, 975, 960 and 705 cm$^{-1}$.

Anal. Calc'd for C$_{21}$H$_{30}$N$_2$O$_3$S$_2$·C$_2$H$_2$O$_4$: C, 53.90; H, 6.29; N, 5.47. Found: C, 53.90; H, 6.17; N, 5.28.

EXAMPLE 20

7-Butyl-4,5,6,7-tetrahydro-6-[2-(4-nitrobenzylamino)ethyl]thieno[2,3-c]pyridine 3/2 Oxalate A 2-propanol solution (4 mL) of ethylamine 9e (0.96 g, 4.03 mmol) was reacted with 4-nitrobenzyl chloride (0.35 g, 2.01 mmol), NaHCO$_3$ (0.68 g, 8.05 mmol) and NaI (0.15 g, 1.01 mmol) at reflux under nitrogen for 6 hours. The solvent was removed in vacuo and the residue was slurried in water. This aqueous mixture was extracted with CH$_2$Cl$_2$ and the combined extract was washed with brine and dried (MgSO$_4$). Solvent removal produced a crude material that was purified by flash silica gel chromatography using 0.5-3% MeOH in CH$_2$Cl$_2$. The title compound isolated (0.52 g, 69%) and treated with oxalic acid in acetone to afford an off-white solid; mp 205°-209° C.; IR (KBr) 2960, 2920, 2860, 1640, 1625, 1605, 1520, 1345 and 705 cm$^{-1}$.

Anal. Calc'd for C$_{20}$H$_{27}$N$_3$O$_2$S·3/2C$_2$H$_2$O$_4$: C, 54.32; H, 5.95; N, 8.26. Found: C, 54.31; H, 5.80; N, 8.35.

EXAMPLE 21

7-Hexyl-4,5,6,7-tetrahydro-6-[2-(4-nitrobenzamido)ethyl]thieno[2,3-c]pyridine Monomaleate Prepared by Method A using the amine 9f (Table VI) and isolated in 100% yield as a yellow liquid after silica gel chromatography using 40% EtOAc in hexane. This material was dissolved in acetone and treated with maleic acid (1.1 eq) to afford the title compound as a white fluffy solid; mp 109°-112° C.; IR (KBr) 3290, 2930, 2860, 1710, 1650, 1625, 1600, 1525, 1345, 1300, 870 and 850 cm$^{-1}$.

Anal. Calc'd for C$_{22}$H$_{29}$N$_3$O$_3$S·C$_4$H$_4$O$_4$: C, 58.74; H, 6.26; N, 7.90. Found: C, 58.75; H, 6.15; N, 7.90.

EXAMPLE 22

6-[2-(4-Aminobenzamido)ethyl]-7-hexyl-4,5,6,7-tetrahydrothieno[2,3-c]pyridine

Prepared by Method D using the nitro compound in Example 21 and isolated in 81% yield as a light yellow material after silica gel chromatography using 60-100% EtOAc in hexane; MH+ at m/z 386; IR (neat) 3340, 3220, 2920, 2850, 1625, 1605, 1500, 1285, 1185, 840 and 765 cm$^{-1}$.

EXAMPLE 23

7-Hexyl-4,5,6,7-tetrahydro-6-[2-(4-methanesulfonamidobenzamido)ethyl]thieno[2,3-c]pyridine Prepared by Method F using the aminobenzene from Example 22 and methanesulfonyl chloride. The product was isolated as a white crystalline solid (74%) after flash silica gel chromatography using 30-100% EtOAc in hexane. This material was recrystallized from CH$_2$Cl$_2$/ether to afford the title compound as a white solid; mp 132.5°-133.5° C.; IR (KBr) 3350, 2920, 1620, 1610, 1555, 1505, 1315, 1155, 1140 and 965 cm$^{-1}$.

Anal. Calc'd for C$_{23}$H$_{33}$N$_3$O$_3$S$_2$: C, 59.58; H, 7.17; N, 9.06. Found: C, 59.94; H, 7.42; N, 9.00.

EXAMPLE 24

4,5,6,7-Tetrahydro-6-[2-(4-nitrobenzamido)ethyl]-7-phenylthieno[2,3-c]pyridine

Prepared by Method A using the amine 9g (Table VI) and isolated in 76% yield as a light yellow liquid after silica gel chromatography using 15-50% EtOAc in hexane. This material was crystallized from EtOAc to afford the title compound as a light yellow solid; mp 138°-145° C. (dec); IR (KBr) 3420, 2800, 1650, 1595, 1515, 1335, 1280, 710 and 695 cm$^{-1}$.

Anal. Calc'd for C$_{22}$H$_{21}$N$_3$O$_3$S: C, 64.85; H, 5.19; N, 10.31. Found: C, 64.62; H, 5.18; N, 10.38.

EXAMPLE 25

6-[2-(4-Aminobenzamido)ethyl]-4,5,6,7-tetrahydro-7-phenylthieno[2,3-c]pyridine

Prepared by Method C using the nitro compound in Example 24 and isolated in 100% yield as a dark semi-solid; MH+ at m/z 378.

EXAMPLE 26

4,5,6,7-Tetrahydro-6-[2-(4-methanesulfonamidobenzamido)ethyl]-7-phenylthieno[2,3-c]pyridine Prepared by Method F using the aminobenzene from Example 25 and methanesulfonyl chloride. The product was isolated in 56% yield after flash silica gel chromatography using 1-4% MeOH in CH$_2$Cl$_2$. This material was recrystallized from CH$_2$Cl$_2$ to afford the title compound as a white solid; mp 185°-187° C.; IR (KBr) 3370, 3140, 1630, 1605, 1495, 1470, 13335, 1295, 1150 and 970 cm$^{-1}$.

Anal. Calc'd for C$_{23}$H$_{25}$N$_3$O$_3$S$_2$: C, 60.64; H, 5.53; N, 9.22. Found: C, 60.41; H, 5.54; N, 9.20.

EXAMPLE 27 cis-6-(2-Benzamidoethyl)-4,5,6,7-tetrahydro-5,7-dimethylthieno[2,3-c]pyridine

Prepared by Method A using the amine 9h-cis (Table VI) and isolated in 39% yield as a white solid after silica gel chromatography and recrystallization from $CH_2Cl_2$/ether/hexane; mp 105°–107.5° C.; IR (KBr) 3340, 2460, 1630, 1540, 1300 and 1150 cm$^{-1}$.

Anal. Calc'd for $C_{18}H_{22}N_2OS$: C, 68.76; H, 7.05; N, 8.91. Found: C, 68.60; H, 7.13; N, 8.70.

EXAMPLE 28 cis-4,5,6,7-Tetrahydro-5,7-dimethyl-6-[2-(4-nitrobenzamido)ethyl]-thieno[2,3-c]pyridine Hydrochloride Prepared by Method A using the amine 9h-cis (Table VI) and 4-nitrobenzoyl chloride. The purified title compound was isolated in 48% yield as an orange gummy material. A portion of this material was treated with HCl/2-propanol (1.1 eq) to afford a tan solid; mp 224°–224.5° C.; IR (KBr) 3260, 2500, 1670, 1605, 1545, 1525, 1345, 1295, 830, 740 and 725 cm$^{-1}$.

Anal. Calc'd for $C_{18}H_{21}N_3O_3S \cdot HCl$: C, 54.61; H, 5.60; N, 10.62. Found: C, 54.52; H, 5.62; N, 10.36.

EXAMPLE 29 trans-4,5,6,7-Tetrahydro-5,7-dimethyl-6-[2-(4-nitrobenzamido)ethyl]-thieno[2,3-c]pyridine Hydrochloride Prepared by Method A using the amine 9h-trans (Table VII) and 4-nitrobenzoyl chloride. The purified (silica gel column chromatography using 1–5% 2-propanol in $CH_2Cl_2$) title compound was isolated in 25% yield as an light green solid after treating the free base with HCl/2-propanol (1.1 eq); mp 262°–264° C.; IR (KBr) 3240, 2560, 1660, 1590, 1520, 1330 and 1280 cm$^{-1}$.

Anal. Calc'd for $C_{18}H_{21}N_3O_3S \cdot HCl$: C, 54.61; H, 5.60; N, 10.62. Found: C, 54.66; H, 5.74; N, 10.30.

EXAMPLE 30 cis-4,5,6,7-Tetrahydro-5,7-dimethyl-6-[2-(3-nitrobenzamido)ethyl]-thieno[2,3-c]pyridine Hydrochloride Prepared by Method A using the amine 9h-cis (Table VI) and 3-nitrobenzoyl chloride. The purified title compound was isolated in 50% yield as an off-white solid after treating the free base with HCl/2-propanol (1.1 eq); mp 234°–237° C.; IR (KBr) 3100, 2500, 1660, 1520, 1350 and 720 cm$^{-1}$.

Anal. Calc'd for $C_{18}H_{22}N_2OS \cdot HCl$: C, 54.61; H, 5.60; N, 10.62. Found: C, 54.82; H, 5.72; N, 10.41.

EXAMPLE 31 trans-4,5,6,7-Tetrahydro-5,7-dimethyl-6-[2-(3-nitrobenzamido)ethyl]-thieno[2,3-c]pyridine Hydrochloride Prepared by Method A using the amine 9h-trans (Table VII) and 3-nitrobenzoyl chloride. The purified title compound was isolated in 7% yield as a tan solid after treating the free base with HCl/2-propanol (1.1 eq); mp 218°–221° C.; IR (KBr) 3360, 2540, 1650, 1510, 1340, 1290 and 700 cm$^{-1}$.

Anal. Calc'd for $C_{18}H_{21}N_3O_3S \cdot HCl$: C, 54.61; H, 5.60; N, 10.62. Found: C, 54.63; H, 5.63; N, 10.27.

EXAMPLE 32 cis-4,5,6,7-Tetrahydro-5,7-dimethyl-6-[2-(2-nitrobenzamido)ethyl]-thieno[2,3-c]pyridine Hydrochloride Prepared by Method A using the amine 9h-cis (Table VI) and nitrobenzoyl chloride. The purified title compound was isolated in 30% yield as a tan solid after treating the free base with HCl/2-propanol (1.1 eq); mp 167.5°–171.5° C.; IR (KBr) 3360, 2500, 1780, 1550, 1390 and 1320 cm$^{-1}$.

Anal. Calc'd for $C_{18}H_{22}N_2OS \cdot HCl$: C, 54.61; H, 5.60; N, 10.62. Found: C, 54.63; H, 5.69; N, 10.43.

EXAMPLE 33 cis-6-[2-(4-Chlorobenzamido)ethyl]-4,5,6,7-tetrahydro-5,7-dimethyl-thieno[2,3-c]pyridine Monooxalate Prepared by Method A using the amine 9h-cis (Table VI) and 4-chlorobenzoyl chloride. The title compound was isolated in 100% yield. This material was converted to a white solid when treated with oxalic acid (1.1 eq) in acetone/ether; mp 151°–153° C.; IR (KBr) 3240, 2950, 1720, 1610 and 1190 cm$^{-1}$.

Anal. Calc'd for $C_{18}H_{22}N_2OS \cdot C_2H_2O_4$: C, 54.73; H, 5.28; N, 6.38. Found: C, 54.54; H, 5.11; N, 6.00.

EXAMPLE 34 cis-6-[2-(3-Chlorobenzamido)ethyl]-4,5,6,7-tetrahydro-5,7-dimethyl-thieno[2,3-c]pyridine Monooxalate Prepared by Method A using the amine 9h-cis (Table VI) and 3-chlorobenzoyl chloride. The title compound was isolated in 100% yield. This material was converted to a white solid when treated with oxalic acid (1.1 eq) in acetone/ether; mp 134.5°–138° C.; IR (KBr) 3280, 2950, 1720, 1615, 1190, 740 cm$^{-1}$.

Anal. Calc'd for $C_{18}H_{22}N_2OS \cdot C_2H_2O_4$: C, 54.73; H, 5.28; N, 6.38. Found: C, 54.77; H, 5.37; N, 6.12.

EXAMPLE 35 cis-6-[2-(2-Chlorobenzamido)ethyl]-4,5,6,7-tetrahydro-5,7-dimethyl-thieno[2,3-c]pyridine Monooxalate Prepared by Method A using the amine 9h-cis (Table VI) and 2-chlorobenzoyl chloride. The title compound was isolated in 96% yield. This material was converted to a white crystalline solid when treated with oxalic acid (1.1 eq) in acetone/ether; mp 165.5°–171° C.; IR (KBr) 3240, 1720, 1620, 1310, 1190 and 730 cm$^{-1}$.

Anal. Calc'd for $C_{18}H_{21}N_2OS \cdot C_2H_2O_4 \cdot \frac{1}{4}H_2O$: C, 54.18; H, 5.34; N, 6.31. Found: C, 54.22; H, 5.31; N, 6.21.

EXAMPLE 36 cis-6-[2-(4-Fluorobenzamido)ethyl]-4,5,6,7-tetrahydro-5,7-dimethyl-thieno[2,3-c]pyridine Prepared by Method A using the amine 9h-cis (Table VI) and 4-fluorobenzoyl chloride. The title compound was isolated in 64% yield after recrystallization from $CH_2Cl_2$/hexane (off-white solid); mp 110°–113.5° C.; IR (KBr) 3360, 2970, 1630, 1550, 1500, 1260 and 11 30 cm$^{-1}$.

Anal. Calc'd for $C_{18}H_{21}FN_2OS$: C, 65.04; H, 6.37; N, 8.43. Found: C, 65.13; H, 6.45; N, 8.23.

EXAMPLE 37 cis-6-[2-(3-Fluorobenzamido)ethyl]-4,5,6,7-tetrahydro-5,7-dimethyl-thieno[2,3-c]pyridine Hydrochloride Prepared by Method A using the amine 9h-cis (Table VI) and 3-fluorobenzoyl chloride. The title compound was isolated in 100% yield. This orange oil was treated with HCl/2-propanol (1.1 eq) to afford a white solid; mp 198°–200.5° C.; IR (KBr) 3250, 2450, 1650, 1540 and 720 cm$^{-1}$.

Anal. Calc'd for $C_{18}H_{21}FN_2OS \cdot HCl$: C, 58.61; H, 6.01; N, 7.59. Found: C, 58.77; H, 6.32; N, 7.41.

EXAMPLE 38 cis-6-[2-(2-Fluorobenzamido)ethyl]-4,5,6,7-tetrahydro-5,7-dimethyl-thieno[2,3-c]pyridine Monooxalate Prepared by Method A using the amine 9h-cis (Table VI) and 2-fluorobenzoyl chloride. The title compound was isolated in 91% yield. This material was treated with oxalic acid (1.1 eq) in acetone/ether to afford a white solid; mp 193°–296° C.; IR (KBr) 3200, 1720, 1620, 1310 and 1220 cm$^{-1}$.

Anal. Calc'd for $C_{18}H_{21}FN_2OS \cdot C_2H_2O_4$: C, 56.86; H, 5.49; N, 6.63. Found: C, 56.62; H, 5.45; N, 6.44.

EXAMPLE 39 cis-4,5,6,7-Tetrahydro-6-[2-(4-methoxybenzamido)ethyl]-5,7-dimethylthieno[2,3-c]pyridine Monooxalate Prepared by Method A using the amine 9h-cis (Table VI) and p-anisoyl chloride. The title compound was isolated in 100% yield. This material was treated with oxalic acid (1.1 eq) in acetone/ether to afford a white solid; mp 182.5°–184.5° C.; IR (KBr) 3300, 2990, 1720, 1630, 1310, 1180 and 740 cm$^{-1}$.

Anal. Calc'd for $C_{19}H_{24}N_2O_2S \cdot C_2H_2O_4$: C, 58.05; H, 6.03; N, 6.45. Found: C, 58.01; H, 6.14; N, 6.32.

EXAMPLE 40 cis-4,5,6,7-Tetrahydro-6-[2-(3-methoxybenzamido)ethyl]-5,7-dimethylthienb[2,3-c]pyridine Monooxalate Prepared by Method A using the amine 9h-cis (Table VI) and m-anisoyl chloride. The title compound was isolated in 69% yield. This material was treated with oxalic acid (1.1 eq) in acetone/ether to afford a white solid; mp 124°–128° C.; IR (KBr) 3300, 2940, 1710, 1610, 1290 and 1180 cm$^{-1}$.

Anal. Calc'd for $C_{19}H_{24}N_2O_2S \cdot C_2H_2O_4$: C, 58.05; H, 6.03; N, 6.45. Found: C, 58.02; H, 6.22; N, 6.29.

EXAMPLE 41 cis-4,5,6,7-Tetrahydro-6-[2-(2-methoxybenzamido)ethyl]-5,7-dimethylthieno[2,3-c]pyridine Monooxalate Prepared by Method A using the amine 9h-cis (Table VI) and o-anisoyl chloride. The title compound was isolated in 100% yield. This material was treated with oxalic acid (1.1 eq) in acetone/ether to afford a white solid; mp 162°–164° C.; IR (KBr) 3480, 2940, 1710, 1640, 1230 and 740 cm$^{-1}$.

Anal. Calc'd for $C_{19}H_{24}N_2O_2S \cdot C_2H_2O_4$: C, 58.05; H, 6.03; N, 6.45. Found: C, 57.91; H, 5.96; N, 6.29.

EXAMPLE 42 cis-4,5,6,7-Tetrahydro-5,7-dimethyl-6-[2-(4-methylbenzamido)ethyl]thieno[2,3-c]pyridine Monooxalate Prepared by Method A using the amine 9h-cis (Table VI) and p-toluoyl chloride. The title compound was isolated in 84% yield. This material was treated with oxalic acid (1.1 eq) in acetone to afford an off-white solid; mp 137°–141° C.; IR (KBr) 3280, 2960, 2600, 1720, 1630, 1530, 1300 and 1180 cm$^{-1}$.

Anal. Calc'd for $C_{19}H_{24}N_2OS \cdot C_2H_2O_4$: C, 60.28; H, 6.26; N, 6.69. Found: C, 60.09; H, 6.42; N, 6.47.

EXAMPLE 43 cis-6-[2-(4-Trifluoromethylbenzamido)ethyl]-4,5,6,7-tetrahydro-5,7-dimethylthieno[2,3-c]pyridine Prepared by Method A using the amine 9h-cis (Table VI) and 4-(trifluoromethyl)benzoyl chloride. The title compound was isolated in 66% yield after silica gel column chromatography and recrystallized from $CH_2Cl_2$/ether/hexane. The material was isolated as an off-white solid; mp 88°–91° C.; IR (KBr) 3280, 2960, 2600, 1720, 1630, 1530, 1300 and 1180 cm$^{-1}$.

Anal. Calc'd for $C_{19}H_{21}F_3N_2OS$: C, 59.68; H, 5.54; N, 7.33. Found: C, 59.66; H, 5.49; N, 7.29.

EXAMPLE 44 cis-6-[2-(4-Cyanobenzamido)ethyl]-4,5,6,7-tetrahydro-5,7-dimethyl-thieno[2,3-c]pyridine Prepared by Method A using the amine 9h-cis (Table VI) and 4-cyanobenzoyl chloride. The title compound was isolated in 33% yield after silica gel column chromatography and recrystallized from $CH_2Cl_2$/ether/hexane. The material was isolated as a tan solid; mp 122.5°–124.5° C.; IR (KBr) 3380, 2980, 1640, 1550, 1500, 1300 and 1150 cm$^{-1}$.

Anal. Calc'd for $C_{19}H_{21}N_3OS$: C, 67.24; H, 6.24; N, 12.38. Found: C, 67.10; H, 6.31; N, 12.31.

EXAMPLE 45 trans-6-[2-(4-Cyanobenzamido)ethyl]-4,5,6,7-tetrahydro-5,7-dimethyl-thieno[2,3-c]pyridine Hydrochloride Prepared by Method A using the amine 9h-trans (Table VII) and 4-cyanobenzoyl chloride. The title compound was isolated in 10% yield. This material was treated with HCl/2-propanol (1.1 eq) to afford an off-white solid; mp 248°–251° C.; IR (KBr) 3260, 3060, 2600, 1660, 1540 and 1300 cm$^{-1}$.

Anal. Calc'd for $C_{19}H_{21}N_3OS \cdot HCl$: C, 60.71; H, 5.90; N, 11.18. Found: C, 60.51; H, 6.07; N, 10.91.

EXAMPLE 46 cis-4,5,6,7-Tetrahydro-5,7-dimethyl-6-[2-(4-methylcarboxylbenzamido)ethyl]thieno[2,3-c]pyridine Prepared by Method A using the amine 9h-cis (Table VI) and 4-carbomethoxybenzoyl chloride. The title compound was isolated in 83% yield. This material was recrystallized from $CH_2Cl_2$/ether/hexane to afford an off-white solid; mp 106°–109° C.; IR (KBr) 3420, 2600, 1720, 1630, 1540, 1440 and 1280 cm$^{-1}$.

Anal. Calc'd for $C_{20}H_{24}N_2O_3S$: C, 64.50; H, 6.50; N, 7.52. Found: C, 64.05; H, 6.34; N, 7.53.

EXAMPLE 47

4-Aminocarbonyl-[2-(cis-4,5,6,7-tetrahydro-5,7-dimethylthieno[2,3-c]pyridin-6-yl)-N-ethyl]benzoic acid An ethanol (100 mL) solution of the ester from Example 46 (4.62 g, 12 mmol) was treated with 2N NaOH (50 mL, 100 mmol). The solution was stirred at rt for 16 hours and then treated with 2N HCl until a pH of 6–7 was reached. The ethanol/water was removed in vacuo and the residue was slurried in absolute ethanol. The NaCl was removed and the filtrate was condensed in vacuo to afford the title compound (3.70g, 83%). This material was recrystallized from ethanol/ether to afford an off-white solid; mp 182°–189° C.; IR (KBr) 3320, 2970, 1655, 1535, 1320, 1300, 1015, 825, 740 and 725 cm$^{-1}$.

Anal. Calc'd for $C_{19}H_{22}N_2O_3S$: C, 63.67; H, 6.19; N, 7.82. Found: C, 63.39; H, 6.31; N, 7.60.

EXAMPLE 48 cis-4,5,6,7-Tetrahydro-5,7-dimethyl-6-[2-(4-sulfonamidobenzamido)-ethyl]thieno[2,3-c]pyridine A toluene solution (30 mL) of the amine 9h-cis (Table VI) (0.75 g, 3.57 mmol) at 0° C. under nitrogen was treated with a 2M trimethylaluminum in toluene solution (2 mL, 4 mmol). This solution was allowed to warm to rt and then it was treated portionwise with methyl 4-(aminosulfonyl)benzoate (0.84 g, 3.92 mmol). The solution was warmed to 50° C. for 6 hours and then it was quenched with water. The reaction mixture was extracted with EtOAc and the combined organic extract was washed with brine and dried (MgSO$_4$). Solvent removal produced the crude product that was purified by flash silica gel column chromatography using 0.5–5% MeOH in CH$_2$Cl$_2$ and NH$_4$OH/MeOH (0.5/4.5%) in CH$_2$Cl$_2$. The title compound was isolated and recrystallized from MeOH/CH$_2$Cl$_2$ to afford a white solid (0.53 g, 37%); mp 186°–188° C.; IR (KBr) 3440, 2980, 1640, 1550, 1330, 1160 and 730 cm$^{-1}$.

Anal. Calc'd for $C_{18}H_{23}N_3O_3S_2 \cdot \frac{1}{4}H_2O$: C, 54.33; H, 5.95; N, 10.56. Found: C, 54.32; H, 6.02; N, 10.34.

EXAMPLE 49 cis-6-[2-[4-(N,N-Diethylaminosulfonylbenzamido)ethyl]-4,5,6,7-tetrahydro-5,7-dimethylthieno[2,3-c]pyridine Hydrochloride A CH$_2$Cl$_2$ solution of 4-carboxy-N,N-diethylbenzenesulfonamide (2.78 g, 11mmol) at −10° C. under nitrogen was treated sequentially with a CH$_2$Cl$_2$ solution of TEA (1.66 mL, 12 mmol), a CH$_2$Cl$_2$ solution of isobutylchloroformate (1.54 mL, 12 mmol) and a CH$_2$Cl$_2$ solution of amine 9h-cis (Table VI) (2.5 g, 12 mmol). The mixture was allowed to warm to rt and then it was quenched with saturated NaHCO$_3$ solution. The aqueous phase was extracted with CH$_2$Cl$_2$ and the combined organic extract was washed with brine and dried (MgSO$_4$). Solvent removal produced the crude product that was purified by flash silica gel chromatography using 1–3.5% MeOH in CH$_2$Cl$_2$. The title compound was isolated (1.73 g, 21 %) and treated with HCl/2-propanol (1.1 eq) to afford a white solid; mp 111°–115° C.; IR (KBr) 3220, 2920, 2880, 2430, 1640, 1510, 1310, 1120, 995, 910 and 705 cm$^{-1}$.

Anal. Calc'd for $C_{22}H_{31}N_3O_3S_2 \cdot HCl$: C, 54.37; H, 6.64; N, 8.65. Found: C, 54.03; H, 6.87; N, 8.20.

EXAMPLE 50 cis-4,5,6,7-Tetrahydro-6-[2-(4-methanesulfonylbenzamido)ethyl]5,7-dimethylthieno[2,3-c]pyridine Hydrochloride The title compound was prepared in 77% yield by the same procedure as in Example 49 starting with 4-(methylsulfonyl)benzoic acid (2.16 g, 11 mmol) and the amine 9h-cis (Table VI) (2.5 g, 12 mmol). The product was treated with HCl/2-propanol (1.1 eq) to afford a white solid; mp 191.5°–194° C.; IR (KBr) 3320, 2980, 2420, 1655, 1535, 1300, 1150, 785, 760 and 745 cm$^{-1}$.

Anal. Calc'd for $C_{19}H_{24}N_2O_3S_2 \cdot HCl$: C, 53.21; H, 5.88; N, 6.53. Found: C, 53.05; H, 5.83; N, 6.32.

EXAMPLE 51 cis-6-[2-(2,4-Difluorobenzamido)ethyl]-4,5,6,7-tetrahydro-5,7-dimethylthieno[2,3-c]pyridine Monooxalate Prepared by Method A using the amine 9h-trans (Table VII) and 2,4-difluorobenzoyl chloride. The title compound was isolated in 100% yield. This material was treated with oxalic acid (1.1 eq) in acetone/ether to afford a white solid; mp 213.5°–216.5° C.; IR (KBr) 3220, 1720, 1620, 1190 and 740 cm$^{-1}$.

Anal. Calc'd for $C_{18}H_{20}F_2N_2OS \cdot C_2H_2O_4$: C, 54.54; H, 5.04; N, 6.36. Found: C, 54.16; H, 5.10; N, 5.94.

EXAMPLE 52 cis-6-[2-(3,4-Dichlorobenzamido)ethyl]-4,5,6,7-tetrahydro-5,7-dimethylthieno[2,3-c]pyridine Monooxalate Prepared by Method A using the amine 9h-cis (Table VI) and 3,4-dichlorobenzoyl chloride. The title compound was isolated in 100% yield. This material was treated with oxalic acid (1.1 eq) in acetone to afford a tan solid; mp 164°–167° C.; IR (KBr) 3300, 3000, 1720, 1640, 1520, 1300 and 1200 cm$^{-1}$.

Anal. Calc'd for $C_{18}H_{20}Cl_2N_2OS \cdot C_2H_2O_4$: C, 50.75; H, 4.69; N, 5.92. Found: C, 50.73; H, 4.72; N, 5.76.

EXAMPLE 53 cis-6-[2-(2,3,4,5,6-Pentafluorobenzamido)ethyl]-4,5,6,7-tetrahydro-5,7-dimethylthieno[2,3-c]pyridine Prepared by Method A using the amine 9h-cis (Table VI) and 2,3,4,5,6-pentafluorobenzoyl chloride. The title compound was isolated in yield. This material was recrystallized from ether/hexane to afford a light yellow solid; mp 116°–119° C.; IR (KBr) 3300, 2960, 1650, 1500, 1320 and 980 cm$^{-1}$.

Anal. Calc'd for $C_{18}H_{17}F_5N_2OS$: C, 53.47; H, 4.24; N, 6.93. Found: C, 53.48; H, 4.10; N, 6.79.

EXAMPLE 54 cis-4,5,6,7-Tetrahydro-6-[2-(pyridine-2-carboxamido)ethyl]-5,7-dimethylthieno[2,3-c]pyridine Prepared by Method A using the amine 9h-cis (Table VI) and picolinoyl chloride. The title compound was isolated in 57% yield. This material was recrystallized from ether/hexane to afford a tan solid; mp 116°–119.5° C.; IR (KBr) 3280, 2920, 1630, 1510, 1440, 1210 and 1130 cm$^{-1}$.

Anal. Calc'd for $C_{17}H_{21}N_3OS$: C, 64.74; H, 6.71; N, 13.33. Found: C, 64.64; H, 6.76; N, 13.27.

EXAMPLE 55 cis-4,5,6,7-Tetrahydro-6-[2-(pyridine-3-carboxamido)ethyl]5,7-dimethylthieno[2,3-c]pyridine Monooxalate Prepared by Method A using the amine 9h-cis (Table VI) and nicotinoyl chloride. The title compound was isolated in 96% yield. This material was treated with oxalic acid (1.1 eq) in MeOH/hexane to afford a tan solid; mp 194°–196.5° C.; IR (KBr) 3220, 1710, 1610, 1520, 1420, 1300 and 1180 cm$^{-1}$.

Anal. Calc'd for $C_{17}H_{21}N_3OS \cdot C_2H_2O_4$: C, 56.29; H, 5.72; N, 10.37. Found: C, 56.41; H, 5.66; N, 10.48.

EXAMPLE 56 cis-4,5,6,7-Tetrahydro-6-[2-(pyridine-4-carboxamido)ethyl]-5,7-dimethylthieno[2,3-c]pyridine Monooxalate Prepared by Method A using the amine 9h-cis (Table VI) and isonicotinoyl chloride. The title compound was isolated in 99% yield. This material was treated with oxalic acid (1.1 eq) in acetone to afford a white solid; mp 187°–189° C.; IR (KBr) 3280, 3000, 1720, 1620, 1540, 1310 and 1190 cm$^{-1}$.

Anal. Calc'd for $C_{17}H_{21}N_3OS \cdot C_2H_2O_4 \cdot \frac{1}{4}H_2O$: C, 55.67; H, 5.78; N, 10.25. Found: C, 55.22; H, 5.72; N, 9.81.

EXAMPLE 57 cis-4,5,6,7-Tetrahydro-5,7-dimethyl-6-[2-(2-thiophenecarboxamido)ethyl]thieno[2,3-c]pyridine Prepared by Method A using the amine 9h-cis (Table VI) and 2-thiophenecarbonyl chloride. The title compound was isolated in 100% yield. This material was recrystallized from $CH_2Cl_2$/ether/hexane to afford a yellow solid; mp 111°–113° C.; IR (KBr) 3230, 2860, 1610, 1550, 1330, 1140 and 740 cm$^{-1}$.

Anal. Calc'd for $C_{16}H_{20}N_2OS_2$: C, 59.98; H, 6.29; N, 8.75. Found: C, 59.56; H, 6.29; N, 8.75.

EXAMPLE 58 cis-4,5,6,7-Tetrahydro-5,7-dimethyl-6-[2-(5-nitrothiophene-2-carboxamido)ethyl]thieno[2,3-c]pyridine Hydrochloride Prepared by Method A using the amine 9h-cis (Table VI) and 5-nitro-2-thiophenecarbonyl chloride. The title compound was isolated in 99% yield. This material was treated with HCl/2-propanol to afford a tan solid; mp 246°–248° C.; IR (KBr) 3200, 3080, 2490, 1660, 1560, 1500, 1340, 1290 and 730 cm$^{-1}$.

Anal. Calc'd for $C_{16}H_{19}N_3O_3S_2 \cdot HCl$: C, 47.82; H, 5.02; N, 10.46. Found: C, 47.79; H, 5.01; N, 10.31.

EXAMPLE 59 cis-4,5,6,7-Tetrahydro-6-[2-[4-[(imidazo-1-yl)methyl]-benzamidoethyl-5,7-dimethylthieno[2,3-c]pyridine The title compound was prepared in 39% yield by the same procedure as in Example 48 starting with methyl 4-[(imidazol-1-yl)methyl)benzoate [prepared by reacting an acetonitrile solution (20 mL) of methyl 4-bromomethylbenzoate (10 mmol) with imidazole (20 mmol) at reflux for 2 hours. The product was isolated (55% yield) as a white crystalline solid after silica gel column chromatography using 1–3% EtOH in EtOAc. A portion of this material was recrystallized from EtOAc/hexane/ether; mp 75°–78° C.; IR (KBr) 1705, 1500, 1300, 1275, 1225, 1100, 1075 and 725; Anal. Calc'd for $C_{12}H_{12}N_2O_2$: C, 66.65; H, 5.59; N, 12.96. Found: C, 66.66; H, 5.43; N, 13.13] (1.08 g, 5 mmol) and the amine 9h-cis (Table VI) (1.1 g, 5.24 mmol). The product was recrystallized from EtOAc/EtOH/ether to afford a light pink solid; mp 127°–131° C.; IR (KBr) 3230, 1640, 1550, 1550, 1295, 1235, 1080, 910, 720, 685 and 665 cm$^{-1}$.

Anal. Calc'd for $C_{22}H_{26}N_3OS$: C, 66.97; H, 6.64; N, 14.20. Found: C, 66.93; H, 6.45; N, 14.12.

EXAMPLE 60

Diethyl cis-4,5,6,7-tetrahydro-5,7-dimethyl-6-[2-(4-phosphonomethylbenzamido)ethyl]thieno[2,3-c]pyridine The title compound was prepared in 56% yield by the same procedure as in Example 48 starting with diethyl 4-carboxymethylbenzylphosphonate prepared by reacting a toluene solution (60 mL) of methyl 4-bromomethylbenzoate (10 mmol) with triethyl phosphite (25 mmol) at reflux for hours. The product was isolated (98% yield) as a clear liquid after silica gel column chromatography using 50–100% EtOAc in hexane; MH+ at m/z 287] (2.43 g, 8.5 mmol) and the amine 9h-cis (Table VI) (2.1 g, 10 mmol). The product was isolated as a brown waxy solid; IR (neat) 3060, 2990, 1660, 1650, 1260, 1050, 1025 and 740 cm$^{-1}$.

Anal. Calc'd for $C_{23}H_{33}N_2O_4PS$: C, 59.46; H, 7.16; N, 6.03. Found: C, 59.73; H, 7.19; N, 5.84.

EXAMPLE 61 cis-4,5,6,7-Tetrahydro-6-[2-(4-methanesulfonylmethylbenzamido)ethyl]thieno[2,3-c]pyridine The title compound was prepared in 66% yield by the same procedure as in Example 48 starting with methyl 4-(methanesulfonylmethyl)benzoate (1.94 g, 8.5 mmol) and the amine 9h-cis (Table VI) (2.1 g, 10 mmol). The product was recrystallized from $CH_2Cl_2$/MeOH/ether to afford a white solid; mp 170°–172° C.; IR (KBr) 3410, 2970, 2930, 1645, 1540, 1500, 1295, 1120 and cm$^{-1}$.

Anal. Calc'd for $C_{20}H_{26}N_2O_3S_2$: C, 59-08; H, 6.45; N, 6.89. Found: C, 58.88; H, 6.30; N, 6.71.

EXAMPLE 62 cis-4,5,6,7-Tetrahydro-6-[2-[4-(imidazo-1-yl)benzamido]ethyl]-5,7-dimethylthieno[2,3-c]pyridine Dihydrochloride The title compound was prepared in 31 % yield by the same procedure as in Example 48 starting with ethyl 4-(imidazo-1 -yl)benzoate [prepared by reacting a DMSO mixture (20 mL) of hexane washed 60% NaH in mineral oil (1 g, 25 mmol) with imidazole (1.63 g, 24 mmol) and then with ethyl 4-fluorobenzoate (3.36 g, 20 mmol) under nitrogen at 100° C. for 18 hours. The reaction solution was quenched with water/ice and the solid was collected, washed with water and dried to afford a light pink solid (2.7 g, 63%); MH+ at m/z 217; IR (KBr) 3130, 1695, 1610, 1525, 1285, 1265, 1060, 850, 765, and cm$^{-1}$] (1.84 g, 8.5 mmol) and the amine 9h-cis (Table VI) (2.1 g, 10 mmol). The product was isolated and treated with HCl/2-propanol (>2 eq) to afford a light gray solid; mp 216°–226° C.; IR (KBr) 2611, 1661, 1610, 1539, 1507 and 1301 cm$^{-1}$.

Anal. Calc'd for $C_{21}H_{24}N_4OS \cdot 2HCl \cdot \frac{1}{2}H_2O$: C, 54.54; H, 5.89; N, 12.12. Found: C, 54.60; H, 5.81; N, 11.94.

EXAMPLE 63 cis-4,5,6,7-Tetrahydro-5,7-dimethyl-6-[2-(4-nitrophenylsulfonamido)ethyl]thieno[2,3-c]pyridine Prepared by Method A using the amine 9h-cis (Table VI) and 4-nitrobenzenesulfonyl chloride. The title compound was isolated in 30% yield after silica gel column chromatography and recrystallization from $CH_2Cl_2$/ether/hexane. The title compound was isolated as an off-white solid; mp 116°–119° C.; IR (KBr) 3000, 1560, 1350, 1310, 1160, 1100 and 860 cm$^{-1}$.

Anal. Calc'd for $C_{17}H_{21}N_3O_4S_2$: C, 51.64; H, 5.35; N, 10.63. Found: C, 51.70; H, 5.09; N, 10.24.

EXAMPLE 64 trans-4,5,6,7-Tetrahydro-5,7-dimethyl-6-[2-(4-nitrophenylsulfonamido)ethyl]thieno[2,3-c]pyridine Prepared by Method A using the amine 9h-trans(Table VII) and 4-nitrobenzenesulfonyl chloride. The title compound was isolated in 70% yield after silica gel column chromatography and recrystallization from $CH_2Cl_2$/ether. The title compound was isolated as a light green solid; mp 132°-135.5° C.; IR (KBr) 3320, 2980, 1530, 1350, 1160, and 1090 cm$^{-1}$.

Anal. Calc'd for $C_{17}H_{21}N_3O_4S_2$: C, 51.64; H, 5.35; N, 10.63. Found: C, 51.55; H, 4.91; N, 10.32.

EXAMPLE 65 cis-4,5,6,7-Tetrahydro-5,7-dimethyl-6-[2-(2-nitrophenylsulfonamido)ethyl]thieno[2,3-c]pyridine Hydrochloride Prepared by Method A using the amine 9h-cis (Table VI) and 2-nitrobenzenesulfonyl chloride. The title compound was isolated in 87% yield. The title compound was treated with HCl/2-propanol (1.1 eq) to produce a light green solid. This material was used directly in the subsequent reduction step (Example 106).

EXAMPLE 66 cis-6-[2-(4-Chlorobenzenesulfonamido)ethyl]-4,5,6,7-tetrahydro-5,7-dimethylthieno[2,3-c]pyridine Hydrochloride Prepared by Method A using the amine 9h-cis (Table VI) and 4-chlorobenzenesulfonyl chloride. The title compound was isolated in 80% yield. This material was treated with HCl/2-propanol to afford a white solid; mp 111°-114° C.; IR (KBr) 3100, 2990, 1580, 1350, 1170, 1100 and 770 cm$^{-1}$.

Anal. Calc'd for $C_{17}H_{21}ClN_2O_2S_2 \cdot HCl$: C, 48.46; H, 5.26; N, 6.65. Found: C, 48.41; H, 5.22; N, 6.61.

EXAMPLE 67 cis-4,5,6,7-Tetrahydro-5,7-dimethyl-6-[2-(4-nitrobenzylamino)ethyl]thieno[2,3-c]pyridine 3/2 Oxalate A borane/THF (48 ml, 48 mmol) solution of the amide from Example 28 (3.50 g, 9.74 mmol) was stirred at reflux for 12 hours under nitrogen. After the solution was quenched with 6N HCl, the THF was removed in vacuo. The acidic residue was warmed on a steambath for 15-20 min and then it was treated with 50% NaOH to afford a pH of 10. The aqueous mixture was extracted with $CH_2Cl_2$ and the combined extract was washed with brine and dried ($Na_2SO_4$). Solvent removal produced the crude product that was purified by flash silica gel column chromatography using 0.5-4% MeOH in $CH_2Cl_2$. There was obtained 1.96 g (58%) of the title compound that was treated with oxalic acid (1.1 eq) in acetone to produce a tan solid: mp 211°- 213° C.; IR (KBr) 3040, 2840, 1720, 1625, 1520, 1345, 1210, 855, 715 and 700 cm$^{-1}$.

Anal. Calc'd for $C_{18}H_{23}N_3O_2S \cdot 3/2C_2H_2O_4$: C, 52.50; H, 5.45; N, 8.74. Found: C, 52.81; H, 5.11; N, 8.45.

EXAMPLE 68

2-[3-(cis-4,5,6,7-Tetrahydro-5,7-dimethylthieno[2,3-c]pyridin-6yl)propyl]-1H-isoindole-1,3-dione 3/2 Oxalate A mixture of amine 7h-cis (Table II) (8.14 g, 40 mmol), N-(3-bromopropyl)-phthalimide (13.1 g, 48 mmol), $K_2CO_3$ (27.6 g, 0.2 mol) and NaI (8.4 g, 56 mmol) in acetonitrile (120 mL) was warmed to reflux for 16 hours under nitrogen. The solids were removed and washed with acetonitrile. The combined filtrate was condensed under vacuum and the residue (20.6 g) was purified by flash silica gel chromatography using 5-15% ether in $CH_2Cl_2$. The title compound was obtained as a dark oily material (9.8 g, 69%). A portion of this material was dissolved in acetone and treated with oxalic acid (1.1 eq) to produce a gray solid; mp 167°-169° C. (dec); IR (KBr) 1765, 1705, 1390, 1360 and 715 cm$^{-1}$.

Anal. Calc'd for $C_{20}H_{22}N_2O_2S \cdot 3/2C_2H_2O_4$: C, 56.43; H, 5.15; N, 5.72. Found: C, 56.46; H, 5.22; N, 5.66.

EXAMPLE 69 cis-4,5,6,7-Tetrahydro-5,7-dimethyl-6-[3-(4-nitrobenzamido)propyl]thieno[2,3-c]pyridine The amine 9q-cis (Table VI) was prepared by treating the isoindole of Example 68 (3.3 g, 9.32 mmol) with hydrazine hydrate (1 mL, 18.6 mmol) in absolute EtOH (45 mL). This mixture was warmed to reflux for 20 hours and then the EtOH was removed in vacuo. The white residue was leached with $CH_2Cl_2$ and $CHCl_3$. The combined filtrate was condensed in vacuo to afford the amine 9q-cis described in Table VI.

The title compound was prepared by Method A using the above amine and 4-nitrobenzoyl chloride. The desired product was obtained in 72% yield and it was crystallized from ether/$CH_2Cl_2$ to afford a bright yellow solid; mp 114°-116.5° C.; IR (KBr) 3300, 2960, 16253 1595, 1535, 1520, 1345, 865, 840, 695 and 670 cm$^{-1}$.

Anal. Calc'd for $C_{19}H_{23}N_3O_3S$: C, 61.10; H, 6.21; N, 11.25. Found: C, 60.76; H, 6.47; N, 11.28.

EXAMPLE 70 cis-4,5,6,7-Tetrahydro-5,7-dimethyl-6-[3-(4-nitrophenylsulfonamido)propyl]thieno[2,3-c]pyridine Prepared by Method A using the amine 9q-cis (Table VI) and 4-nitrobenzenesulfonyl chloride. The title compound was isolated in 81% yield after silica gel column chromatography (50-100% EtOH in hexane) and recrystallization from EtOAc/MeOH. The title compound was isolated as a light olive green solid; mp 70-75 (softens) 93°-98° C.; IR (KBr) 3300, 3110, 2970, 1530, 1350, 1165, 740 and 615 cm$^{-1}$.

Anal. Calc'd for $C_{18}H_{23}N_3O_4S_2$: C, 52.79; H, 5.66; N, 10.26. Found: C, 52.47; H, 5.78; N, 10.03.

EXAMPLE 71

2-[4-(cis-4,5,6,7-Tetrahydro-5,7-dimethylthieno[2,3-c]pyridin-6-yl)butyl]-1 H-isoindole-1,3-dione The title compound was prepared in a similar fashion as described in Example 68 starting with the amine 7h-cis (Table II) and N-(4-bromobutyl)phthalimide in DMF at 70° C. for 24 hours. The desired product was obtained as a yellow solid (65%) and crystallized from CH$_2$Cl$_2$/ether/hexane; mp 96°-98° C.; IR (KBr) 2950, 1770, 1710,1400, 1200, 1050 and 740 cm$^{-1}$.

Anal. Calc'd for C$_{21}$H$_{24}$N$_2$O$_2$S: C, 68.46; H, 6.57; N, 7.60. Found: C, 68.54; H, 6.60; N, 7.59.

EXAMPLE 72 cis-4,5,6,7-Tetrahydro-5,7-dimethyl-6-[4-(4-nitrobenzamido)butyl]thieno[2,3-c]pyridine Monooxalate The amine 9r-cis (Table VI) was prepared in the same fashion as described for amine 9q-cis in Example 70.

The title compound was prepared by Method A using the amine 9r-cis and 4-nitrobenzoyl chloride. The desired product was obtained in 80% yield. This material was treated with oxalic acid (1.1 eq) in acetone to afford a tan solid; mp 127.5°-132° C.; IR (KBr) 3340, 2960, 2620, 1700, 1650, 1600, 1520 and 1350 cm$^{-1}$.

Anal. Calc'd for C$_{20}$H$_{25}$N$_3$O$_3$S.C$_2$H$_2$O$_4$: C, 55.34; H, 5.70; N, 8.80. Found: C, 55.39; H, 5.74; N, 8.51.

EXAMPLE 73 cis-4,5,6,7-Tetrahydro-5,7.dimethyl-6-[4-(4-nitrobenzenesulfonamido)butyl]thieno[2,3-c]pyridine Hydrochloride The title compound was prepared by Method A using the amine 9r-cis and 4-nitrobenzenesulfonyl chloride. The desired product was obtained in 73% yield. This material was treated with HCl/2-propanol (1.1 eq) in EtOH/hexane to afford a light yellow solid; mp 134°-137.5° C.; IR (KBr) 3410, 2600, 1525, 1350, 1165, 1095, 735 and 610 cm$^{-1}$.

Anal. Calc'd for C$_{19}$H$_{25}$N$_3$O$_4$S$_2$.HCl.½C$_2$H$_5$OH: C, 49.74; H, 6.05; N, 8.70. Found: C, 49.54; H, 6.03; N, 8.65.

EXAMPLE 74

4-(4,5,6,7-Tetrahydrothieno[2,3-c]pyridin-6-yl)-1-(4-nitrobenzoyl)piperidine Hydrochloride The title compound was prepared by the following multistep synthesis.

1-Carbethoxy-4-[2-(thien-3-yl)ethylamino]piperidine Hydrochloride

A methanol solution (100 mL) of 3-(2-aminoethyl)thiophene hydrochloride (8.18 g, 50 mmol) was treated with NaOAc (8.2 g, 0.1 mol) and 1-carbethoxy-4-piperidone (12.8 g, 75 mmol) at rt under nitrogen. After stirring for 1 hour, the solution was treated with NaCNBH$_3$ and the mixture was stirred at rt for 18 hours. This mixture was carefully quenched with 6N HCl, warmed on a steambath for 30 min and then the MeOH was removed in vacuo. The aqueous residue was treated with 2N NaOH until a pH of 12 and then it was extracted with CH$_2$Cl$_2$. The combined extract was washed with brine and dried (Na$_2$SO$_4$). Solvent removal produced the crude product that was treated with HCl/2-propanol to afford the hydrochloride salt (12.3 g, 77%) as a beige solid; 199°-201° C.; IR (KBr) 2945, 2680, 2640, 2480, 1695, 1465, 1435, 1240, 785 and 770 cm$^{-1}$.

Anal. Calc'd for C$_{14}$H$_{22}$N$_2$O$_2$S.HCl: C, 52.73; H, 7.27; N, 8.79. Found: C, 52.71; H, 7.40; N, 8.76.

6-(1 -Carbethoxylpiperidin-4-yl)-4.5.6.7-tetrahydrothieno[2,3-c]pyridine Hydrochloride A glacial acetic acid solution (60 mL) of the above compound (3.18 g, 10 mmol), NaOAc (0.82 g, 10 mmol) and formaldehyde (37 wt % solution in water) (10.5 g, 130 mmol) was placed in a 50° C. oil bath for 8 hours. The solvents were removed in vacuo and the residue was treated with 2N NaOH until a pH of 10 was reached. This aqueous mixture was extracted with CH$_2$Cl$_2$ and the combined extract was dried (MgSO$_4$). Solvent removal produced the crude product that was treated with HCl/2-propanol (1.1 eq). There was obtained a white solid (3.0 g, 91 %); mp 248.5°-250° C.; IR (KBr) 2949,2918,2509,1688,1474;1445,1434,1253,1233,1140,10-56,875, 765 and 715 cm$^{-1}$.

Anal. Calc'd for C$_{15}$H$_{22}$N$_2$O$_2$S.HCl: C, 54.45; H, 7.01; N, 8.47. Found: C, 54.45; H, 7.18; N, 8.33.

4.5.6.7-Tetrahydro-6-(piperidin-4-yl)thieno[2,3-c]pyridine Hydrochloride

A glacial acetic acid solution (10 mL) of the above compound (2.0 g, 6.0 mmol) was treated with concentrated HCl (30 mL) and warmed to reflux for 20 hours. The solution was poured into ice-water and treated with 50% NaOH until a pH of 12 was reached. This aqueous mixture was extracted with CH$_2$Cl$_2$ and the combined extract was washed with brine and dried (MgSO$_4$). Solvent removal produced the amine product (1.4 g, 100%) as a brown oily material; MH+ at m/z 223; IR (neat) 2930, 2800, 1445, 1375, 1320, 1155, 1140, 1050, 890 and 700 cm$^{-1}$.

The title compound was prepared by Method A using the above amine and 4-nitrobenzoyl chloride. The desired product was obtained in 82% yield. This material was treated with HCl/2-propanol (1.1 eq) to afford a white solid; mp 252°-254° C.; IR (KBr) 2920, 2480, 2390, 1625, 1600, 1515, 1435, 1350, 1100, 1000, 850 and 720 cm$^{-1}$.

Anal. Calc'd for C$_{19}$H$_{21}$N$_3$O$_3$S.HCl: C, 55.94; H, 5.44; N, 10.30. Found: C, 55.81; H, 5.40; N, 9.98.

EXAMPLE 75 cis-2-Chloro-4,5,6,7-tetrahydro-5,7-dimethyl-6-[2-(4-nitrobenzamido)ethyl]thieno[2,3-c]pyridine Hydrochloride A CH$_2$Cl$_2$/AcOH (20 mL40 mL) solution of the thiophene compound in Example 28 (5.0 g, 14 mmol) at −5° C. under nitrogen was treated with sulfuryl chloride (2.24 mL, 28 mmol). The reaction was stirred at 0° C. for 1 hour and at rt for 3 hours. The reaction was quenched with saturated NaHCO$_3$ and extracted with CH$_2$Cl$_2$. The combined extract was dried (MgSO$_4$) and the solvent was removed in vacuo. The residue was purified by flash silica gel column chromatography using 0.5-1.5% MeOH in CH$_2$Cl$_2$ to afford the title compound (3.86 g, 70%). A portion of this material was isolated as its hydrochloride salt (gray solid); mp 261.5°-264° C.; IR (KBr) 3240, 2460, 1670, 1600, 1550, 1500, 1340 and 1290 cm$^{-1}$.

Anal. Calc'd for C$_{18}$H$_{20}$ClN$_3$O$_3$S.HCl: C, 50.24; H, 4.92; N, 9.76. Found: C, 50.27; H, 4.87; N, 9.45.

EXAMPLE 76 cis-2-Bromo-4,5,6,7-tetrahydro-5,7-dimethyl-6-[2-(4-nitrobenzamido)ethyl]thieno[2,3-c]pyridine Hydrochloride The thiophene compound from Example 28 (2.5 g, 6.96 mmol) was treated with bromine (0.71 mL, 14 mmol) as described for Example 75. The title compound was isolated (1.31 g, 43%) and treated with HCl/2-propanol (1.1 eq) to afford a brown solid; mp 265°-267° C.; IR (KBr) 3260 2480, 1665, 1600, 1550, 1525, 1340, 1290, 1105, 1110, 865, 855, 825 and 715 cm$^{-1}$.

Anal. Calc'd for C$_{18}$H$_{20}$BrN$_3$O$_3$S.HCl: C, 45.53; H, 4.46; N, 8.85. Found: C, 45.90; H, 4.75; N, 8.65.

EXAMPLE 77 cis-4,5,6,7-Tetrahydro-5,7-dimethyl-2-nitro-6-[2-(4-nitrobenzamido)ethyl]thieno[2,3-c]pyridine A CH$_2$Cl$_2$ (35 mi) solution of the thiophene in Example 28 (5.0 g, 14 mmol) at −10° C. under nitrogen was treated with methanesulfonic acid (70 mL) and dropwise with 70% HNO$_3$ (3.15 mL, 69 mmol). The reaction was stirred at 10° C. for 90 min and then poured onto ice water. The pH of the solution was adjusted to 9 with concentrated NH$_4$OH. This basic solution was extracted with CH$_2$Cl$_2$ and the combined extract was washed with brine and dried (MgSO$_4$). Solvent removal produced a dark brown solid (4.54 g, 81%) that was recrystallized from CH$_2$Cl$_2$/MeOH (brown solid); mp 155°–156.5° C.; IR (KBr) 3410, 3110, 2960, 1655, 1600, 1515, 1325, 1175, 865, 835 and 720 cm$^{-1}$.

Anal. Calc'd for C$_{18}$H$_{20}$N$_4$O$_5$S: C, 53.46; H, 4.99; N, 13.86. Found: C, 53.20; H, 5.04; N, 13.73.

EXAMPLE 78 cis-4,5,6,7-Tetrahydro-5,7-dimethyl-6-[2-(4-nitrophenoxy)ethyl]thieno[2,3-c]pyridine To an acetonitrile solution of amine 7h-cis hydrochloride (Table II) (3.14 g, 15.5 mmol) was added 1-(2-chloroethoxy)-4-nitrobenzene (3.67 g, 18.3 mmol), K$_2$CO$_3$ (10.5 g, 76 mmol) and NaI (3.3 g, 22 mmol). The mixture was warmed to reflux under nitrogen for 16–18 hours. After the solvent had been removed in vacuo, the oily solid was slurried in water and extracted with CH$_2$Cl$_2$. The combined CH$_2$Cl$_2$ extract was washed with water and brine and dried (Na$_2$SO$_4$). Solvent removal Produced the crude product that was purified by flash silica gel chromatography using a mixture of EtOAc in hexane to afford a solid (1.1 g, 21 %). This material was crystallized from ether/CH$_2$Cl$_2$ to produce an off-white solid; mp 94°–96° C.; IR (KBr) 3100, 3080, 3060, 2920, 1610, 1590, 1500, 1340, 1260, 1170, 1110, 1020 and 840 cm$^{-1}$.

Anal. Calc'd for C$_{17}$H$_{20}$N$_2$O$_3$S: C, 61.43; H, 6.07; N, 8.42. Found: C, 61.46; H, 6.01; N, 8.30.

EXAMPLE 79 cis-4,5,6,7-Tetrahydro-5,7-dimethyl-N-methyl-6-[2-(4-nitrobenzamido)ethyl]thieno[2,3-c]pyridine Hydrochloride A mixture of the amine 9h-cis (Table VI) (2.9 g, 13.8 mmol) and 2N NaOH (7.6 mL, 15.2 mmol) in CH$_2$Cl$_2$ (30 mL) at 0° C. was slowly treated with a CH$_2$Cl$_2$ solution of ethyl chloroformate (1.45 g, 15.2 mmol). The reaction was allowed to warm to rt and stirred for 16 hours. The aqueous phase was extracted with CH$_2$Cl$_2$ and the combined organic extract was dried (MgSO$_4$). Solvent removal produced a light brown oil (3.9 g, 100%); MH+ at m/z 283; IR (neat) 3360, 3000, 2950, 1710, 1530, 1250, 1150 and 1045 cm$^{-1}$.

The above crude urethane (3.9 g, 13.8 mmol) in THF (25 mL) was slowly added to a refluxing ether (50 mL) mixture of LAH (1.0 g, 27.6 mmol) under nitrogen. The mixture was refluxed for 4 hours and then the mixture was carefully quenched with a freshly prepared saturated Na$_2$SO$_4$ solution. The solids were removed and leached with hot THF. The combined filtrate was condensed in vacuo to produce 3.2 g of light yellow liquid that was purified by flash silica gel chromatography using 3% MeOH in CH$_2$Cl$_2$. The column was then eluted with 0.5–1% NH$_4$OH in 5–6% MeOH in CH$_2$Cl$_2$. There was obtained 2.0 g (61 %) of the desired N-methyl compound as a liquid that solidified upon standing; MH+ at m/z 225.

The title compound was prepared by Method A using the above amine and 4-nitrobenzoyl chloride. The desired product was obtained in 84% yield as a dark orange-yellow viscous liquid. This material was treated with HCl/2-propanol (1.1 eq) to afford a tan solid; mp 200.5°–203.5° C.; IR (KBr) 2380, 1635, 1520, 1345, 1080, 855 and 725 cm$^{-1}$.

Anal. Calc'd for C$_{19}$H$_{23}$N$_3$O$_3$S.HCl: C, 55.67; H, 5.90; N, 10.25. Found: C, 55.56; H, 5.94; N, 9.90.

EXAMPLE 80 cis-4,5,6,7-Tetrahydro-5,7-dimethyl-N-(1-methylethyl)-6-[2-(4-nitrobenzamido)ethyl]thieno[2,3-c]pyridine A solution of the amine 9h-cis (Table VI) (2.1 9, 10 mmol) in MeOH (225 mL) and glacial AcOH (2.25 mL) was treated with acetone (0.81 mL, 11 mmol). This solution was stirred at rt under nitrogen for 15–20 min and then treated with NaCNBH$_3$ (1.63 g, 11 mmol). This mixture was stirred at rt for 18 hours. The reaction mixture was quenched with 2N HCl and the solvent was removed in vacuo. The aqueous residue was further acidified with 6N HCl and placed on a steambath for 15–20 min. The acid solution was cooled in ice and treated with 50% NaOH to a pH of 10. The basic solution was extracted with CH$_2$Cl$_2$ and the combined extract was washed with brine and dried (Na$_2$SO$_4$). Solvent removal produced the isopropyl amine (2.4 g, 95%) as a yellow liquid; MH+ at m/z 253; IR (neat) 2980, 1470, 1375, 1180 and 710 cm$^{-1}$.

The title compound was prepared by Method A using the above amine and 4-nitrobenzoyl chloride. The desired product was obtained in 73% yield as a yellow gum that was crystallized from ether/EtOAc to afford a cream.:, colored solid; mp 117°–120° C.; IR (KBr) 1630, 1515, 1355, 1310, 865, 735 and 715 cm$^{-1}$.

Anal. Calc'd for C$_{21}$H$_{27}$N$_3$O$_3$S: C, 62.82; H, 6.78; N, 10.46. Found: C, 62.73; H, 6.75; N, 10.50.

EXAMPLE 81 cis-4,5,6,7-Tetrahydro-5,7-dimethyl-N-(1-methylethyl)-6-[2-(4-nitrophenylsulfonamido)ethyl]-thieno[2,3-c]pyridine An ice-cold CH$_2$Cl$_2$ (50 mL) solution of the isopropyl amine described in Example 80 (1.2 g, 4.76 mmol) and 4-nitrobenzenesulfonyl chloride (1.3 g, 5.24 mmol) was slowly treated with 2N NaOH over a 30 min period. The two-phase reaction was stirred at room temperature for 2 hours and the CH$_2$Cl$_2$ layer was removed, washed with water and dried (MgSO$_4$). Solvent removal produced a dark residue (1.8 g) that was purified by flash silica gel chromatography using 20–40% EtOAc in hexane. There was obtained the title compound (1.3 g, 62%) as a crystalline solid that was recrystallized from CH$_2$Cl$_2$/ether to afford a light brown solid; mp 140°–143° C.; IR (KBr) 2980, 1520, 1340, 1300, 1170, 1150, 1140, 965, 850, 740 and 610 cm$^{-1}$.

Anal. Calc'd for C$_{20}$H$_{27}$N$_3$O$_4$S$_2$: C, 54.90; H, 6.22; N, 9.60. Found: C, 54.95; H, 6.42; N, 9.41.

EXAMPLE 82 cis-7-Butyl-4,5,6,7-tetrahydro-5-methyl-6-[2-(4-nitrobenzamido)ethyl]thieno[2,3-c]pyridine Hydrochloride The title compound was prepared by Method A using the amine 9i-cis (Table VI) and 4-nitrobenzoyl chloride. The desired product was obtained in 86% yield. This material was treated with HCl/2-propanol (1.1 eq) to afford an off-white solid; mp 197.5°–201° C.; IR (KBr) 3280, 2960, 2500, 1670, 1520, 1350 and 1300 cm$^{-1}$.

Anal. Calc'd for $C_{21}H_{27}N_3O_3S\cdot HCl$: C, 57.59; H, 6.44; N, 9.60. Found: C, 57.77; H, 6.40; N, 9.51.

EXAMPLE 83 cis-7-Butyl-4,5,6,7-tetrahydro-5-methyl-6-[2-(2-nitrobenzamido)ethyl]thieno[2,3-c]pyridine The title compound was prepared by Method A using the amine 9i-cis (Table VI) and 2-nitrobenzoyl chloride. The desired product was obtained in 77% yield. This material was crystallized from $CH_2Cl_2$/ether/hexane to afford an light yellow solid; mp 79°–83° C.; IR (KBr) 3200, 2900, 1600, 1500, 1320 and 690 cm$^{-1}$.

Anal. Calc'd for $C_{21}H_{27}N_3O_3S$: C, 62.82; H, 6.78; N, 10.47. Found: C, 62.60; H, 6.81; N, 10.54.

EXAMPLE 84 cis-7-Hexyl-4,5,6,7-tetrahydro-6-[2-(4-nitrobenzamido)ethyl]-5-methylthieno[2,3-c]pyridine Hydrochloride The title compound was prepared by Method A using the amine 9j-cis (Table VI) and 4-nitrobenzoyl chloride. The desired product was obtained in yield. This material was treated with HCl/2-propanol (1.1 eq) to afford a white solid; mp 171°–173.5° C.; IR (KBr) 3280, 2940, 2500, 1670, 1530, 1350 and 1300 cm$^{-1}$.

Anal. Calc'd for $C_{23}H_{31}N_3O_3S\cdot HCl\cdot\frac{1}{4}H_2O$: C, 58.71; H, 6.96; N, 8.93. Found: C, 59.16; H, 6.99; N, 8.50.

EXAMPLE 85 trans-7-Hexyl-4,5,6,7-tetrahydro-7-methyl-6-[2-(4-nitrobenzamido)ethyl]thieno[2,3-c]pyridine Hydrochloride The title compound was prepared by Method A using the amine 9j-trans (Table VII) and 4-nitrobenzoyl chloride. The desired product was obtained in 100% yield. This material was treated with HCl/2-propanol (1.1 eq) to afford an off-white solid; mp 164 (shrinks) 193°–195° C.; IR (KBr) 3250, 2940, 2440, 1670, 1530, 1350 and 1300 cm$^{-1}$.

Anal. Calc'd for $C_{23}H_{31}N_3O_3S\cdot HCl$: C, 59.28; H, 6.92; N, 9.02. Found: C, 59.27; H, 6.80; N, 8.90.

EXAMPLE 86 cis-4,5,6,7-Tetrahydro-5-methyl-6-[2-(4-nitrobenzamido)ethyl]-7-phenylthieno[2,3-c]pyridine Hydrochloride The title compound was prepared by Method A using the amine 9k-cis (Table VI) and 4-nitrobenzoyl chloride. The desired product was obtained in yield after treatment with HCl/2-propanol (1.1 eq) to afford a light green solid; mp 245°–247° C.; IR (KBr) 3280, 2900, 2580, 1660, 1600, 1520 and 1350 cm$^{-1}$.

Anal. Calc'd for $C_{23}H_{23}N_3O_3S\cdot HCl$: C, 60.32; H, 5.28; N, 9.18. Found: C, 60.66; H, 5.40; N, 8.86.

EXAMPLE 87 trans-4,5,6,7-Tetrahydro-5-methyl-6-[2-(4-nitrobenzamido)ethyl]7-phenylthieno[2,3-c]pyridine Hydrochloride The title compound was prepared by Method A using the amine 9k-trans (Table VII) and 4-nitrobenzoyl chloride. The desired product was obtained in 61% yield after treatment with HCl/2-propanol (1.1 eq) to afford a tan solid; mp 211°–213.5° C.; IR (KBr) 3250, 1650, 1590, 1520, 1330, 1280 and 710 cm$^{-1}$.

Anal. Calc'd for $C_{23}H_{23}N_3O_3S\cdot HCl$: C, 60.32; H, 5.28; N, 9.18. Found: C, 60.63; H, 5.29; N, 8.81.

EXAMPLE 88 cis-4,5,6,7-Tetrahydro-5-methyl-6-[2-(3-nitrobenzamido)ethyl]-7-phenylthieno[2,3-c]pyridine Hydrochloride The title compound was prepared by Method A using the amine 9k-cis (Table VI) and 3-nitrobenzoyl chloride. The desired product was obtained in yield after treatment with HCl/2-propanol (1.1 eq) to afford a tan solid; mp 198°–203° C.; IR (KBr) 3250, 2680, 1700, 1530, 1390, 1200 and 750 cm$^{-1}$.

Anal. Calc'd for $C_{23}H_{23}N_3O_3S\cdot HCl$: C, 60.32; H, 5.28; N, 9.18. Found: C, 60.49; H, 5.51; N, 9.01.

EXAMPLE 89 cis-4,5,6,7-Tetrahydro-5-methyl-6-[2-(2-nitrobenzamido)ethyl]-7-phenylthieno[2,3-c]pyridine Hydrochloride The title compound was prepared by Method A using the amine 9k-cis (Table VI) and 2-nitrobenzoyl chloride. The desired product was obtained in yield after treatment with HCl/2-propanol (1.1 eq) to afford a tan solid; mp (shrinks) 150°–155° C.; IR (KBr) 3440, 2500, 1670, 15909 1360 and 1320 cm$^{-1}$.

Anal. Calc'd for $C_{23}H_{23}N_3O_3S\cdot HCl$: C, 60.32; H, 5.28; N, 9.18. Found: C, 60.22; H, 5.57; N, 9.05.

EXAMPLE 90 cis-4,5,6,7-Tetrahydro-5-methyl-6-[2-(4-nitrophenylsulfonamido)ethyl]-7-phenylthieno[2,3-c]pyridine The title compound was prepared by Method A using the amine 9k-cis (Table VI) and 4-benzenesulfonyl chloride. The desired product was obtained in 55% yield after recrystallization with $CH_2Cl_2$/ether. The title compound was obtained as a yellow solid; mp 149°–152° C.; IR (KBr) 3300, 1600, 1510, 1420, 1350, 1300 and 1150 cm$^{-1}$.

Anal. Calc'd for $C_{22}H_{23}N_3O_4S_2$: C, 57.76; H, 5.07; N, 9.19. Found: C, 57.73; H, 4.90; N, 9.18.

EXAMPLE 91 cis-4,5,6,7-Tetrahydro-7-(4-methoxyphenyl)-5-methyl-6-[2-(4-nitrobenzamido)ethyl]thieno[2,3-c]pyridine The title compound was prepared by Method A using the amine 9l-cis (Table VI) and 4-nitrobenzoyl chloride. The desired product was obtained in yield after recrystallization with $CH_2Cl_2$/hexane. The title compound was obtained as a yellow solid; mp 153.5°–155.5° C.; IR (KBr) 3340, 3000, 1640, 1550, 1400, 1300 and 1160 cm$^{-1}$.

Anal. Calc'd for $C_{24}H_{25}N_3O_4S$: C, 63.84; H, 5.58; N, 9.31. Found: C, 63.65; H, 5.35; N, 9.53.

EXAMPLE 92 trans-4,5,6,7-Tetrahydro-7-(4-methoxyphenyl)-5-methyl-6-[2-(4-nitrobenzamido)ethyl]thieno[2,3-c]pyridine Hydrochloride The title compound was prepared by Method A using the amine 9l-trans (Table VII) and 4-nitrobenzoyl chloride. The desired product was obtained in 96% yield. This material was treated with HCl/2-propanol in 2-propanol/ether to afford a yellow solid; mp 210 (darkens) 225°–226.5° C.; IR (KBr) 3200, 2920, 1650, 1590, 1500, 1330 and 1010 cm$^{-1}$.

Anal. Calc'd for $C_{24}H_{25}N_3O_4S$·HCl: C, 59.07; H, 5.37; N, 8.61. Found: C, 59.13; H, 5.43; N, 8.63.

EXAMPLE 93 cis-7-(4-Chlorophenyl)-4,5,6,7-tetrahydro-5-methyl-6-[2-(4-nitrobenzamido)ethyl]thieno[2,3-c]pyridine The title compound was prepared by Method A using the amine 9m-cis (Table VI) and 4-nitrobenzoyl chloride. The titled compound was isolated as a tan solid in 60% yield after recrystallization with $CH_2Cl_2$/hexane; mp 139°–142° C.; IR (KBr) 3340, 3000, 1650, 1540, 1350 and 1280 cm$^{-1}$.

Anal. Calc'd for $C_{23}H_{22}ClN_3O_3S$: C, 60.59; H, 4.86; N, 9.22. Found: C, 60.33; H, 4.92; N, 9.25.

EXAMPLE 94 trans-7-(4-Chlorophenyl)-4,5,6,7-tetrahydro-5-methyl-6-[2-(4-nitrobenzamido)ethyl]thieno[2,3-c]pyridine Hydrochloride The title compound was prepared by Method A using the amine 9m-trans (Table VII) and 4-nitrobenzoyl chloride to produce the desired product in 98% yield. This material was treated with HCl/2-propanol (1.1 eq) to afford an off-white solid; mp 230 (darkens) 236°–239.5° C.; IR (KBr) 3190, 2920, 2620, 1650, 1510, 1330 and 1080 cm$^{-1}$.

Anal. Calc'd for $C_{23}H_{22}ClN_3O_3S$·HCl: C, 56.10; H, 4.71; N, 8.54. Found: C, 56.12; H, 4.78; N, 8.35.

EXAMPLE 95 cis-4,5,6,7-Tetrahydro-5-methyl-6-[2-(4-nitrobenzamido)ethyl]-7-(thien-2-yl)thieno[2,3-c]pyridine Hydrochloride The title compound was prepared by Method A using the amine 9n-cis (Table VI) and 4-nitrobenzoyl chloride to produce the desired product in 98% yield. This material was treated with HCl/2-propanol (1.1 eq) to afford an off-white solid; mp 195 (darkens) 207°–209° C.; IR (KBr) 3260, 3110, 2900, 2540, 2500, 1650, 1600, 1520, 1350, and 710 cm$^{-1}$.

Anal. Calc'd for $C_{21}H_{21}N_3O_3S_2$·HCl: C, 54.37; H, 4.78; N, 9.06. Found: C, 54.36; H, 4.61; N, 8.88.

EXAMPLE 96 cis-4,5,6,7-Tetrahydro-5-methyl-6-[2-(4-nitrobenzenesulfonamido)ethyl]-7-(thien-2-yl)thieno[2,3-c]pyridine The title compound was prepared by Method A using the amine 9n-cis (Table VI) and 4-nitrobenzenesulfonyl chloride to produce the desired product in 79% yield. This material was recrystallized with MeOH/hexane to afford a light yellow solid; mp 134.5°–136° C.; IR (KBr) 3300, 3000, 2840, 1530, 1350, 1160, 1090 and 720 cm$^{-1}$.

Anal. Calc'd for $C_{20}H_{21}N_3O_4S_3$: C, 51.83; H, 4.57; N, 9.07. Found: C, 51.98; H, 4.54; N, 9.16.

EXAMPLE 97 cis-4,5,6,7-Tetrahydro-7-methyl-6-[2-(4-nitrobenzamido)ethyl]-5-propylthieno[2,3-c]pyridine Hydrochloride The title compound was prepared by Method A using the amine 9o-cis (Table VI) and 4-nitrobenzoyl chloride to produce the desired product in 50% yield. This material was treated with HCl/2-propanol (1.1 eq) to afford a tan solid; mp 242°–243.5° C.; IR (KBr) 3280, 2960, 2540, 1670, 1520, 1350 and 1300 cm$^{-1}$.

Anal. Calc'd for $C_{20}H_{25}N_3O_3S$·HCl: C, 56.66; H, 6.18; N, 9.91. Found: C, 56.54; H, 6.19; N, 9.77.

EXAMPLE 98 cis-4,5,6,7-Tetrahydro-7-methyl-6-[3-(4-nitrobenzamido)propyl]-5-propylthieno[2,3-c]pyridine The title compound was prepared by Method A using the amine 9s-cis (Table VI) and 4-nitrobenzoyl chloride to produce the desired product in 89% yield. This material was recrystallized with $CH_2Cl_2$/hexane/ether to afford a yellow solid; mp 99.5°–103.5° C.; IR (KBr) 3310, 2960, 2920, 2860, 1630, 1600, 1540, 1520, 1350 and 865 cm$^{-1}$.

Anal. Calc'd for $C_{21}H_{27}N_3O_3S$: C, 62.82; H, 6.78; N, 10.47. Found: C, 62.77; H, 6.86; N, 10.50.

EXAMPLE 99 cis-4,5,6,7-Tetrahydro-7-methyl-6-[3-(4-nitrobenzenesulfonamido)propyl]-5-propylthieno[2,3-c]pyridine Hydrochloride The title compound was prepared by Method A using the amine 9s-cis (Table VI) and 4-nitrobenzenesulfonyl chloride to produce the desired product in 53% yield. This material was treated with HCl/2-propanol (1.1 eq) to afford a tan solid; mp 133°–137° C.; IR (KBr) 3420, 3030, 2960, 2930, 2500, 1525, 1345, 1305, 1160, 1090, 740 and 610 cm$^{-1}$.

Anal. Calc'd for $C_{20}H_{27}N_3O_4S_2$·HCl: C, 50.68; H, 5.96; N, 8.87. Found: C, 50.71; H, 5.78; N, 8.69.

EXAMPLE 100 cis-4,5,6,7-Tetrahydro-4,7-dimethyl-6-[2-(4-nitrobenzamido)ethyl]-thieno[2,3-c]pyridine Hydrochloride An ether/$CH_2Cl_2$ (10/20 mL) solution of amine 9p-cis (Table VI) (450 mg, 2.13 mmol) was treated with pyridine (0.22 mL, 2.77 mmol) and 4-nitrobenzoyl chloride (480 mg, 2.59 mmol) for 16 hours at rt. The title compound was isolated directly as its hydrochoride salt in 30% yield as a white powder; mp 185°–187° C.; IR (KBr) 2458, 1663, 1602, 1545, 1523, 1346 and 1295 cm$^{-1}$.

Anal. Calc'd for $C_{18}H_{21}N_3O_3S$·HCl: C, 54.61; H, 5.61; N, 10.61. Found: C, 54.32; H, 5.45; N, 10.48.

EXAMPLE 101 trans-4,5,6,7-Tetrahydro-4,7-dimethyl-6-[2-(4-nitrobenzamido)ethyl]thieno[2,3-c]pyridine Hydrochloride The title compound was prepared by the procedure for Example 100 using the amine 9p-trans (Table VII) and 4-nitrobenzoyl chloride to produce the desired product in 53% yield; mp 222°–224° C.; IR (KBr) 3241, 2616, 1671, 1602, 1526, 1347, 1322 and 1291 cm$^{-1}$.

Anal. Calc'd for $C_{18}H_{21}N_3O_3S \cdot HCl$: C, 54.61; H, 5.61; N, 10.61. Found: C, 54.22; H, 5.29; N, 10.38.

EXAMPLE 102 cis-6-[2-(4-Aminobenzamido)ethyl]-4,5,6,7-tetrahydro-5,7-dimethyl-thieno[2,3-c]pyridine Dihydrochloride Prepared by Method C (glacial acetic acid as solvent) using the nitro compound in Example 28 and isolated in 58% yield. This material was treated with HCl/2-propanol (1.1 eq) to afford a peach-colored solid; mp 190°–210° C.; IR (KBr) 2910, 2850, 2590, 1610, 1545, 1500, 1300, 850, 835, 760 and 730 cm$^{-1}$.

Anal. Calc'd for $C_{18}H_{23}N_3OS \cdot 2HCl$: C, 51.43; H, 6.47; N, 9.99. Found: C, 51.45; H, 6.74; N, 9.55.

EXAMPLE 103 trans-6-[2-(4-Aminobenzamido)ethyl]-4,5,6,7-tetrahydro-5,7-dimethylthieno[2,3-c]pyridine Prepared by Method C using the nitro compound in Example 29 and isolated in 36% yield; MH+ at m/z 330; IR (KBr) 3370, 3250, 2990, 2950, 1615, 1100, 1195, 1155, 850 and 780 cm$^{-1}$.

EXAMPLE 104 cis-6-[2-(2-Aminobenzamido)ethyl]-4,5,6,7-tetrahydro-5,7-dimethylthieno[2,3-c]pyridine Prepared by Method C using the nitro compound in Example 32 and isolated in 96% yield. This material was recrystallized from ether/hexane to afford an off-white solid; mp 89°–94° C.; IR (KBr) 3420, 3300, 2860, 1630, 1550, 1500, 1280 and 1160 cm$^{-1}$.

Anal. Calc'd for $C_{18}H_{23}N_3OS$: C, 65.63; H, 7.04; N, 12.76. Found: C, 65.52; H, 7.27; N, 12.63.

EXAMPLE 105 cis-6-[2-(4-Aminobenzenesulfonamido)ethyl]-4,5,6,7-tetrahydro-5,7-dimethylthieno[2,3-c]pyridine Prepared by Method C using the nitro compound in Example 63 and isolated in 52% yield after recrystallization from $CH_2Cl_2$/ether/hexane to afford an off-white solid; mp 126°–131° C.; IR (KBr) 3400, 2960, 1640, 1590, 1460, 1320 and 1150 cm$^-$.

Anal. Calc'd for $C_{17}H_{23}N_3O_2S_2 \cdot \frac{1}{4}H_2O$: C, 55.20; H, 6.40; N, 11.36. Found: C, 55.13; H, 6.41; N, 11.22.

EXAMPLE 106 cis-6-[2-(2-Aminobenzenesulfonamido)ethyl]-4,5,6,7-tetrahydrothieno[2,3-c]pyridine Hydrochloride Prepared by Method C using the nitro compound in Example 65 and isolated in 56% yield. This material was treated with HCl/2-propanol (1.1 eq) to afford an off-white solid; mp 221°–223.5° C.; IR (KBr) 3400, 2500, 1660, 1480, 1300 and 1150 cm$^{-1}$.

Anal. Calc'd for $C_{17}H_{23}N_3O_2S_2 \cdot HCl$: C, 50.81; H, 6.02; N, 10.46. Found: C, 50.87; H, 6.11; N, 10.35.

EXAMPLE 107 cis-6-[3-(4-Aminobenzamido)-4,5,6,7-tetrahydro-5,7-dimethylpropyl]thieno[2,3-c]pyridine Prepared by Method C using the nitro compound in Example 69 and isolated in 89% yield as a bright yellow glassy solid; MH+ at m/z 344; IR (neat) 3350, 3230, 2980, 1610, 1550, 1505, 1295, 1190, 845 and 775 cm$^{-1}$.

EXAMPLE 108 cis-6-[3-(4-Aminophenylsulfonamido)propyl]-4,5,6,7-tetrahydro-5,7-dimethylthieno[2,3-c]pyridine Prepared by Method C using the nitro compound in Example 70 and isolated in 100% crude yield. This material was crystallized from $CH_2Cl_2$/MeOH/ether to afford a light beige solid; mp 134°–138° C.; IR (KBr) 3470, 3370, 1630, 1590, 1310, 1155, 1095 and 550 cm$^{-1}$.

Anal. Calc'd for $C_{18}H_{25}N_3O_2S_2$: C, 56.96; H, 6.64; N, 11.07. Found: C, 56.48; H, 6.81; N, 10.62.

EXAMPLE 109 cis-6-[4-(4-Aminobenzamido)-4,5,6,7-tetrahydro-5,7-dimethylbutyl]thieno[2,3-c]pyridine Prepared by Method D using the nitro compound in Example 72 and isolated in 82% yield; MH+ at m/z 358; IR (neat) 3340, 2980, 2940, 1630, 1600, 1550, 1500, 1290, 1190, 910 and 740 cm$^{-1}$.

EXAMPLE 110 cis-6-[4-(4-Aminobenzenesulfonamido)butyl]-4,5,6,7-tetrahydro-5,7-dimethylthieno[2,3- c]pyridine Prepared by Method D using the nitro compound in Example 73 and isolated in 69% yield; MH+ at m/z 394; IR (neat) 3380, 3280, 2880, 1580, 1550, 1450, 1260, 1100, 1040 and 780 cm$^{-1}$.

EXAMPLE 111

1-(4-Aminobenzoyl)-4-(4,5,6,7-tetrahydrothiono[2,3-c]pyridin-6-yl)-piperidine

Prepared by Method C using the nitro compound in Example 74 and isolated in 100% yield; MH+ at m/z 342.

EXAMPLE 112 cis-6-[2-(4-Aminobenzamido)ethyl]-2-bromo-4,5,6,7-tetrahydro-5,7-dimethylthieno[2,3-c]pyridine Prepared by Method C using the nitro compound in Example 76 and isolated in 40% yield; MH+ at m/z 408; IR (neat) 3340, 2970, 1640, 1630, 1500, 1300, 1280, 1260, 1185, 905 and 840 cm$^{-1}$.

EXAMPLE 113 cis-6-[2-(4-Aminophenoxy)ethyl]-4,5,6,7-tetrahydro-5,7-dimethylthieno[2,3-c]pyridine Prepared by Method D using the nitro compound in Example 78 and isolated in 40% yield; IR (neat) 3460, 3320, 3100, 2980, 1620, 1510, 1370, 1230, 1040 and 830 cm$^{-1}$.

EXAMPLE 114 cis-6-[2-(4-Aminobenzamido)ethyl]-4,5,6,7-tetrahydro-5,7-dimethyl-N-methylthieno[2,3-c]pyridine Prepared by Method C using the nitro compound in Example 79 and isolated in 99% yield; MH+ at m/z 344; IR (neat) 3480, 3360, 3240, 2980, 2940, 1620, 1610, 1485, 1400, 1300, 1180, 1080, 840 and 740 cm$^{-1}$.

EXAMPLE 115 cis-6-[2-(4-Aminophenylsulfonamido)ethyl]-4,5,6,7-tetrahydro-5,7-dimethyl-N-(l-methylethyl)thieno[2,3-c]pyridine Prepared by Method C using the nitro compound in Example 81 and isolated in 87% yield; MH+ at m/z 408; IR (KBr) 3460, 3370, 2960, 1620, 1590, 1495, 1330, 1300, 1135, 1085, 965, 825, 725 and 705 cm$^{-1}$.

EXAMPLE 116 cis-6-[2-(4-Aminobenzamido)ethyl]-7-butyl-4,5,6,7-tetrahydro-5-methylthieno[2,3-c]pyridine Prepared by Method C using the nitro compound in Example 82 and isolated in 79% yield; MH+ at m/z 372.

EXAMPLE 117 cis-6-[2-(4-Aminobenzamido)ethyl]-4,5,6,7-tetrahydro-5-methyl-7-phenylthieno[2,3-c]pyridine Prepared by Method C using the nitro compound in Example 86 and isolated in 51 % yield; MH+ at m/z 392; IR (neat) 3340, 3220, 2970, 1640, 1600, 1445, 1185, 1135, 1075, 965 and 840 cm$^{-1}$.

EXAMPLE 118 cis-6-[2-(4-Aminobenzenesulfonamido)ethyl]-4,5,6,7-tetrahydro-5-methyl-7-phenylthieno[2,3-c]pyridine Prepared by Method C using the nitro compound in Example 90 and isolated in 69% yield. This material was crystallized from $CH_2Cl_2$/MeOH to afford an off-white solid; mp 184°-186.5° C.; IR (KBr) 3360, 1620, 1590, 1300 and 1140 cm$^{-1}$.

Anal. Calc'd for $C_{22}H_{25}N_3O_2S_2$: C, 61.81; H, 5.90; N, 9.83. Found: C, 61.75; H, 5.71; N, 9.83.

EXAMPLE 119 cis-6-[2-(4-Aminobenzenesulfonamido)ethyl]-4,5,6,7-tetrahydro-5-methyl-7-(thien-2-yl)thieno[2,3-c]pyridine Prepared by Method D using the nitro compound in Example 96 and isolated in 53% yield. This material was crystallized from $CH_2Cl_2$/hexane to afford an off-white solid; mp 156°-161° C.; IR (KBr) 3350, 2900, 1630, 1590, 1310, 1150 and 690 cm$^{-1}$.

Anal. Calc'd for $C_{22}H_{25}N_3O_2S_2$: C, 55.42; H, 5.35; N, 9.70. Found: C, 55.45; H, 5.21; N, 9.70.

EXAMPLE 120 cis-6-[2-(4-Aminobenzamido)ethyl]-4,5,6,7-tetrahydro-7-methyl-5-propylthieno[2,3-c]pyridine Prepared by Method C using the nitro compound in Example 97 and isolated in 69% yield; MH+ at m/z 358; IR (neat) 3460, 3360, 3240, 2970, 2940, 2880, 1645, 1605, 1510, 1380, 1290, 1185, 1155, 845, 775, 740 and 710 cm$^{-1}$.

EXAMPLE 121 cis-6-[3-(4-Aminobenzamido)propyl]-4,5,6,7-tetrahydro-7-methyl-5-propylthieno[2,3-c]pyridine Prepared by Method D using the nitro compound in Example 98 and isolated as a yellow oil in 79% yield; MH+ at m/z 372; IR (neat) 3480, 3330, 3220,2950,2920,2860,1640,1620,1500,1370,1300,1180,83-5,765, 740 and 700 cm$^{-1}$.

EXAMPLE 122 cis-6-[2-(4-Aminobenzamido)ethyl]-4,5,6,7-tetrahydro-4,7-dimethylthieno[2,3-c]pyridine Prepared by Method D using the nitro compound in Example 100 and isolated in 78% yield; MH+ at m/z 330; IR (neat) 3420, 3340, 3210, 3105, 3080, 3060, 2960, 2800, 1640, 1620, 1600, 1500, 1280, 1180, 1130, 920 and 860 cm$^{-1}$.

EXAMPLE 123 trans-6-[2-(4-Aminobenzamido)ethyl]-4,5,6,7-tetrahydro-4,7-dimethylthieno[2,3-c]pyridine Prepared by Method D using the nitro compound in Example 101 and isolated in 75% yield; IR (neat) 3450, 3340, 3220, 2960, 2810, 1620, 1600, 1540, 1500, 1280, 1180, 910, 840 and 740 cm$^{-1}$.

EXAMPLE 124 cis-6-[2-[4-(Acetylamino)benzamido]ethyl]-4,5,6,7-tetrahydro-5,7-dimethylthieno[2,3-c]pyridine Prepared by Method E using the aminobenzene compound in Example 102 and isolated in 78% yield after flash silica gel chromatography using 1.5-5% MeOH in $CH_2Cl_2$. This material was crystallized from MeOH/ether to afford an off-white solid; mp 161°-162° C.; IR (KBr) 3320, 3260, 3120,3070,2970,1685,1630,1605,1535,1500,1375,1320,12-95,1270, 1185, 1155, 855, 840, 775, 710 and 680 cm$^{-1}$.

Anal. Calc'd for $C_{20}H_{25}N_3O_2S$: C, 64.67; H, 6.78; N, 11.31. Found: C, 64.55; H, 6.72; N, 11.09.

EXAMPLE 125 cis-6-[2-[2-(Acetylamino)benzamido]ethyl]-4,5,6,7-tetrahydro-5,7-dimethylthieno[2,3-c]pyridine Prepared by Method E using the aminobenzene compound in Example 104 and isolated in 53% yield after flash silica gel chromatography using EtOAc. This material was crystallized from $CH_2Cl_2$/hexane to afford an off-white solid; mp 108.5°-112° C.; IR (KBr) 3250, 2960, 1650, 1600, 1530, 1440 and 1300 cm$^{-1}$.

Anal. Calc'd for $C_{20}H_{25}N_3O_2S$: C, 64.67; H, 6.78; N, 11.31. Found: C, 64.78; H, 6.92; N, 11.06.

EXAMPLE 126 cis-4,5,6,7-Tetrahydro-5,7-dimethyl-6-[2-[4-(trimethylacetylamino)benzamido]ethyl]thieno[2,3-c]pyridine Prepared by Method E using the aminobenzene compound in Example 102. This material was purified by flash silica gel chromatography using 3% MeOH in $CH_2Cl_2$ and recrystallized from $CH_2Cl_2$/hexane to afford the title compound as a white solid; mp 133° C. (discolors) 136°-138° C.; IR (KBr) 3330, 2970, 1660, 1630, 1500, 1400, 1310, 1245, 1185, 1170, 855, 835, 770 and 710 cm$^{-1}$.

Anal. Calc'd for $C_{23}H_{31}N_3O_2S \cdot \frac{1}{2}H_2O$: C, 65.37; H, 7.63; N, 9.94. Found: C, 65.73; H, 7.80; N, 9.44.

EXAMPLE 127 cis-6-(2-[4-(Trifluoroacetamido)benzamido]ethyl)-4,5,6,7-tetrahydro-5,7-dimethylthieno[2,3-c]pyridine A $CH_2Cl_2$ solution (15 mL) of the aminobenzene compound in Example 104 (1.0g, 3.04 mmol) was cooled in an ice-bath and treated with trifluoroacetic anhydride (0.47 mL, 3.34 mmol) under nitrogen. The reaction solution was warmed to rt, quenched with saturated NaHCO$_3$ solution and the CH$_2$Cl$_2$ layer was dried over MgSO$_4$. Solvent removal produced the crude material that was purified by flash silica gel chromatography using 0.5-5% MeOH in CH$_2$Cl$_2$. The title compound was isolated (91 %) and crystallized from CH$_2$Cl$_2$/hexane/ether to afford an off-white solid; mp 174.5°-177° C.; IR (KBr) 3380, 3070, 2970, 2910, 1710, 1640, 1540, 1500, 1280, 1200 and 11 60 cm$^{-1}$.

Anal. Calc'd for C$_{20}$H$_{22}$F$_3$N$_3$O$_2$S: C, 56.46; H, 5.21; N, 9.88. Found: C, 56.44; H, 5.14; N, 9.69.

EXAMPLE 128 cis-6-[2-[4-(Acetylamino)benzenesulfonamido]ethyl]-4,5,6,7-tetrahydro-5,7-dimethylthieno[2,3-c]pyridine Prepared by Method E using the aminobenzene compound in Example 105 and isolated in 61% yield after flash silica gel chromatography using 1-5% MeOH in CH$_2$Cl$_2$. This material was crystallized from CH$_2$Cl$_2$/ether to afford a light purple solid; mp 141.5°-144° C.; IR (KBr) 3400, 3200, 1680, 1600, 1530, 1330, and 1160 cm$^{-1}$.

Anal. Calc'd for C$_{19}$H$_{25}$N$_3$O$_3$S$_2$: C, 56.01; H, 6.19; N, 10.31. Found: C, 55.84; H, 6.23; N, 10.15.

EXAMPLE 129 cis-6-[2-(2-Acetamidobenzenesulfonamido)ethyl]-4,5,6,7-tetrahydro-5,7-dimethylthieno[2,3-c]pyridine Prepared by Method E using the aminobenzene compound in Example 106. This material was isolated in 39% yield after flash silica gel chromatography using 1-3% MeOH in CH$_2$Cl$_2$ and crystallization from CH$_2$Cl$_2$/ether/hexane to afford an off-white solid; mp 104.5°-109° C.; IR (KBr) 3340, 3200, 1690, 1590, 1540, 1330 and 1150 cm$^{-1}$.

Anal. Calc'd for C$_{19}$H$_{25}$N$_3$O$_3$S$_2$: C, 56.01; H, 6.19; N, 10.31. Found: C, 55.99; H, 6.17; N, 10.20.

EXAMPLE 130 cis-4,5,6,7-Tetrahydro-5,7-dimethyl-6-[2-(4-methanesulfonylaminobenzamido)ethyl]thieno[2,3-c]pyridine Monooxalate Prepared by Method F using the aminobenzene compound in Example 102 and methanesulfonyl chloride. The title compound was isolated as a white foam in 57% yield after flash silica gel chromatography using 1-5% MeOH in CH$_2$Cl$_2$. This material was dissolved in EtOH and treated with oxalic acid (1.1 eq) to afford the title compound as a tan solid; mp 218.5°-219° C. (dec); IR (KBr) 3370, 3100, 2980, 2930, 1660, 1605, 1555, 1500, 1335, 1150, 970 and 940 cm$^{-1}$.

Anal. Calc'd for C$_{19}$H$_{25}$N$_3$O$_3$S$_2$.C$_2$H$_2$O$_4$: C, 50.69; H, 5.47; N, 8.44. Found: C, 50.69; H, 5.53; N, 8.29.

EXAMPLE 131 trans-4,5,6,7-Tetrahydro-5,7-dimethyl-6-[2-(4-methanesulfonylamino-benzamido)ethyl]thieno[2,3-c]pyridine Monooxalate Prepared by Method F using the aminobenzene compound in Example 103 and methanesulfonyl chloride. The title compound was isolated as a white foam in 66% yield after flash silica gel chromatography using 2-4% MeOH in CH$_2$Cl$_2$. This material was dissolved in acetone and treated with oxalic acid (1.1 eq) to afford the title compound as a tan solid; mp 188°-192° C. (dec); IR (KBr) 3360, 1650, 1610, 1555, 1505, 1330, 1310 and 1150 cm$^{-1}$.

Anal. Calc'd for C$_{19}$H$_{25}$N$_3$O$_3$S$_2$.C$_2$H$_2$O$_4$: C, 50.69; H, 5.47; N, 8.44. Found: C, 50.82; H, 5.52; N, 8.12.

EXAMPLE 132 cis-4,5,6,7-Tetrahydro-6-(2-[4-(methanesulfonylamino)-benzenesulfonamido]ethyl)-5,7-dimethylthieno[2,3-c]pyridine Hydrochloride Prepared by Method F using the aminobenzene compound in Example 105 and methanesulfonyl chloride. The title compound was isolated directly as its hydrochloride salt as a light beige solid in 30% yield after trituration of the crude reaction material (pyridine removed in vacuo) with ether; mp 227°-228° C.; IR (KBr) 3440, 3100, 2920, 2640, 2600, 1600, 1490, 1340, 1150, 960, 840 and 760 cm$^{-1}$.

Anal. Calc'd for C$_{18}$H$_{25}$N$_3$O$_4$S$_3$.HCl.$\frac{1}{4}$H$_2$O: C, 44.60; H, 5.53; N, 8.66. Found: C, 44.98; H, 5.92; N, 8.35.

EXAMPLE 133 cis-4,5,6,7-Tetrahydro-5,7-dimethyl-6-[3-(4-methanesulfonylaminobenzamido)propyl]thieno[2,3-c]pyridine Prepared by Method F using the aminobenzene compound in Example 107 and methanesulfonyl chloride. The title compound was isolated as a dark glassy material that was crystallized from CH$_2$Cl$_2$/ether in 62% yield There was obtained a beige solid; mp 148°-150° C.; IR (KBr) 3410, 3180, 1635, 1545, 1500, 1340, 1300, 1150, 780, 700 and 610 cm$^{-1}$.

Anal. Calc'd for C$_{20}$H$_{27}$N$_3$O$_3$S$_2$: C, 56.98; H, 6.46; N, 9.97. Found: C, 56.71; H, 6.61; N, 9.92.

EXAMPLE 134 cis-4,5,6,7-Tetrahydro-6-[3-(4-methanesulfonamidophenylsulfonamido)propyl]-5,7-dimethylthieno[2,3-c]pyridine Hydrochloride Prepared by Method F using the aminobenzene compound in Example 108 and methanesulfonyl chloride. The title compound was isolated as a yellow foam in 50% yield after flash silica gel chromatography using NH$_4$OH/MeOH in CH$_2$Cl$_2$(0.25/2.25% to 0.5/4.5%). This material was treated with HCl/2-propanol (1.1 eq) to afford the title compound as a tan foamy solid; mp 128° C. (softens) 146°-152° C.; IR (KBr) 3100, 1600, 1325 and 1150 cm$^{-1}$.

Anal. Calc'd for C$_{19}$H$_{27}$N$_3$O$_4$S$_3$.HCl: C, 46.19; H, 5.71; N, 8.50. Found: C, 46.10; H, 5.64; N, 8.28.

EXAMPLE 135 cis-4,5,6,7-Tetrahydro-6-[4-(4-methanesulfonamidobenzamido)butyl]-5,7-dimethylthieno[2,3-c]pyridine Prepared by Method F using the aminobenzene compound in Example 109 and methanesulfonyl chloride. The title compound was isolated in 45% yield after flash silica gel chromatography using 1-4% EtOH in EtOAc. This material was crystallized from CH$_2$Cl$_2$/hexane/ether to afford the title compound as an off-white solid; mp 112.5°-116° C.; IR (KBr) 3400, 3180, 2960, 1630, 1540, 1500, 1330 and 1150 cm$^{-1}$.

Anal. Calc'd for C$_{21}$H$_{29}$N$_3$O$_3$S$_2$: C, 57.92; H, 6.71; N, 9.65. Found: C, 57.94; H, 6.82; N, 9.52.

EXAMPLE 136 cis-4,5,6,7-Tetrahydro-6-[4-(4-methanesulfonamidobenzenesulfonamido)butyl]-5,7-dimethylthieno[2,3-c]pyridine Hydrochoride Prepared by Method F using the aminobenzene compound in Example 110 and methanesulfonyl chloride. The title compound was isolated in 91 % yield after flash silica gel chromatography using 2-5% MeOH in $CH_2Cl_2$. This material was treated with HCl/2-propanol (1.1eq) and then recrystallized from EtOH to afford the title compound as a tan solid; mp 134°–136.5° C.; IR (KBr) 3470, 3130, 2920, 2850, 2600, 1600, 1460, 1320, 1140, 1090 and 720 cm$^{-1}$.

Anal. Calc'd for $C_{20}H_{29}N_3O_4S_3 \cdot HCl \cdot \frac{1}{2}H_2O$: C, 46.46; H, 6.04; N, 8.12. Found: C, 46.43; H, 6.05; N, 8.03

EXAMPLE 137

4-(4,5,6,7-Tetrahydrothieno[2,3-c]pyridin-6-yl)-1-(4-methanesulfonylaminobenzoyl)pipeline Prepared by Method F using the aminobenzene compound in Example 11 1 and methanesulfonyl chloride. The title compound was isolated in 91 % yield after flash silica gel chromatography using 1-4% MeOH in $CH_2Cl_2$. This material was crystallized from $CH_2Cl_2$/MeOH to afford the title compound as a white solid; mp 195°–198° C.; IR (KBr) 3120, 2920, 1600, 1445, 1330, 1145, 960, 920, 845, 760 and 705 cm$^{-1}$.

Anal. Calc'd for $C_{20}H_{25}N_3O_3S_2$: C, 57.25; H, 6.01; N, 10.02. Found: C, 56.85; H, 6.07; N, 10.02.

EXAMPLE 138 cis-2-Bromo-4,5,6,7-tetrahydro-6-[2-(4-methanesulfonamidobenzamido)ethyl]-5,7-dimethylthieno[2,3- c]pyridine Hydrochloride Prepared by Method F using the aminobenzene compound in Example 112 and methanesulfonyl chloride. The title compound was isolated in 78% yield after flash silica gel chromatography using 1-3% MeOH in $CH_2Cl_2$. This material was treated with HCl/2-propanol (1.1eq) to afford the title compound as a tan solid; mp 144° C. (shrinks), 157°–160° C.; IR (KBr) 3380, 3110, 3050, 2930, 1710, 1655, 1600, 1500, 1390, 1335, 1230, 1150, 970, 960, 905, 855, and 730 cm$^-$.

Anal. Calc'd for $C_{19}H_{24}BrN_3O_3S_2 \cdot HCl$: C, 43.64; H, 4.82; N, 8.04. Found: C, 43.39; H, 4.79; N, 7.83.

EXAMPLE 139 cis-4,5,6,7-Tetrahydro-6-[2-(4-methanesulfonylaminophenoxy)ethyl]-5,7-dimethylthieno-[2,3-c]pyridine Hydrochloride Prepared by Method F using the aminobenzene compound in Example 113 and methanesulfonyl chloride. The crude material was isolated as a bright red oil that was treated with HCl/2-propanol (1.1eq) to afford the title compound as an off-white solid (40%); mp 221°–223° C.; IR (KBr) 3060, 1510, 1340, 1152 and 973 cm$^{-1}$.

Anal. Calc'd for $C_{18}H_{24}N_2O_3S_2 \cdot HCl \cdot \frac{1}{2}H_2O$: C, 51.31; H, 6.09; N, 6.64. Found: C, 51.24; H, 6.03; N, 6.29.

EXAMPLE 140 cis-4,5,6,7-Tetrahydro-6-[2-(4-methanesulfonamidobenzamido)ethyl]-N-methyl-5,7-dimethylthieno[2,3-c]pyridine Hydrochloride Prepared by Method F using the aminobenzene compound in Example 114 and methanesulfonyl chloride. The title compound was isolated as a light yellow viscous material in 89% yield after flash silica gel chromatography using $NH_4OH$/MeOH in $CH_2Cl_2$(0.25/3.75% to 0.5/4.5%). This material was treated with HCl/2-propanol (1.1 eq) to afford the title compound as a light beige foamy solid; mp 129-131 (softens) 160°-170° C. (dec); IR (KBr) 1620, 1600, 1325 and 1145 cm$^{-1}$.

Anal. Calc'd for $C_{20}H_{27}N_3O_3S_2 \cdot HCl$: C, 52.44; H, 6.16; N, 9.17. Found: C, 52.53; H, 5.96; N, 8.79.

EXAMPLE 141 cis-4,5,6,7-Tetrahydro-6-[2-(4-methanesulfonamidophenylsulfonamido)ethyl]-5,7-dimethyl-N-(l-methylethyl)thieno[2,3-c]pyridine Hydrochloride Prepared by Method F using the aminobenzene compound in Example 115 and methanesulfonyl chloride. The title compound was isolated as a white foamy solid after flash silica gel chromatography using 1.5-5% MeOH in $CH_2Cl_2$. This material was treated with HCl/2-propanol (1.1 eq) to afford the title compound as a light beige solid (82%); mp 221.5°–222.5° C. (dec); IR (KBr) 2450, 1590, 1330, 1140 and 960 cm$^{-1}$.

Anal. Calc'd for $C_{21}H_{31}N_3O_4S_3 \cdot HCl$: C, 48.31; H, 6.18; N, 8.05. Found: C, 48.58; H, 6.27; N, 7.75.

EXAMPLE 142 cis-7-Butyl-4,5,6,7-tetrahydro-5-methyl-6-[2-(4-methanesulfonamido-benzamido)ethyl]thieno[2,3-c]pyridine Hydrochloride Prepared by Method F using the aminobenzene compound in Example 116 and methanesulfonyl chloride. The title compound was isolated in 95% yield after flash silica gel chromatography using 0.5-5% MeOH in $CH_2Cl_2$. This material was treated with HCl/2-propanol (1.1 eq) to afford the title compound as an off-white solid; mp 214.5°–216.5° C.; IR (KBr) 3140, 2960, 2500, 1640, 1500, 1340 and 11 50 cm$^{-1}$.

Anal. Calc'd for $C_{22}H_{31}N_3O_3S_2 \cdot HCl$: C, 54.37; H, 6.64; N, 8.65. Found: C, 54.39; H, 6.65; N, 8.49.

EXAMPLE 143.

cis-4,5,6,7-Tetrahydro-5-methyl-6-[2-(4-methanesulfonamidobenzamido)ethyl]-7-phenylthieno[[2,3-c]pyridine Prepared by Method F using the aminobenzene compound in Example 11 7 and methanesulfonyl chloride. The title compound was isolated in 81% yield after flash silica gel chromatography using 0.5-5% MeOH in $CH_2Cl_2$. This material was crystallized from $CH_2Cl_2$/ether to afford the title compound as a light yellow solid; mp 193°–194.5° C.; IR (KBr) 3200, 1620, 1500, 1330, 1290 and 1150 cm$^{-1}$.

Anal. Calc'd for $C_{24}H_{27}N_3O_3S_2$: C, 61.39; H, 5.80; N, 8.95. Found: C, 61.02; H, 5.80; N, 8.87.

EXAMPLE 144 cis-4,5,6,7-Tetrahydro-5-methyl-6-[2-(4-methanesulfonamidobenzenesulfonamido)ethyl]-7-phenylthieno[2,3-c]pyridine Prepared by Method F using the aminobenzene compound in Example 11 8 and methanesulfonyl chloride. The title compound was isolated in 91 % yield after flash silica gel chromatography using 1 % MeOH in $CH_2Cl_2$. This material was crystallized from MeOH/hexane to afford the title compound as an off-white solid; mp 155°-158° C.; IR (KBr) 3260, 1590, 1460, 1320, 1150 and 970 cm$^{-1}$.

Anal. Calc'd for $C_{23}H_{27}N_3O_4S_3$: C, 54.65; H, 5.38; N, 8.31. Found: C, 54.55; H, 5.37; N, 8.43.

EXAMPLE 145 cis-4,5,6,7-Tetrahydro-6-[2-(4-methanesulfonamidobenzenesulfonamido)ethyl]-5-methyl-7-(thien-2-yl)thieno[2,3-c]pyridine Hydrochloride Prepared by Method F using the aminobenzene compound in Example 11 9 and methanesulfonyl chloride. The title compound was isolated in 81% yield after flash silica gel chromatography using 0.5-2% MeOH in $CH_2Cl_2$. This material was treated with HCl/2-propanol (1.1 eq) to afford the title compound as a tan solid; mp 144.5°-147 C; IR (KBr) 3270, 3100, 2920, 2850, 1600, 1500, 1330 and 1150 cm$^{-1}$.

Anal. Calc'd for $C_{21}H_{25}N_3O_4S_4$.HCl: C, 46.03; H, 4.78; N, 7.67. Found: C, 46.04; H, 5.06; N, 7.36.

EXAMPLE 146 cis-4,5,6,7-Tetrahydro-7-methyl-6-[2-(4-methanesulfonamidobenzamido)ethyl]-5-propylthieno[2,3-c]pyridine Monooxalate Prepared by Method F using the aminobenzene compound in Example 120 and methanesulfonyl chloride. The title compound was isolated in 86% yield after flash silica gel chromatography using 0.5-4.5% MeOH in $CH_2Cl_2$. This material was treated with oxalic acid (1.1eq) in acetone/ether to afford the title compound as an off-white solid; mp 171.5°-173° C.; IR (KBr) 2940, 2600,1750, 1640, 1510, 1340 and 1150 cm$^{-1}$.

Anal. Calc'd for $C_{21}H_{29}N_3O_3S_2.C_2H_2O_4$: C, 52.56; H, 5.95; N, 8.00. Found: C, 52.50; H, 5.59; N, 7.75.

EXAMPLE 147 cis-4,5,6,7-Tetrahydro-6-[3-(4-methanesulfonamidobenzamido)propyl]-7-methyl-5-propylthieno[2,3-c]pyridine Hydrochloride Prepared by Method F using the aminobenzene compound in Example 121 and methanesulfonyl chloride. The title compound was isolated in 81 % yield after flash silica gel chromatography using 0.5-4% MeOH in $CH_2Cl_2$. This material was treated with HCl/2-propanol (1.1eq) to afford the title compound as an off-white solid; mp 137°-141° C.; IR (KBr) 3270, 2960, 2930, 2570, 1630, 1610, 1500, 1340, 1150, 965, 925 and 855 cm$^{-1}$.

Anal. Calc'd for $C_{22}H_{31}N_3O_3S_2.HCl.\frac{1}{4}C_3H_8O$: C, 54.69; H, 7.03; N, 8.14. Found: C, 54.81; H, 7.29; N, 7.83.

EXAMPLE 148 cis-4,5,6,7-Tetrahydro-6-[2-(4-methanesulfonaminobenzamido)ethyl]-4,7-dimethylthieno[2,3-c]pyridine Hydrochloride Prepared by Method F using the aminobenzene compound in Example 122 and methanesulfonyl chloride. The title compound was isolated in 30% yield after the crude product was treated with HCl/2-propanol (1.1eq). There was obtained a red crystalline solid; mp 195°-203° C.; IR (KBr) 1646, 1642, 1609, 1505,1333, 1309 and 1153 cm$^{-1}$.

Anal. Calc'd for $C_{19}H_{25}N_3O_3S_2$.HCl: C, 51.40; H, 5.92; N, 9.46. Found: C, 51.59; H, 6.13; N, 9.38.

EXAMPLE 149 trans-4,5,6,7-Tetrahydro-6-[2-(4-methanesulfonaminobenzamido)ethyl]-4,7-dimethylthieno-[2,3-c]pyridine Hydrochloride A $CH_2Cl_2$ solution (3 mL) of the aminobenzene compound in Example 123 (0.6 g, 1.83 mmol) was treated with methanesulfonyl chloride (0. 1 7 mL, 2.2 mmol), a catalytic amount of pyridine and enough ether to make the solution cloudy. The mixture was stirred for 30 min, filtered and the filtrate was condensed in vacuo. The residue was dried under high vacuum to afford the title compound directly as its hydrochoride salt as a pink foam (0.4 g, 47%); MH+ at m/z 408; mp 236°-244° C.; IR (KBr) 1506,1334,1153, 427 and 406 cm$^{-1}$.

Anal. Calc'd for $C_{19}H_{25}N_3O_3S_2.HCl.H_2O$: C, 50.38; H, 6.03; N, 9.27. Found: C, 50.44; H, 6.25; N, 9.33.

EXAMPLE 150 cis-6-[2-(4-Chloromethanesulfonamidobenzamido)ethyl]-4,5,6,7-tetrahydro-5,7-dimethylthieno[2,3-c]pyridine Monooxalate Prepared by Method F using the aminobenzene compound in Example 102 and chloromethanesulfonyl chloride. The title compound was isolated in 96% yield after flash silica gel chromatography using 1-4% MeOH in $CH_2Cl_2$. This material was treated with oxalic acid (1.1 eq) in acetone to afford the title compound as a tan solid; mp 208°-210° C.; IR (KBr) 3370, 3110, 3050, 2930, 1660, 1610, 1540, 1500, 1350 and 1160 cm$^{-1}$.

Anal. Calc'd for $C_{19}H_{24}ClN_3O_3S_2.C_2H_2O_4$: C, 47.42; H, 4.93; N, 7.90. Found: C, 47.84; H, 4.86; N, 7.59.

EXAMPLE 151 cis-6-[2-(4-Ethanesulfonamidobenzamido)ethyl]-4,5,6,7-tetrahydro-5,7-dimethylthieno[2,3-c]pyridine Monooxalate Prepared by Method F using the aminobenzene compound in Example 102 and ethanesulfonyl chloride. The title compound was isolated in 76% yield after flash silica gel chromatography using 3-4% MeOH in $CH_2Cl_2$. This material was treated with oxalic acid (1.1 eq) in acetone to afford the title compound as an off-white solid; mp 200°-202° C.; IR (KBr) 3340, 3040, 2920, 1660, 1540, 1500, 1330 and 1140 cm$^{-1}$.

Anal. Calc'd for $C_{20}H_{27}N_3O_3S_2.C_2H_2O_4$: C, 51.66; H, 5.72; N, 8.22. Found: C, 52.04; H, 5.63; N, 8.05.

EXAMPLE 152 cis-6-[2-(4-Butanesulfonamidobenzamido)ethyl]-4,5,6,7-tetrahydro-5,7-dimethylthieno[2,3-c]pyridine Monooxalate Prepared by Method F using the aminobenzene compound in Example 102 and 1-butanesulfonyl chloride. The title compound was isolated in 86% yield after flash silica gel chromatography using 3-5% MeOH in $CH_2Cl_2$. This material was treated with oxalic acid (1.1 eq) in acetone to afford the title compound as a light orange solid; mp 182°–184.5° C.; IR (KBr) 3060, 2850, 2790, 2450, 1710, 1600, 1460, 1350, 1290, 1190, 1100 and 890 $cm^{-1}$.

Anal. Calc'd for $C_{20}H_{27}N_3O_3S_2 \cdot C_2H_2O_4$: C, 53.42; H, 6.17; N, 7.79. Found: C, 53.52; H, 6.39; N, 7.78.

EXAMPLE 153 cis-6-{2-[4-(4-Chlorobenzenesulfonamido)benzamido]ethyl}-4,5,6,7-tetrahydro-5,7-dimethylthieno[2,3-c]pyridine Prepared by Method F using the aminobenzene compound in Example 102 and 4-chlorobenzenesulfonyl chloride. The title compound was isolated in 89% yield after flash silica gel chromatography using 0.5-5% MeOH in $CH_2Cl_2$. This material was crystallized from $CH_2Cl_2$/ether/hexane to afford the title compound as an off-white solid; mp 107°–111° C.; IR (KBr) 3400, 3100, 2970, 2920, 1630, 1610, 1500, 1340, 1160 and 1090 $cm^{-1}$.

Anal. Calc'd for $C_{24}H_{26}ClN_3O_3S_2$: C, 57.20; H, 5.20; N, 8.34. Found: C, 57.40; H, 5.34; N, 8.36.

EXAMPLE 154 cis-4,5,6,7-Tetrahydro-5,7-dimethyl-6-(2-[4-(methanesulfonyl-N-methylamino)benzamido]ethyl)-thieno[2,3-c]pyridine Hydrochloride A DMF solution (50 mL) of the methanesulfonamide from Example 130 (1.4 g, 3.44 mmol) at 0° C. under nitrogen was treated with 60% NaH in mineral oil (0.15 g, 3.78 mmol). After stirring for 15-20 min, the solution was treated with MeI (0.24 mL, 3.78 mmol) and allowed to warm to rt. The DMF was removed in vacuo and the residue was slurried in water. This mixture was extracted with $CH_2Cl_2$ and the combined extract was washed with water and dried ($MgSO_4$). Solvent removal produced the crude product that was purified by flash silica gel column chromatography using 2% MeOH in $CH_2Cl_2$. The title compound was collected (0.65 g, 36%) and then treated with HCl/2-propanol to produce a light beige solid; 115° C. (softens), 200°–204° C.; IR (KBr) 3400, 3250, 2920, 1645, 1490, 1330 and 1140 $cm^{-1}$.

Anal. Calc'd for $C_{20}H_{27}N_3O_3S_2 \cdot HCl$: C, 52.44; H, 6.16; N, 9.17. Found: C, 52.35; H, 6.28; N, 8.82.

EXAMPLE 155

4,5,6,7-Tetrahydro-5-[2-(4-nitrobenzamido)ethyl]-thieno[3,2-c]pyridine Monooxalate The title compound was prepared by Method A using the amine 9t (Table VI) and 4-nitrobenzoyl chloride to produce the desired product in 100% yield. This material was treated with oxalic acid (1.1 eq) in acetone/MeOH to afford an off-white solid; mp 201°–204° C.; IR (KBr) 3440, 3050, 1740, 1510, 1340 and 1210 $cm^{-1}$.

Anal. Calc'd for $C_{16}H_{17}N_3O_3S \cdot C_2H_2O_4 \cdot \frac{1}{2}H_2O$: C, 50.22; H, 4.68; N, 9.76. Found: C, 50.12; H, 4.56; N, 9.31.

EXAMPLE 156 cis-4,5,6,7-Tetrahydro-4,6-dimethyl-5-[2-(4-nitrobenzamido)ethyl]-thieno[3,2-c]pyridine Hydrochloride The title compound was prepared by Method A using the amine 9u-cis (Table VI) and 4-nitrobenzoyl chloride to produce the desired product in 31% yield. This material was treated with HCl/2-propanol (1.1 eq) to afford a tan solid; mp 229.5°–232° C.; IR (KBr) 3250, 2500, 1670, 1600, 1540, 1340 and 1290 $cm^{-1}$.

Anal. Calc'd for $C_{18}H_{21}N_3O_3S \cdot HCl$: C, 54.61; H, 5.60; N, 10.62. Found: C, 54.50; H, 5.66; N, 10.72.

EXAMPLE 157 trans-4,5,6,7-Tetrahydro-4,6-dimethyl-5-[2-(4-nitrobenzamido)ethyl]thieno[3,2-c]pyridine Hydrochloride In one of the preparations of Example 156, the amine was a mixture of 9u-cis and 9u-trans. The column chromatography purification step of Method A afforded the title compound in 18% yield. This material was treated with HCl/2-propanol (1.1 eq) to afford a beige solid; IR (KBr) 1667, 1603, 1525, 1347 and 1297 $cm^{-1}$.

EXAMPLE 158 cis-2-Chloro-4,5,6,7-tetrahydro-4,6-dimethyl-5-[2-(4-nitrobenzamido)ethyl]thieno[3,2-c]pyridine Hydrochloride The title compound was prepared by the procedure described in Example 75 starting with the nitro compound in Example 156. The crude material was purified by flash silica gel column chromatography using 0.5-3.5% MeOH in $CH_2Cl_2$ to afford the title compound in 42% yield. This material was treated with HCl/2-propanol (1.1 eq) to produce a tan solid; mp 118° C. (shrinks), 122√–125° C; IR 3250, 2460, 1660, 1590, 1520, 1340, 1280 and 710 $cm^{-1}$.

Anal. Calc'd for $C_{18}H_{20}ClN_3O_3S \cdot HCl$: C, 50.24; H, 4.92; N, 9.76. Found: C, 49.93; H, 4.88; N, 9.35.

EXAMPLE 159 cis-2-Bromo-4,5,6,7-tetrahydro-4,6-dimethyl-5-[2-(4-nitrobenzamido)ethyl]thieno[3,2-c]pyridine Hydrochloride The title compound was prepared by the procedure described in Example 76 starting with the nitro compound in Example 156. The crude material was purified by flash silica gel column chromatography using 0.5-2% MeOH in $CH_2Cl_2$ to afford the title compound as a brown oil in 56% yield. This material was treated with HCl/2-propanol (1.1 eq) to produce a tan solid; mp 274°–276° C.; IR (KBr) 3270, 2470, 1670, 1600, 1550, 1530, 1340, 1290, 1195, 870, 820 and 715 $cm^{-1}$.

Anal. Calc'd for $C_{18}H_{20}BrN_3O_3S \cdot HCl$: C, 45.53; H, 4.46; N, 8.85. Found: C, 45.63; H, 4.40; N, 8.72.

EXAMPLE 160 cis-4,5,6,7-Tetrahydro-4,6-dimethyl-2-nitro-5-[2-(4-nitrobenzamido)ethyl]thieno[3,2-c]pyridine Hydrochloride The title compound was prepared by the procedure described in Example 77 starting with the nitro compound in Example 156. The crude material was purified by flash silica gel column chromatography using 1-2.5% MeOH in $CH_2Cl_2$ to afford the title compound as a green oil in 97% yield. This material was treated with HCl/2-propanol (1.1 eq) to produce a tan solid; mp 209°–210.5° C.; IR (KBr) 3250, 2470, 1650, 1600, 1545, 1525, 1500, 1430, 1345, 1325, 1210, 1135, 1010, 865, 855 and 715 cm$^{-1}$.

Anal. Calc'd for $C_{18}H_{20}N_4O_5S.HCl$: C, 49.04; H, 4.80; N, 12.71. Found: C, 49.24; H, 4.83; N, 12.45.

EXAMPLE 161 cis-4,5,6,7-Tetrahydro-4,6-dimethyl-5-[2-(4-nitrophenoxy)ethyl]thieno[3,2-c]pyridine The title compound was prepared by the procedure described in Example 78 starting with the amino compound 9u-cis. Solvent removal produced the crude product that was purified by flash silica gel chromatography using 5% EtOAc in $CH_2Cl_2$ to afford a yellow oil (40%). This material was used directly in the reduction step (Example 165).

EXAMPLE 162 cis-5-[2-(4-Aminobenzamido)ethyl]-4,5,6,7-tetrahydro-4,6-dimethylthieno[3,2-c]pyridine Prepared by Method C using the nitro compound in Example 156 and isolated in 33% yield after silica gel column chromatography using 4% MeOH in $CH_2Cl_2$. There was obtained a tan oil; MH+ at m/z 330; IR (KBr) 3360, 3000, 1635, 1610, 1510, 1305, 1295, 1195, 850, 780 and 700 cm$^{-1}$.

EXAMPLE 163 trans-5-[2-(4-Aminobenzamido)ethyl]-4,5,6,7-tetrahydro-4,6-dimethylthieno[3,2-c]pyridine Prepared by Method C using the nitro compound in Example 157 and isolated in 85% yield as a light yellow foam; MH+ at m/z 330.

EXAMPLE 164 cis-5-[2-(4-Aminobenzamido)-2-bromo-4,5,6,7-tetrahydro-4,6-dimethylethyl]thieno[3,2-c]pyridine Prepared by Method C using the nitro compound in Example 159 and isolated in 80% yield after silica gel column chromatography using 0.5–4% MeOH in $CH_2Cl_2$. There was obtained an oil; MH+ at m/z 408; IR (KBr) 3340, 2970, 1640, 1500, 1285, 1185, 905, 835 765 and 730 cm$^{-1}$.

EXAMPLE 165 cis-5-[2-(4-Aminophenoxy)ethyl]-4,5,6,7-tetrahydro-4,6-dimethylthieno[3,2-c]pyridine Prepared by Method D using the nitro compound in Example 161 and isolated in 64% yield as a black brown oil.

EXAMPLE 166 cis-4,5,6,7-Tetrahydro-5,7-dimethyl-6-[2-(4-methanesulfonamidobenzamido)ethyl]thieno[3,2-c]pyridine Monooxalate Prepared by Method F using the aminobenzene compound in Example 162 and methanesulfonyl chloride. The title compound was isolated in 91 % yield after flash silica gel chromatography using 0.5–4.5% MeOH in $CH_2Cl_2$. This material was dissolved in acetone and treated with oxalic acid (1.1 eq) to afford the title compound as an off-white solid; mp 213°–214.5° C.; IR (KBr) 3380, 3110, 3050, 2940, 1710, 1655, 1640, 1605, 1500, 1335, 1230, 1150, 975, 960, 905, 855, 770 and 730 cm$^{-1}$.

Anal. Calc'd for $C_{19}H_{25}N_3O_3S_2.C_2H_2O_4$: C, 50.70; H, 5.47; N, 8.45. Found: C, 50.83; H, 5.46; N, 8.24.

EXAMPLE 167 trans-4,5,6,7-Tetrahydro-5,7-dimethyl-6-[2-(4-methanesulfonamidobenzamido)ethyl]thieno[3,2-c]pyridine Prepared by Method F using the aminobenzene compound in Example 162 and methanesulfonyl chloride. The title compound was isolated in 94% yield after flash silica gel chromatography using 1–5% MeOH in $CH_2Cl_2$. This material was isolated as a white foamy solid; mp 67°–74° C.; IR (KBr) 3390, 2970, 2910, 1645, 1630, 1610, 1500, 1335, 1300, 1150, 965, 915, 850, 765 and 670 cm$^{-1}$.

Anal. Calc'd for $C_{19}H_{25}N_3O_3S_2$: C, 55.99; H, 6.18; N, 10.31. Found: C, 55.91; H, 6.32; N, 10.15.

EXAMPLE 168 cis-2-Bromo-4,5,6,7-tetrahydro-5-[2-(4-methanesulfonamidobenzamido)ethyl]-4,6-dimethylthieno[3,2-c]pyridine Hydrochloride Prepared by Method F using the aminobenzene compound in Example 164 and methanesulfonyl chloride. The title compound was isolated in 74% yield after flash silica gel chromatography using 1–3.5% MeOH in $CH_2Cl_2$. This pink foamy material was treated with HCl/2-propanol to afford a tan solid; mp 157°–160° C.; IR (KBr) 3260, 2920, 2580, 1645, 1605, 1500, 1330, 1300, 1145, 965, 910, 850 and 765 cm$^{-1}$.

Anal. Calc'd for $C_{19}H_{24}BrN_3O_3S_2.HCl.\frac{1}{4}H_2O$: C, 43.27; H, 4.87; N, 7.97. Found: C, 43.55; H, 4.84; N, 7.58.

EXAMPLE 169 cis-4,5,6,7-Tetrahydro-5-[2-(4-methanesulfonylaminophenoxy)ethyl]-4,6-dimethylthieno[3,2-c]pyridine Hydrochloride Prepared by Method F using the aminobenzene compound in Example 165 and methanesulfonyl chloride (without pyridine added). The title compound was isolated as its hydrochloride salt in 25% yield (light brown solid); mp 213°–216° C.; MH+ at m/z 381; IR (KBr) 3060, 1510, 1330, 1150 and 974 cm$^{-1}$.

Anal. Calc'd for $C_{18}H_{24}N_2O_3S_2.HCl.\frac{1}{4}H_2O$: C, 51.31; H, 6.09; N, 6.64. Found: C, 51.18; H, 6.08; N, 6.52.

EXAMPLE 170 cis-1-Chloro-4,5,6,7-tetrahydro-4,6-dimethyl-5-[2-(4-nitrobenzamido)ethyl]thieno[3,4-c]pyridine Hydrochloride The title compound was prepared by Method A using the amine 9v-cis (Table VI) and 4-nitrobenzoyl chloride to produce the desired product in 66% yield. This material was treated with HCl/2-propanol (1.1 eq) to afford a yellow solid; mp 251°–252° C. (dec); IR (KBr) 3270, 2490, 1665, 1600, 1550, 1525, 1450, 1340, 1290, 1110, 1025, 875, 825 and 720 cm$^{-1}$.

Anal. Calc'd for $C_{18}H_{20}ClN_3O_3S.HCl$: C, 50.24; H, 4.92; N, 9.76. Found: C, 50.67; H, 5.05; N, 9.31.

EXAMPLE 171 trans-1-Chloro-4,5,6,7-tetrahydro-4,6-dimethyl-5-[2-(4-nitrobenzamido)ethyl]thieno[3,4-c]pyridine Hydrochloride The title compound was prepared by Method A using the amine 9v-trans (Table VII) and 4-nitrobenzoyl chloride to produce the desired product as a yellow gummy material in 25% yield. This material was treated with HCl/2-propanol (1.1 eq) to afford a beige solid; mp 205°-207° C.; IR (KBr) 3390, 2460, 1660, 1600, 1525, 1345, 1290, 1180, 1105, 865, 825, 760, 725, 645 and 620 cm$^{-1}$.

Anal. Calc'd for $C_{18}H_{20}ClN_3O_3S \cdot HCl$: C, 50.24; H, 4.92; N, 9.76. Found: C, 50.22; H, 4.84; N, 9.36.

EXAMPLE 172 cis-5-[2-(4-Aminobenzamido)ethyl]-1-chloro-4,5,6,7-tetrahydro-4,6-dimethylthieno[3,4-c]pyridine Prepared by Method C using the nitro compound in Example 170 and isolated in 63% yield after silica gel column chromatography using 2-3% MeOH in $CH_2Cl_2$. There was obtained a light yellow oil; MH+ at m/z 364.

EXAMPLE 173 cis-2-Chloro-4,5,6,7-tetrahydro-4,6-dimethyl-5-[2-(4-methanesulfonamidobenzamido)ethyl]thieno[3,4-c]pyridine Prepared by Method F using the aminobenzene in Example 172 and methanesulfonyl chloride. The title compound was isolated in 53% yield after flash silica gel chromatography using 2-4% MeOH in $CH_2Cl_2$ to afford the title compound as a white foamy solid; mp 74°-86° C.; IR (KBr) 3400, 2960, 2930, 1645, 1635, 1610, 1500, 1330, 1300, 1150, 965 and 765 cm$^{-1}$.

Anal. Calc'd for $C_{19}H_{24}ClN_3O_3S_2 \cdot \frac{1}{4}H_2O$: C, 51.11; H, 5.53; N, 9.41. Found: C, 51.03; H, 5.48; N, 9.28.

EXAMPLE 174

1,2,3,4-Tetrahydro-2-[2-(4-nitrobenzamido)ethyl]isoquinoline

The title compound was prepared in a multistep sequence, starting with 1,2,3,4-tetrahydroisoquinoline.

2-Cyanomethyl-1,2,3,4-tetrahydroisoquinoline

This material was prepared in the same fashion as described in the above "General Procedure for the Preparation of Cyanomethyl Compounds 7A or 24A from Cyclic Amines 7 or 24". The title compound was isolated as a red-brown oil in 81% yield; MH+ at m/z 173; IR (neat) 3078, 3036, 2927, 2818, 2765, 2260, 1628, 1499, 1452, 1320 and 748 cm$^{-1}$.

2-(2-Aminoethyl)-1,2,3,4-tetrahydroisoquinoline

This material was prepared in the same fashion as described in the above "General Procedure for the Preparation of Aminoethyl Compounds 9 or 25". The title compound was isolated as a brown oil in 100% yield; MH+ at m/z 177; IR (neat) 3395, 2924, 2799, 2241, 2200, 1582, 1491, 1446, 1261, 1094 and 651 cm$^{-1}$.

The title compound was prepared by Method A using the amine above and 4-nitrobenzoyl chloride. This material was purified by flash silica gel column chromatography using 20-30% EtOAc in hexane and by crystallization from acetone/ether/hexane to afford a mustard-colored solid (30%); mp 105°-109° C.; IR (KBr) 3317, 3065, 2805, 1635, 1593, 1518, 1339, 1093 and 738 cm$^{-1}$.

Anal. Calc'd for $C_{18}H_{19}N_3O_3$: C, 66.47; H, 5.89; N, 12.91. Found: C, 66.33; H, 5.73; N, 12.86.

EXAMPLE 175

1,2,3,4-Tetrahydro-2-[2-(4-nitrophenylsulfonamido)ethyl]isoquinoline

The title compound was prepared by Method A using 2-(2-aminoethyl)-1,2,3,4-tetrahydroisoquinoline (described in Example 174) and 4-nitrobenzenesulfonyl chloride to produce the desired product in 98% yield. This material was crystallized from EtOAc to afford a gold-colored solid; mp 142.5°-144.5° C.; IR (KBr) 3372, 3110, 2778, 1929, 1603, 1521, 1305, 1151, 969 and 739 cm$^-$.

Anal. Calc'd for $C_{17}H_{19}N_3O_4S$: C, 56.52; H, 5.30; N, 11.63. Found: C, 56.58; H, 5.10; N, 11.56.

EXAMPLE 176

1,2,3,4-Tetrahydro-6,7-dimethoxy-2-[2-(4-nitrobenzamido)ethyl]isoquinoline

The title compound was prepared in a multistep sequence, starting with 1,2,3,4-tetrahydro-6,7-dimethoxyisoquinoline.

2-Cyanomethyl-1,2,3,4-tetrahydro-6.7-dimethoxyisoquinoline

This material was prepared in the same fashion as described in the above "General Procedure for the Preparation of Cyanomethyl Compounds 7A or 24A from Cyclic Amines 7 or 24". The title compound was isolated as a dark solid in 85% yield; IR (KBr) 2999, 2942, 2841, 2228, 1611, 1518, 1463, 1381, 1222, 1129, 865 and 400 cm$^{-1}$.

2-(2-Aminoethyl)-1,2,3,4-tetrahydro-6,7-dimethoxyisoquinoline

This material was prepared in the same fashion as described in the above "General Procedure for the Preparation of Aminoethyl Compounds 9 or 25". The title compound was isolated as a brown oil in 84% yield; IR (KBr) 2939, 2839, 2248, 1611, 1512, 1460, 1262, 1223, 917 and 648 cm$^{-1}$.

The title compound was prepared by Method A using the amine above and 4-nitrobenzoyl chloride. This material was purified by flash silica gel column chromatography using 50% $CH_2Cl_2$ in hexane and by crystallization from ether/hexane to afford an orange solid (36%); mp 59 (shrinks) 63°-64.5° C.; IR (KBr) 3357, 2930, 1658, 1498, 1518, 1343, 1254, 1011, 842 and 720 cm$^{-1}$.

Anal. Calc'd for $C_{20}H_{23}N_3O_5$: C, 62.33; H, 6.02; N, 10.90. Found: C, 62.24; H, 6.09; N, 10.59.

EXAMPLE 177

6,7-Dimethoxy-1,2,3-tetrahydro-2-[2-(4-nitrophenyisulfonamido)ethyl]isoquinoline The title compound was prepared by Method A using 2-(2-aminoethyl)-1,2,3,4-tetrahydro-6,7-dimethoxyisoquinoline (described in Example 176) and 4-nitrobenzenesulfonyl chloride to produce the desired product in 70% yield. This material was purified by flash silica gel chromatography using 40-60% EtOAc in hexane. The material obtained was then crystallized from $CH_2Cl_2$/hexane/ether to afford a bright yellow solid; mp 145.5°-147.5° C.; IR (KBr) 3237, 2939, 1608, 1521, 1345, 1253, 1159, 1012, 735, 621 and 462 cm, Anal. Calc'd for $C_{19}H_{23}N_3O_6S$: C, 54.17; H, 5.50; N, 9.97. Found: C, 54.33; H, 5.65; N, 9.60.

EXAMPLE 178

1,2,3,4-Tetrahydro-6-methoxy-1-methyl-2-[2-(4-nitrobenzamido)ethyl]isoquinoline Hydrochloride The title compound was prepared in a multistep sequence, starting with 3-methoxyphenethylamine.
N-Acetyl-3-methoxyphenethylamine This material was prepared in the same fashion as described in the above "General Procedure for the Preparation of Amides 6". The title compound was isolated as a yellow oil in 82% yield; MH+ at m/z 194.
1,2,3,4-Tetrahydro-6-methoxy-1-methylisoguinoline Hydrochloride This material was prepared in the same fashion as described in the above "General Procedure for the Preparation of Cyclic Amines 7 from Amides 6". The title compound was isolated in 66% yield and a portion of this material was treated with HCl/2-propanol (1.1 eq) to afford an off-white solid; mp 220° C. (shrinks) 223°-224° C.; IR (KBr) 2940, 2780, 2500, 1610, 1580,1500,1450,1425,1280,1260,1130,1050,1025,885,860-,810,495 and 420 cm$^{-1}$.

Anal. Calc'd for $C_{11}H_{15}NO.HCl$: C,61.83;H,7.55;N,6.56. Found: C, 61.66; H, 7.63; N, 6.49.

2-Cyanomethyl-1,2,3,4-tetrahydro-6-methoxy-1-methylisoguinoline

This material was prepared in the same fashion as described in the above "General Procedure for the Preparation of Cyanomethyl Compounds 7A or 24A from Cyclic Amines 7 or 24". The crude material was purified by flash silica gel column chromatography using 30% $CH_2Cl_2$ in hexane. The title compound was collected (65% yield) and recrystallized from ether/hexane to afford a white solid; mp 88°-90.5° C.; IR (KBr) 2950, 2820, 1615, 1505, 1460, 1445, 1425, 1180, 1275, 1255, 1150, 1040, 870, 815, 745, 620 and 475 cm$^{-1}$.

Anal. Calc'd for $C_{13}H_{16}N_2O$: C, 72.24; H, 7.46; N, 12.96. Found: C, 71.90; H, 7.62; N, 12.82.
2-(2-Aminoethyl)-1,2,3,4-tetrahydro-6-methoxy-1-methylisoguinoline This material was prepared in the same fashion as described in the above "General Procedure for the Preparation of Aminoethyl Compounds 9 or 25". The title compound was isolated in 73% yield as a brown oil; MH+ at m/z 221; IR (neat) 3360, 2970, 2930, 2830, 1610, 1500, 1270, 1245, 1140, 1035 and 815 cm$^{-1}$.

The title compound was prepared by Method A using the amine above and 4-nitrobenzoyl chloride. This material was isolated in 74% yield after flash silica gel column chromatography using 80–100% EtOAc in hexane This material was treated with HCl/2-propanol (1.1 eq) to afford a tan solid; mp 159°–163° C.; IR (KBr) 3242, 2473, 1670, 1613, 1605, 1551, 1524, 1507, 1432, 1347, 1297, 1277, 1260, 1249 and 1032 cm$^{-1}$.

Anal. Calc'd for $C_{20}H_{23}N_3O_4.HCl$: C, 59.18; H, 5.96; N, 10.35. Found: C, 59.25; H, 5.70; N, 10.39.

EXAMPLE 179

1,2,3,4-Tetrahydro-6-methoxy-1-methyl-2-[2-(4-nitrophenyisulfonamido)ethyl]isoquinoline Hydrochloride The title compound was prepared by Method A using 2-(2-aminoethyl)-1,2,3,4-tetrahydro-6-methoxy-1-methylisoquinoline (described in Example 178) and 4-nitrobenzenesulfonyl chloride to produce the desired product in 100% yield. This material was purified by flash silica gel chromatography using 10–100% EtOAc in hexane. The material obtained was treated with HCl/2-propanol (1.1 eq) to afford a beige solid; mp 167°–172° C.; IR (KBr) 1611, 1531,1507,1443,1347,1309,1248,1232,1168,1092,1029,85-2,745,739 and 607 cm$^{-1}$.

Anal. Calc'd for $Cl_9H_{23}N_3O_5S.HCl$: C, 51.63; H, 5.47; N, 9.50. Found: C, 51.78; H, 5.12; N, 9.40.

EXAMPLE 180

2-[2-(4-Aminobenzamido)ethyl]-1,2,3,4-tetrahydroisoquinoline

Prepared by Method D using the nitro compound in Example 174 and isolated in 45% yield. There was obtained a clear oil; MH+ at m/z 296.

EXAMPLE 181

2-[2-(4-Aminophenyisulfonamido)ethyl]-1,2,3,4-tetrahydroisoquinoline

Prepared by Method C using the nitro compound in Example 175 and isolated in 93% yield. There was obtained a clear oil; MH+ at m/z 332.

EXAMPLE 182

2-[2-(4-Aminobenzamido)ethyl]-1,2,3,4-tetrahydro-6,7-dimethoxyisoquinoline

Prepared by Method D using the nitro compound in Example 176 and isolated in 31 % yield. There was obtained a yellow tacky oil; MH+ at m/z

EXAMPLE 183

2-[2-(4-Aminophenyisulfonamido)-6,7-dimethoxy-1,2,3-tetrahydroethyl]isoquinoline Prepared by Method C using the nitro compound in Example 177 and isolated in 87% yield. There was obtained a caramel-colored tacky solid;

EXAMPLE 184

2-[2-(4-Aminophenyisulfonamido)ethyl]-1,2,3,4-tetrahydro-6-methoxy-1-methylisoquinoline Prepared by Method D using the nitro compound in Example 179 and isolated in 38% yield. There was obtained a yellow tacky oil.

EXAMPLE 185

1,2,3,4-Tetrahydro-2-[2-(4-methanesulfonimidobenzamido)ethyl]isoquinoline

Prepared by Method F using the aminobenzene compound in Example 180 and methanesulfonyl chloride. The crude material was purified by flash silica gel chromatography using 10% MeOH in EtOAc and MeOH/NH$_4$OH (9.5/0.5) in EtOAc. This material was crystallized from $CH_2Cl_2$/hexane/ether to afford a beige solid (20%); mp 156°–158° C.; IR (KBr) 3423, 3157, 2934, 1639, 1496, 1333, 1145, 967, 920, 756 and 505 cm$^{-1}$.

Anal. Calc'd for $Cl_9H_{23}N_3O_3S$: C, 61.14; H, 6.21; N, 11.25. Found: C, 60.80; H, 6.47; N, 11.06.

EXAMPLE 186

1,2,3,4-Tetrahydro-2-[2-(4-methanesulfonamidobenzenesulfonamido)ethyl]isoquinoline Hemioxalate Prepared by Method F using the aminobenzene compound in Example 181 and methanesulfonyl chloride. The crude material was purified by flash silica gel chromatography using 40-100% EtOAc in hexane. This material was treated with oxalic acid (1.1 eq) in EtOH to afford a tan solid (1 4%); mp 224°-226° C. (dec); IR (KBr) 3263, 3016, 2550, 1607, 1501, 1316, 1142, 972, 828, 752 and 578 cm$^{-1}$.

Anal. Calc'd for $C_{18}H_{23}N_3O_4S_2 \cdot \frac{1}{2}C_2H_2O_4$: C, 50.22; H, 5.32; N, 9.24. Found: C, 50.43; H, 5.26; N, 8.99.

EXAMPLE 187

1,2,3,4-Tetrahydro-2-[2-(4-methanesulfonamidobenzamido)-ethyl]-6,7-dimethoxyisoquinoline 3/2 Oxalate Prepared by Method F using the aminobenzene compound in Example 182 and methanesulfonyl chloride. The crude material was purified by flash silica gel chromatography using 10-20% MeOH in EtOAc. This material was treated with oxalic acid (1.1 eq) in acetone to afford an off-white solid (17%); mp 175° C. (shrinks) 189° C. (dec); IR (KBr) 3408, 3188, 2935, 2588, 1717, 1639, 1498, 1114, 964 and 702 cm$^{-1}$.

Anal. Calc'd for $C_{21}H_{27}N_3O_5S \cdot 3/2 C_2H_2O_4$: C, 50.70; H, 5.32; N, 7.39. Found: C, 50.82; H, 5.41; N, 7.75.

EXAMPLE 188

1,2,3,4-Tetrahydro-2-[2-(4-methanesulfonimidobenzenesulfonamido)-ethyl]-6,7-dimethoxyisoquinoline 3/2 Oxalate Prepared by Method F using the aminobenzene compound in Example 182 and methanesulfonyl chloride. The crude material was purified by flash silica gel chromatography using 10-20% MeOH in EtOAc. This material was treated with oxalic acid (1.1 eq) in acetone to afford an orange solid (38%); mp 134° C. (shrinks) 160° C. (dec); IR (KBr) 3240, 2930, 2838, 1641, 1592, 1518, 1461, 1319, 1145 and 833 cm$^{-1}$.

Anal. Calc'd for $C_{21}H_{27}N_3O_5S \cdot 3/2 C_2H_2O_4$: C, 49.03; H, 5.48; N, 8.17. Found: C, 49.46; H, 5.42; N, 7.81.

EXAMPLE 189

1,2,3,4-Tetrahydro-6-methoxy-1-methyl-2-[2-(4-methanesulfonamidobenzamido)ethyl]isoquinoline Monooxalate Prepared by Method F using the aminobenzene compound in Example 182 and methanesulfonyl chloride. The crude material was purified by flash silica gel chromatography using 2-propanol/NH$_4$OH (1 9.5/0.5% to 19/1 %) in CH$_2$Cl$_2$. This material was treated with oxalic acid (1.1 eq) in acetone to afford a pale yellow solid (54%); mp 141°-142° C.; IR (KBr) 1645, 1611, 1507, 1339 and 1153 cm$^{-1}$.

Anal. Calc'd for $C_{21}H_{27}N_3O_4S \cdot C_2H_2O_4$: C, 54.43; H, 5.76; N, 8.28. Found: C, 54.74; H, 5.58; N, 8.22.

EXAMPLE 190

Biological Materials and Methods

A. General Procedure

Papillary muscles were dissected from the right ventricle of anesthetized male ferrets. The tendons of papillary muscles from the right ventricle were tied securely with a fine silk suture and then cut proximal to the tie. The distal connection of the muscle in the ventricular wall was cut and secured to a holder/stimulator. The tied tendon was attached to a force transducer (Grass FT-03) and the muscle was stretched to approximately 0.4 grams of tension. Papillary muscles were then placed in tissue baths containing 55 ml of Tyrode's solution of the following composition (mM): NaCl, 130.0; KCl, 4.0; MgCl$_2$, 1.0; NaHCO$_3$, 25.0; KH$_2$PO$_4$, 1.2; CaCl$_2$, 2.0; Dextrose, 11.0, pH 7.3, gassed with 5% CO$_2$-95% O$_2$. Temperature was normally 37° C. Isometric force was recorded during stimulation with constant current pulses (3 msec; 1.3×threshold) at frequencies between 0.2 and 3.3 Hz using platinum bipolar electrodes. Normally, 0.1 μM timolol was present continuously to prevent variations in tension produced by spontaneous or stimulation-induced release of catecholamines.

B. Measurement of Effective Refractory Period (ERP)

The ERP was determined using the extra-stimulus technique. Papillary muscles were paced using a trains of 20 or 10 basic stimuli (S1) at cycle lengths (S1-S1 interval) of 300 msec (3.33 Hz) and 1000 msec (1 Hz), respectively. Following each 20th or 10th basic contraction an extra-stimulus (S2) of equal intensity and duration was introduced at gradually decreasing coupling intervals (S1-S2 interval) until activation of the muscle failed to occur. The ERP was defined as the shortest S1-S2 interval in msec that produced activation of the muscle. Measurements were made to the nearest 2 msec decrement. The mean dose that produced a 20% increase in ERP is defined as ERP$_{20}$ and is reported in Example 191 (Table 1) in μM ($1 \times 10^{-6}$) units.

C. Measurement of Transmembrane Potential and Tension

Papillary muscles were pinned at the base to the SYLGARD® bottom of a 1.0 ml tissue bath. A silk suture was tied to the tendon and attached to a tension transducer (Grass FT-03) for measuring isometric force. Muscles were superfused at a rate of 5ml/minutes with Tyrode's solution of the following composition (mM): NaCl, 130.0; KCl, 4.0; MgCl$_2$, 1.0; NaHCO$_3$, 24.0; NaH$_2$PO$_4$, 1.0; CaCl$_2$, 1.8; Dextrose, 5.6, pH 7.3. gassed with 5% CO$_2$-95% O$_2$. Temperature was normally 35° C. Muscles were stimulated with constant current pulses (0.1-0.3 msec; 2×threshold) at frequencies between 0.2 and 3.3 Hz using platinum bipolar electrodes. Transmembrane action potentials were measured using standard microelectrode techniques. Glass micro-capillary pipettes filled with 3M KCl ($\approx$50 Mohms) were coupled to a high input-impedance, capacitance-neutralizing amplifier (e.g. WPI 773). Action potentials and isometric tension were displayed simultaneously on an oscilloscope (e.g. TEKTRONIX 11402, digital) and were analyzed using a computerized data acquisition system.

D. Compound Preparation

Test compounds were dissolved initially in dimethylsulfoxide (DMSO) at a stock concentration of $1 \times 10^{-2}$M and further dilutions were made directly in Tyrode's solution to achieve the final concentrations. Timolol was dissolved in water at a stock concentration of $1 \times 10^{-3}$M and was added directly to the bath Tyrode's solution to achieve a final concentration of $1 \times 10^{-7}$M. Test compounds were applied by serially increasing concentrations and measurements were taken at 15 minutes after addition of each concentration. The mean dose that produced a 20% increase in ERP is defined as ERP$_{20}$ and is reported in Example 191 (Table 1) in μM ($1 \times 10^{-6}$) units.

EXAMPLE 191

Summary Table of Preparation Methods and Biological Activity

| Example # | Proc. Method | ERP$_{20}$ ($\mu$M) |
|---|---|---|
| 1 | A | 1 |
| 3 | F | 1.7 |
| 4 | A | 1.5 |
| 5 | A | 1.1 |
| 6 | B | 15 |
| 9 | F | 0.35 |
| 10 | F | 0.6 |
| 11 | A | 1.5 |
| 13 | F | 4 |
| 14 | A | 30 |
| 16 | F | 0.13 |
| 17 | — | >100 |
| 19 | F | 4.4 |
| 20 | — | 4 |
| 21 | A | >100 |
| 23 | F | 0.15 |
| 24 | A | 0.5 |
| 26 | F | 1.1 |
| 27 | A | 1 |
| 28 | A | 0.2 |
| 29 | A | 0.4 |
| 30 | A | 1.8 |
| 31 | A | 3 |
| 32 | A | 0.6 |
| 33 | A | 0.24 |
| 34 | A | 3.5 |
| 35 | A | 2 |
| 36 | A | 1.5 |
| 37 | A | 7 |
| 38 | A | 2 |
| 39 | A | 0.65 |
| 40 | A | 1.9 |
| 41 | A | 1.2 |
| 42 | A | 0.9 |
| 43 | A | 2.5 |
| 44 | A | 0.33 |
| 45 | A | 0.28 |
| 46 | A | 2.5 |
| 47 | — | >100 |
| 48 | TMA | 13 |
| 49 | MA | 10 |
| 50 | MA | 1.8 |
| 51 | A | 0.7 |
| 52 | A | 12 |
| 53 | A | 5 |
| 54 | A | 3 |
| 55 | A | 1.5 |
| 56 | A | 5.3 |
| 57 | A | 2.5 |
| 58 | A | 1.5 |
| 59 | TMA | 33.5 |
| 60 | TMA | 37.5 |
| 61 | TMA | 15 |
| 62 | TMA | 1.0 |
| 63 | A | 0.52 |
| 64 | A | 3 |
| 66 | A | 2.5 |
| 67 | — | 0.25 |
| 68 | — | 2.25 |
| 69 | A | 0.07 |
| 70 | A | 0.6 |
| 71 | — | 1 |
| 72 | A | 0.15 |
| 73 | A | 0.28 |
| 74 | A | 0.3 |
| 75 | SOCl$_2$ | 6 |
| 76 | Br$_2$ | 1 |
| 77 | HNO$_3$ | 0.25 |
| 78 | — | 0.25 |
| 79 | A | 0.9 |
| 80 | A | 1.2 |
| 81 | SA | 10 |
| 82 | A | 0.5 |
| 83 | A | 3.5 |
| 84 | A | 30 |
| 85 | A | >100 |
| 86 | A | 0.6 |
| 87 | A | >100 |
| 88 | A | 30 |
| 89 | A | 16 |
| 90 | A | 200 |
| 91 | A | 3 |
| 92 | A | 2.5 |
| 93 | A | >100 |
| 94 | A | >100 |
| 95 | A | >100 |
| 96 | A | 2 |
| 97 | A | 0.35 |
| 98 | A | 1.2 |
| 99 | A | 0.4 |
| 100 | Et$_2$O/py | >100 |
| 101 | Et$_2$O/py | 4.25 |
| 102 | C(AcOH) | 2 |
| 104 | C | 2.8 |
| 105 | C | 5 |
| 106 | C | 11 |
| 108 | C | 0.6 |
| 118 | C | 14 |
| 119 | D | 6 |
| 124 | E | 1.7 |
| 125 | E | 4.5 |
| 126 | E | 20 |
| 127 | TFA anhy | 4.25 |
| 128 | E | 4.5 |
| 129 | E | 10 |
| 130 | F | 0.16 |
| 131 | F | 0.26 |
| 132 | F | 0.03 |
| 133 | F | 0.45 |
| 134 | F | 1.4 |
| 135 | F | 0.17 |
| 136 | F | 0.6 |
| 137 | F | 0.5 |
| 138 | F | 9.2 |
| 139 | F | 0.35 |
| 140 | F | 0.1 |
| 141 | F | 0.6 |
| 142 | F | 0.035 |
| 143 | F | 2 |
| 144 | F | 5 |
| 145 | F | 10 |
| 146 | F | 0.07 |
| 147 | F | 0.45 |
| 148 | F | >100 |
| 149 | — | 3.8 |
| 150 | F | 2.5 |
| 151 | F | 2.3 |
| 152 | F | 5 |
| 153 | F | 20 |
| 154 | NaH/DMF | 4 |
| 155 | A | 1.5 |
| 156 | A | 0.2 |
| 158 | SOCl$_2$ | 0.8 |
| 159 | Br$_2$ | 2.0 |
| 160 | HNO$_3$ | 0.3 |
| 166 | F | 0.5 |
| 167 | F | 3.1 |
| 168 | F | 0.9 |
| 169 | F | 0.22 |
| 170 | A | 0.15 |
| 171 | A | 0.5 |
| 173 | F | 8 |
| 174 | A | 0.25 |
| 175 | A | 0.4 |
| 176 | A | 0.25 |
| 177 | A | 1.7 |
| 178 | A | 5.0 |
| 179 | A | 1.8 |
| 185 | F | 0.25 |
| 186 | F | 0.3 |
| 187 | F | 1.4 |
| 188 | F | 4 |
| 189 | F | 1.4 |

The above test results demonstrate the utility of the compounds of the invention for increasing the effective refractory periods in a mammal, i.e. male ferrets. The prolongation of refractories is believed to be an effective means of preventing or terminating atrial and ventricular arrhythmias which in turn may inhibit sudden cardiac death.

Pharmaceutical compositions containing compounds of the invention may comprise one or more of the compounds of the present invention and a pharmaceutically acceptable and inert carrier in either solid or liquid form. Solid form preparations include powders, tablets, dispersible granules, capsules, etc. The carrier may also be one or more substances which act as diluents, flavoring agents, solubilizers, lubricants, suspending agents, binders, or tablet disintegrating agents as well as encapsulating materials. Suitable carriers are magnesium carbonate, magnesium stearate, talc, lactose, sugar, peptin, dextrin, starch, methylcellulose, sodium carboxymethylcellulose, and the like. Liquid form preparations include solutions which are suitable for oral or parenteral administration, or suspensions and emulsions suitable for oral administration.

Sterile water solutions of the active component or sterile solutions of the active components in solvents comprising water, ethanol, or propylene glycol are examples of liquid preparations suitable for parenteral administration. Sterile solutions may be prepared by dissolving the active component in the desired solvent system, then passing the resulting solution through a membrane filter to sterilize it, or alternatively, by dissolving the sterile compound in a previously sterilized solvent under sterile conditions. Aqueous solutions for oral administration can be prepared by dissolving the active compound in water and adding suitable flavorants, coloring agents, stabilizers and thickening agents as required. Aqueous suspensions for oral use can be made by dispersing the finely divided active component in water together with a viscous material such as a natural or synthetic gum, methylcellulose, sodium carboxymethylcellulose, and other suspending agents known to the pharmaceutical formulation art.

It is especially advantageous to formulate the aforementioned pharmaceutical compositions in unit dosage form for ease of administration and uniformity of dosage. The term "unit dosage form" as used herein refers to physically discrete units suitable as unit dosages, each unit containing a predetermined quantity of active ingredient calculated to produce the desired therapeutic effect in association with the required pharmaceutical carrier.

Various conventional techniques for preparing pharmaceutical compositions including solutions, suspensions, tablets or caplets can be employed, as would be known to those skilled in the art and as is disclosed for example by *Remington's Pharmaceutical Sciences*, Mack Publishing Co., Part 8 Chapters 76–93, "Pharmaceutical Preparations and Their Manufacture", pp. 1409–1677 (1985).

In therapeutic use as antiarrhythmic agents, the compounds utilized in the methods of this invention may be administered to a patient either orally or parenterally at amounts effective to increase the effective refractory periods which correspond to dosage levels of from about 50–500 mg per day and preferably about 50 mg per day. The dosages, however, may be varied depending upon the results of specific clinical testing, the requirements of the patient, the weight and age of the patient, the severity of the condition being treated, and the compound being employed. Determination of optimum dosages for a particular situation is within the skill of the art.

The scope of the present invention is not limited by the description, examples and suggested uses herein and modifications can be made without departing from the spirit on the invention. For example, additional medicaments or active components may be used in combination with the compounds of the invention. Further, the novel compounds of the invention may have other uses in addition to those described herein.

Applications of the compounds, compositions and methods of the present invention for medical or pharmaceutical uses can be accomplished by any clinical, medical, and pharmaceutical methods and techniques as are presently or prospectively known to those skilled in the art. Thus it is intended that the invention cover any modifications and variations of this invention provided that they come within the scope of the appended claims and their equivalents.

What is claimed is:

1. A compound of the following formula:

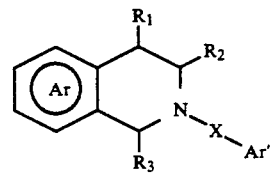

where

Ar' is selected from the group consisting of pyridine, thiophene, furan, pyrrole or

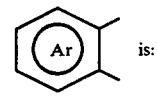  is:

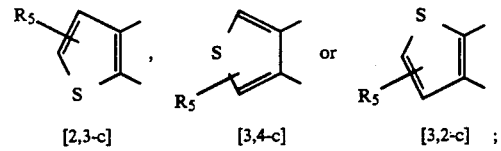

$R_1$ is hydrogen or $C_1$–$C_3$ alkyl;

$R_2$ is hydrogen, $C_1$–$C_6$ alkyl, $C_3$–$C_7$ branched chain alkyl;

$R_3$ is hydrogen, $C_1$–$C_6$ alkyl, $C_3$–$C_7$ branched chain alkyl, aryl or substituted aryl wherein the aryl substituents are $C_1$–$C_6$ alkyl or $C_1$–$C_6$ alkoxy;

$R_4$ is hydrogen, $C_1$–$C_5$ alkyl, $C_3$–$C_7$ branched chain alkyl, halogen, $C_1$–$C_3$ alkoxy, nitro, amino, imidazole, cyano, $CO_2R_1$, $SO_2R_1$, $CF_3$, $NHCOR_8$, $NR_7SO_2R_8$, $CH_2SO_2R_1$, $CH_2PO(OR_1)_2$ or $CH_2$-imidazole;

X is $(CH_2)_mNR_7CO$, $(CH_2)_mNR_7SO_2$ or $(CH_2)_mNHCH_2$;

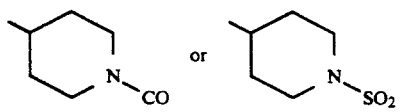

$R_5$ is hydrogen, halogen or nitro;
$R_7$ is hydrogen or $C_1$–$C_3$ alkyl;
$R_8$ is hydrogen, $CF_3$, $C_1$–$C_4$alkyl, $C_3$–$C_5$ branched chain alkyl, aryl or substituted aryl;
m is 2–4; and
when $R_1$ is alkyl and $R_2$ is hydrogen and when $R_1/R_3$ or $R_2/R_3$ are both alkyl; $R_1/R_3$ is cis or trans and $R_2/R_3$ is cis or trans

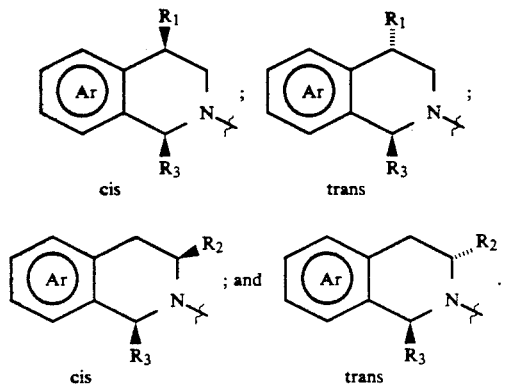

2. The compound according to claim 1 wherein:
$R_1$ is hydrogen or methyl;
$R_2$ is hydrogen or $C_1$–$C_4$ alkyl;
$R_3$ is hydrogen, $C_1$–$C_6$ alkyl, branched propyl, phenyl, thiophene or 4-methoxy-phenyl;
$R_4$ is hydrogen, chloro, fluoro, methyl, methoxy, nitro, amino, cyano, $NHCOCH_3$, $NHSO_2CH_3$ or $CO_2CH_3$;
$R_5$ may be hydrogen, halogen or nitro;
$R_7$ is hydrogen, methyl or ethyl;
$R_8$ is phenyl or substituted phenyl;
X is $(CH_2)_m NR_7 CO$, $(CH_2)_m NR_7 SO_2$ or $(CH_2)_m NHCH_2$;
$R_5$ is hydrogen, halogen or nitro; and
m is 2 or 3.

3. The compound according to claim 1 selected from the group consisting of:
4,5,6,7-Tetrahydro-6-[2-(6-nitrobenzamido)ethyl]-thieno[2,3-c]pyridine;
4,5,6,7-Tetrahydro-6-[2-(4-methanesulfonamidobenzamido)ethyl]thieno[2,3-c]pyridine;
4,5,6,7-Tetrahydro-5-methyl-6-[2-(4-nitrobenzamido)ethyl]thieno[2,3-c]pyridine;
5-Butyl-4,5,6,7-Tetrahydro-6-[2-(6-nitrobenzamido)ethyl]thieno[2,3-c]pyridine;
5-Butyl-4,5,6,7-Tetrahydro-6-[2-(4-methanesulfonamidobenzamido)ethyl]thieno[2,3-c]pyridine;
5-butyl-4,5,6,7-tetrahydro-6-[2,4methanesulfonamidobenzamido)ethyl]thieno[2,3-c]pyridine;
5-Butyl-4,5,6,7-tetrahydro-7-[2-(4-methanesulfonamidobenzenesulfonamido)ethyl]thieno[2,3-c]pyridine;
4,5,6,7-Tetrahydro-7-methyl-6-[2-(4-nitrobenzamido)ethyl]thieno[2,3-c]pyridine;
4,5,6,7-Tetrahydro-6-[2-(4-methanesulfonamidobenzamido)ethyl]-7methylthieno[2,3-c]pyridine;
7-Butyl-4,5,6,7-tetrahydro-6-2-(4-nitrobenzamido)ethyl]thieno[2,3-c]pyridine;
7-Butyl-4,5,6,7-tetrahydro-6-[3-(4-methanesulfonamidophenoxy)propyl]thieno[2,3-c]pyridine;
7-Butyl-4,5,6,7-tetrahydro-6-[2-(4-nitrobenzylamino)ethyl]-thieno[2,3-c]pyridine;
7-Hexyl-4,5,6,7-tetrahydro-6-[2-(4-nitrobenzamido)ethyl]-thieno[2,3-c]pyridine;
7-Hexyl-4,5,6,7-tetrahydro-6-[2-(4-methanesulfonamidobenzamido)ethyl]-thieno[2,3-c]pyridine;
4,5,6,7-Tetrahydro-6-[2-(4-nitrobenzamido)ethyl]-7-phenyl-thieno[2,3-c]pyridine;
4,5,6,7-Tetrahydro-6-[2-(4-methanesulfonamidobenzamido)ethyl]-7-phenylthieno[2,3-c]pyridine;
cis-6-(2-Benzamidoethyl)-4,5,6,7-tetrahydro-5,7-dimethyl-thieno[2,3-c]pyridine;
cis-4,5,6,7-Tetrahydro-5,7-dimethyl-6-[2-(4-nitrobenzamido)ethyl]-thieno[2,3-c]pyridine;
trans-4,5,6,7-Tetrahydro-5,7-dimethyl-6-[2-(4-nitrobenzamido)ethyl]-thieno[2,3-c]pyridine;
cis-4,5,6,7-Tetrahydro-5,7-dimethyl-6-[2-(3-nitrobenzamido)ethyl]-thieno[2,3-c]pyridine;
trans-4,5,6,7-Tetrahydro-5,7-dimethyl-6-[2-(3-nitrobenzamido)ethyl]-thieno[2,3-c]pyridine;
cis-4,5,6,7-Tetrahydro-5,7-dimethyl-6-[2-(2-nitrobenzamido)ethyl]-thieno[2,3-c]pyridine;
cis-6-[2-(4-Chlorobenzamido)ethyl]-4,5,6,7-tetrahydro-5,7-dimethyl-thieno[2,3-c]pyridine;
cis-6-[2-(3-Chlorobenzamido)ethyl]-4,5,6,7-tetrahydro-5,7-dimethyl-thieno[2,3-c]pyridine;
cis-6-[2-(2-chlorobenzamido)ethyl]-4,5,6,7-tetrahydro-5,7-dimethyl-thieno[2,3-c]pyridine;
cis-6-[2-(4-Fluorobenzamido)ethyl]-4,5,6,7-tetrahydro-5,7-dimethyl-thieno[2,3-c]pyridine;
cis-6-[2-(3-Fluorobenzamido)ethyl]-4,5,6,7-tetrahydro-5,7-dimethyl-thieno[2,3-c]pyridine;
cis-6-[2-(2-Fluorobenzamido)ethyl]-4,5,6,7-tetrahydro-5,7-dimethyl-thieno[2,3-c]pyridine;-(3)-methoxybenzamido)ethyl]-5,7-methylthieno[2,3-c]pyridine;
cis-4,5,6,7-Tetrahydro-6-[2-(2-methoxybenzamido)ethyl]-5,7-dimethylthieno[2,3-c]pyridine;
cis-4,5,6,7-Tetrahydro-5,7-dimethyl-6-[2-(4-methylbenzamido)ethyl]2,3-c]pyridine;
cis-6-[2-(4-Trifluoromethylbenzamido)ethyl]-4,5,6,7-tetrahydro-5,7-dimethylthieno[2,3-c]pyridine;
cis-6-[2-(4-Cyanobenzamido)ethyl]-4,5,6,7-tetrahydro-5,7-dimethylthieno[2,3-c]pyridine;
trans-6-[2-(4-Cyanobenzamido)ethyl]-4,5,6,7-tetrahydro-5,7-dimethylthieno[2,3-c]pyridine;
cis-4,5,6,7-Tetrahydro-5,7-dimethyl-6-[2-(4-methylcarboxybenzamido)ethyl]thieno[2,3-c]pyridine;
cis-4,5,6,7-Tetrahydro-5,7-dimethyl-6-[2-(4-sulfonamidobenzamido)ethyl]thieno[2,3-c]pyridine;
cis-6-[2-[4-(N,N-Diethylaminosulfonylbenzamido)ethyl]-4,5,6,7-tetrahydro-5,7-dimethylthieno[2,3-c]pyridine;
cis-4,5,6,7-Tetrahydro-6-[2-(4-methanesulfonylbenzamido)ethyl]-5,7-dimethylthieno[2,3-c]pyridine;
cis-6-[2-(2,4-Difluorobenzamido)ethyl]-4,5,6,7-tetrahydro-5,7-dimethylthieno[2,3-c]pyridine;
cis-6-[2-(3,4-Dichlorobenzamido)ethyl]-4,5,6,7-tetrahydro-5,7-dimethylthieno[2,3-c]pyridine;
cis-6-[2-(2,3,4,5,6-Pentafluorobenzamido)ethyl]-4,5,6,7-tetrahydro-5,7-dimethylthieno[2,3-c]pyridine;
cis-4,5,6,7-Tetrahydro-6-[2-(pyridine-2-carboxamido)ethyl]-5,7-dimethylthieno[2,3-c]pyridine;
cis-4,5,6,7-Tetrahydro-6-[2-(pyridine-3-carboxamido)ethyl]-5,7-dimethylthieno[2,3-c]pyridine;

cis-4,5,6,7-tetrahydro-6-[2-pyridine-4-carboxamidoethyl]-5,7-dimethylthieno[2,3-c]pyridine;
cis-4,5,6,7-Tetrahydro-5,7-dimethyl-6-[2-(2-thiophenecarboxamido)ethyl]thieno[2,3]pyridine;
cis-4,5,6,7-Tetrahydro-5,7-dimethyl-6-[2-(4-nitrothiophene-2-carboxamido)ethyl]thieno[2,3]pyridine;
cis-4,5,6,7-Tetrahydro-5,7-dimethyl-6-[2-[4-[(imidazo-1-yl)methyl]benzamido-ethyl-5,7-dimethylthieno[2,3-c]pyridine;
Diethyl cis-4,5,6,7-Tetrahydro-5,7-dimethyl-6-[2-(4-phosphonomethylbenzamido)ethyl]thieno[2,3]pyridine;
cis-4,5,6,7-Tetrahydro-6-[2-(4-methanesulfonylmethylbenzamido)ethyl]thieno[2,3]pyridine;
cis-4,5,6,7-Tetrahydro-6-[2-[4-(imidazo-1-yl)benzamido]ethyl]-5,7dimethylthieno[2,3]pyridine;
cis-4,5,6,7-Tetrahydro-5,7-dimethyl-6-[2-(4-nitrophenylsulfonamido)ethyl]thieno[2,3]pyridine;
trans-4,5,6,7-Tetrahydro-5,7-dimethyl-6-[2-(4-nitrophenylsulfonamido)ethyl]thieno[2,3]pyridine;
cis-6-[2-(4-Chlorobenzenesulfonamido)ethyl]-4,5,6,7-tetrahydro-5,7-dimethylthieno[2,3-c]pyridine;
cis-4,5,6,7-Tetrahydro-5,7-dimethyl-6-[2-(4-nitrobenzylamino)ethyl]thieno[2,3]pyridine;
cis-4,5,6,7-Tetrahydro-5,7-dimethyl-6-[3-(4-nitrobenzamido)propyl]thieno[2,3]pyridine;
cis-4,5,6,7-Tetrahydro-5,7-dimethyl-6-[3-(4-nitrophenylsulfonamido)propyl]thieno[2,3]pyridine;
cis-4,5,6,7-Tetrahydro-5,7-dimethyl-6-[4-(4-nitrobenzamido)butyl]thieno[2,3]pyridine;
cis-4,5,6,7-Tetrahydro-5,7-dimethyl-6-[3-(4-nitrobenzenesulfonamido)butyl]thieno[2,3]pyridine;
4-(4,5,6,7-Tetrahydrothieno[2,3-c]pyridin-6-yl)-1-(4-nitrobenzoyl)piperidine;
cis-2-Chloro-4,5,6,7-tetrahydro-5,7-dimethyl-6-[3-(4-nitrobenzamido)ethyl]thieno[2,3]pyridine;
cis-2-bromo-4,5,6,7-tetrahydro-5,7-dimethyl-6-[2-nitrobenzamido)ethyl]thieno[2,3-c]pyridine;
cis-4,5,6,7-Tetrahydro-5,7-dimethyl-2-nitro-6-[2-(4-nitrobenzamido)ethyl]thieno[2,3-c]pyridine;
cis-4,5,6,7-Tetrahydro-5,7-dimethyl-N-methyl-6-[2-(4-nitrobenzamido)ethyl]thieno[2,3-c]pyridine;
cis-4,5,6,7-Tetrahydro-5,7-dimethyl-N-(1-methylethyl)-6-[2-(4-nitrobenzamido)ethyl]thieno[2,3-c]pyridine;
cis-4,5,6,7-Tetrahydro-5,7-dimethyl-N-(1-methylethyl)-6-[2-(4-nitrophenylsulfonamido)ethyl]thieno[2,3-c]pyridine;
cis-7-Butyl-4,5,6,7-tetrahydro-5-methyl-6-[2-(4-nitrobenzamido)ethyl]thieno[2,3-c]pyridine;
cis-7-Butyl-4,5,6,7-tetrahydro-5-methyl-6-[2-(2-nitrobenzamido)ethyl]thieno[2,3-c]pyridine;
cis-7-Hexyl-4,5,6,7-tetrahydro-6-[2-(4-nitrobenzamido)ethyl]-5-methylthieno[2,3-c]pyridine;
trans-7-Hexyl-4,5,6,7-tetrahydro-7-methyl-6-[2-(4-nitrobenzamido)ethyl]thieno[2,3-c]pyridine;
cis-4,5,6,7-Tetrahydro-5-methyl-6-[2-(4-nitrobenzamido)ethyl]-7-phenylthieno[2,3-c]pyridine;
trans-4,5,6,7-Tetrahydro-5-methyl-6-[2-(4-nitrobenzamido)ethyl]-7-phenylthieno[2,3-c]pyridine;
cis-4,5,6,7-Tetrahydro-5-methyl-6-[2-(3-nitrobenzamido)ethyl]-7-phenylthieno[2,3-c]pyridine;
cis-4,5,6,7-Tetrahydro-5-methyl-6-[2-(2-nitrobenzamido)ethyl]-7-phenylthieno[2,3-c]pyridine;
cis-4,5,6,7-Tetrahydro-5-methyl-6-[2-(4-nitrophenylsulfonamido)ethyl]-7-phenylthieno[2,3-c]pyridine;
cis-4,5,6,7-Tetrahydro-7-(4-methoxyphenyl)-5-methyl-6-[2-(4-nitrobenzamido)ethyl]thieno[2,3-c]-pyridine;
trans-4,5,6,7-Tetrahydro-7-(4-methoxyphenyl)-5-methyl-6-[2-(4-nitrobenzamido)ethyl]thieno[2,3-c]-pyridine;
cis-7-(4-Chlorophenyl)-4,5,6,7-tetrahydro-5-methyl-6-[2-(4-nitrobenzamido)ethyl]thieno[2,3-c]pyridine;
trans-7-(4-Chlorophenyl)-4,5,6,7-tetrahydro-5-methyl-6-[2-(4-nitrobenzamido)ethyl]thieno[2,3-c]pyridine;
cis-4,5,6,7-Tetrahydro-5-methyl-6-[2-(4-nitrobenzamido)ethyl]-7-(thien-2-yl)thieno[2,3-c]pyridine;
cis-4,5,6,7-tetrahydro-5-methyl-6-[2-(4-nitrobenzenesulfonamido)ethyl]-7-(thien-2-yl)thieno[2,3-c]pyridine;
cis-4,5,6,7-Tetrahydro-7-methyl-6-[2-(4-nitrobenzamido)ethyl]-5-propylthieno[2,3-c]pyridine;
cis-4,5,6,7-Tetrahydro-7-methyl-6-[3-(4-nitrobenzamido)propyl]-5-propylthieno[2,3-c]pyridine;
cis-4,5,6,7-Tetrahydro-7-methyl-6-[3-(4-nitrobenzenesulfonamido)propyl]-5-propylthieno[2,3-c]pyridine;
cis-4,5,6,7-Tetrahydro-4,7-dimethyl-6-[2-(4-nitrobenzamido)ethyl]thieno[2,3-c]pyridine;
trans-4,5,6,7-Tetrahydro-4,7-dimethyl-6-[2-(4-nitrobenzamido)ethyl]thieno[2,3-c]pyridine;
cis-6-[2-(4-Aminobenzamido)ethyl]-4,5,6,7-tetrahydro-5,7-dimethylthieno[2,3-c]pyridine;
cis-6-[2-(2-Aminobenzamido)ethyl]-4,5,6,7-tetrahydro-5,7-dimethylthieno[2,3-c]pyridine;
cis-6-[2-(4-Aminobenzenesulfonamido)ethyl]-4,5,6,7-tetrahydro-5,7-dimethylthieno[2,3-c]pyridine;
cis-6-[2-(2-Aminobenzenesulfonamido)ethyl]-4,5,6,7-tetrahydrothieno[2,3-c]pyridine;
cis-6-[3-(4-Aminophenylsulfonamido)propyl]-4,5,6,7-tetrahydro-5,7-dimethylthieno[2,3-c]pyridine;
cis-6-[2-(4-Aminophenylsulfonamido)ethyl]-4,5,6,7-tetrahydro-5-methyl-7-phenylthieno[2,3-c]pyridine;
cis-6-[2-(4-Aminobenzenesulfonamido)ethyl]-4,5,6,7-tetrahydro-5-methyl-7-(thien-2-yl)thieno[2,3-c]pyridine;
cis-6-[2-(4-Acetylamino)benzamido]ethyl]-4,5,6,7-tetrahydro-5,7-dimethylthieno[2,3-c]pyridine;
cis-6-[2-(2-Acetylamino)benzamido]ethyl]-4,5,6,7-tetrahydro-5,7-dimethylthieno[2,3-c]pyridine;
cis-4,5,6,7-Tetrahydro-5,7-dimethyl-6-[2-(4-trimethylacetylamino)benzamido]ethyl]thieno[2,3-c]pyridine;
cis-6-[2-(4-Acetylamino)benzenesulfonamido]ethyl]-4,5,6,7-tetrahydro-5,7-dimethylthieno[2,3-c]pyridine;
cis-6-[2-(2-Acetamidobenzenesulfonamido)ethyl]-4,5,6,7-tetrahydro-5,7-dimethylthieno[2,3-c]pyridine;
cis-4,5,6,7-Tetrahydro-5,7-dimethyl-6-[2-(4-methanesulfonylaminobenzamido)ethyl]ethyl]thieno[2,3-c]pyridine;
trans-4,5,6,7-tetrahydro-5,7-dimethyl-6-[2-(4-methanesulfonylaminobenzamido)ethyl]thieno[2,3-c]pyridine;
cis-4,5,6,7-Tetrahydro-6-{2-(4-methanesulfonylamino)benzenesulfonamido]ethyl}-5,7-dimethylthieno[2,3-c]pyridine;
cis-4,5,6,7-Tetrahydro-5,7-dimethyl-6-[3-(4-methanesulfonylaminobenzamido)propyl]thieno[2,3-c]pyridine;
cis-4,5,6,7-Tetrahydro-6-[3-(4-methanesulfonamidophenylsulfonamido)propyl]-5,7-dimethylthieno[2,3-c]pyridine;
cis-4,5,6,7-Tetrahydro-6-[4-(4-methanesulfonamidobenzamido)butyl]-5,7-dimethylthieno[2,3-c]pyridine;
cis-4,5,6,7-Tetrahydro-6-[4-(4-methanesulfonamidobenzenesulfonamido)butyl]-5,7-dimethylthieno[2,3-c]pyridine;

4-(4,5,6,7-Tetrahydrothieno[2,3-c]pyridin-6-yl)-1-(4-methanesulfonaminobenzoyl)piperidine;

cis-2-Bromo-4,5,6,7-tetrahydro-6-[2-(4-methanesulfonamidobenzamido)ethyl]-5,7-dimethylthieno[2,3-c]pyridine;

cis-4,5,6,7-Tetrahydro-6-[4-(4-methanesulfonamidobenzenesulfonamido)ethyl]-N-methyl-5,7-dimethylthieno[2,3-c]pyridine;

cis-4,5,6,7-Tetrahydro-6-[4-(4-methanesulfonylamidophenylsulfonamido)ethyl]-5,7-dimethyl-N-(1-methylethyl)thieno[2,3-c]pyridine;

cis-7-Butyl-4,5,6,7-tetrahydro-5-methyl-6-[2-(4-methanesulfonamidobenzamido)ethyl]thieno[2,3-c]pyridine;

cis-4,5,6,7-Tetrahydro-5-methyl-6-[2-(4-methanesulfonamidobenzamido)ethyl]-5,7-phenylthieno[2,3-c]pyridine;

cis-4,5,6,7-Tetrahydro-5-methyl-6-[2-(4-methanesulfonamidobenzenesulfonamido)ethyl]-5,7-phenylthieno[2,3-c]pyridine;

cis-4,5,6,7-Tetrahydro-6-[2-(4-methanesulfonamidobenzenesulfonamido)ethyl]-5,7-methyl-7-(thien-2-yl)thieno[2,3-c]pyridine;

cis-4,5,6,7-Tetrahydro-7-methyl-6-[2-(4-methanesulfonamidobenzamido)ethyl]-5-propylthieno[2,3-c]pyridine;

cis-4,5,6,7-Tetrahydro-6-[3-(4-methanesulfonamidobenzamido)propyl]-7-methyl-5-propylthieno[2,3-c]pyridine;

cis-4,5,6,7-Tetrahydro-6-[2-(4-methanesulfonylamidobenzamido)ethyl]-4,7-dimethylthieno[2,3-c]pyridine;

trans-4,5,6,7-Tetrahydro-6-[2-(4-methanesulfonylamidobenzamido)ethyl]-4,7-dimethylthieno[2,3-c]pyridine;

cis-6-[2-(4-Chloromethanesulfonamidobenzamido)ethyl]-4,5,6,7-tetrahydro-5,7-dimethylthieno[2,3-c]pyridine;

cis-6-[2-(4-ethanesulfonamidobenzamido)ethyl]-4,5,6,7-tetrahydro-5,7-dimethylthieno[2,3-c]pyridine;

cis-6-[2-(4-Butanesulfonamidobenzamido)ethyl]-4,5,6,7-tetrahydro-5,7-dimethylthieno[2,3-c]pyridine;

cis-6-{2-[4-(4-Chlorobenzenesulfonamido)benzamido]ethyl}-4,5,6,7-tetrahydro-5,7-dimethylthieno[2,3-c]pyridine;

cis-4,5,6,7-Tetrahydro-5,7-dimethyl-6-{2-[4-(methanesulfonyl-N-methylamino)benzamido]ethyl}thieno[2,3-c[pyridine;

4,5,6,7-Tetrahydro-5-[2-(4-nitrobenzamido)ethyl]-thieno[3,2-c]pyridine cis-4,5,6,7-Tetrahydro-4,6-dimethyl-5-[2-(4-nitrobenzamido)ethyl]thieno[3,2-c]pyridine;

cis-2-Chloro-4,5,6,7-tetrahydro-4,6-dimethyl-5-[2-(4-nitrobenzamido)ethyl]thieno[3,2-c[pyridine;

cis-2-Bromo-4,5,6,7-tetrahydro-4,6-dimethyl-5-[2-(4-nitrobenzamido)ethyl]thieno[3,2-c]pyridine;

cis-4,5,6,7-Tetrahydro-4,6-dimethyl-2-nitro-5-[2-(4-nitrobenzamido)ethyl]thieno[3,2-c]pyridine;

cis-4,5,6,7-Tetrahydro-5,7-dimethyl-6-[2-(4-methanesulfonamidobenzamido)ethyl]thieno[3,2-c]pyridine;

trans-4,5,6,7-Tetrahydro-5,7-dimethyl-6-[2-(4-methanesulfonamidobenzamido)ethyl]thieno[3,2-c]pyridine;

cis-2-Bromo-4,5,6,7-tetrahydro-5-[2-(4-methanesulfonamidobenzamido)ethyl]-4,6-dimethylthieno[3,2-c]pyridine;

cis-4,5,6,7-Tetrahydro-5-[2-(4-methanesulfonylaminophenoxy)-ethyl]-4,6-dimethylthieno[3,2-c]pyridine;

cis-1-Chloro-4,5,6,7-tetrahydro-4,6-dimethyl-5-[2-(4-nitrobenzamido)ethyl]thieno[3,4-c]pyridine;

trans-1-Chloro-4,5,6,7-tetrahydro-4,6-dimethyl-5-[2-(4-nitrobenzamido)ethyl]thieno[3,4-c[pyridine;

cis-2-Chloro-4,5,6,7-tetrahydro-4,6-dimethyl-5-[2-(4-methanesulfonamidobenzamido)ethyl]thieno[3,4-c[pyridine.

4. A compound according to claim 1 selected from the group consisting of:

4,5,6,7-Tetrahydro-6-[2-(6-nitrobenzamido)ethyl]-thieno[2,3-c]pyridine;

5-Butyl-4,5,6,7-Tetrahydro-6-[2-(4-methanesulfonamidobenzamido)ethyl]thieno[2,3-c]pyridine;

5-butyl-4,5,6,7-tetrahydro-7-[(4-methanesulfonamidobenzenesulfonamido)ethyl]thieno[2,3-c]pyridine;

7-Butyl-4,5,6,7-tetrahydro-6-[3-(4-methanesulfonamidobenzamido)ethyl]thieno[2,3-c]pyridine;

7-Hexyl-4,5,6,7-tetrahydro-6-[2-(4-methanesulfonamidobenzamido)ethyl]-thieno[2,3-c]pyridine;

4,5,6,7-Tetrahydro-6-[2-(4-nitrobenzamido)ethyl]-7-phenyl-thieno[2,3-c]pyridine;

cis-6-(2-Benzamidoethyl)-4,5,6,7-tetrahydro-5,7-dimethyl-thieno[2,3-c]pyridine;

cis-4,5,6,7-Tetrahydro-5,7-dimethyl-6-[2-(4-nitrobenzamido)ethyl]-thieno[2,3-c]pyridine;

trans-4,5,6,7-Tetrahydro-5,7-dimethyl-6-[2-(4-nitrobenzamido)ethyl]-thieno[2,3-c]pyridine;

cis-4,5,6,7-Tetrahydro-5,7-dimethyl-6-[2-(2-nitrobenzamido)ethyl]-thieno[2,3-c]pyridine;

cis-6-[2-(4-Chlorobenzamido)ethyl]-4,5,6,7-tetrahydro-5,7-dimethylthieno[2,3-c]pyridine;

cis-4,5,6,7-Tetrahydro-6-[2-(4-methoxybenzamido)ethyl]-5,7-dimethylthieno[2,3-c]pyridine;

cis-4,5,6,7-Tetrahydro-5,7-dimethyl-6-[2-(4-methylbenzamido)ethyl]thieno[2,3-c]pyridine;

cis-6-[2-(4-Cyanobenzamido)ethyl]-4,5,6,7-tetrahydro-5,7-dimethylthieno[2,3-c]pyridine;

trans-6-[2-(4-Cyanobenzamido)ethyl]-4,5,6,7-tetrahydro-5,7-dimethylthieno[2,3-c]pyridine;

cis-6-[2-(2,4-Difluorobenzamido)ethyl]-4,5,6,7-tetrahydro-5,7-dimethylthieno[2,3-c]pyridine;

cis-4,5,6,7-Tetrahydro-5,7-dimethyl-6-[2-(4-nitrophenylsulfonamido)ethyl]thieno[2,3-c]pyridine;

cis-4,5,6,7-Tetrahydro-5,7-dimethyl-6-[2-(4-nitrobenzylamino)ethyl]thieno[2,3-c]pyridine;

cis-4,5,6,7-Tetrahydro-5,7-dimethyl-6-[3-(4-nitrobenzamido)propyl]thieno[2,3]pyridine;

cis-4,5,6,7-Tetrahydro-5,7-dimethyl-6-[3-(4-nitrophenylsulfonamido)propyl]thieno[2,3-c]pyridine;

cis-4,5,6,7-tetrahydro-5,7-dimethyl-6-[4-(4-nitrobenzamido)butyl]thieno[2,3-c]pyridine;

cis-4,5,6,7-Tetrahydro-5,7-dimethyl-6-[4-(4-nitrobenzenesulfonamido)butyl]thieno[2,3-c]pyridine;

4-(4,5,6,7-Tetrahydrothieno[2,3-c]pyridin-6-yl)-1-(4-nitrobenzoyl)piperidine;

cis-2-Bromo-4,5,6,7-tetrahydro-5,7-dimethyl-6-[2-(4-nitrobenzamido)ethyl]thieno[3,2-c]pyridine;

cis-4,5,6,7-Tetrahydro-5,7-dimethyl-6-[2-(4-nitrobenzylamino)ethyl]thieno[2,3]pyridine;

cis-4,5,6,7-Tetrahydro-5,7-dimethyl-N-methyl-6-[2-(4-nitrobenzamido)ethyl]thieno[2,3]pyridine;

cis-7-Butyl-4,5,6,7-tetrahydro-5-methyl-6-[2-(4-nitrobenzamido)ethyl]thieno[2,3-c]pyridine;

cis-4,5,6,7-Tetrahydro-5-methyl-6-[2-(4-nitrobenzamido)ethyl]-7-phenylthieno[2,3]pyridine;

cis-4,5,6,7-Tetrahydro-7-methyl-6-[2-(4-nitrobenzamido)ethyl]-5-propylthieno[2,3]pyridine;

cis-4,5,6,7-Tetrahydro-7-methyl-6-[3-(4-nitrobenzenesulfonamido)propyl]-5-propylthieno[2,3]pyridine;
cis-6-[3-(4-Aminophenylsulfonamido)propyl]-4,5,6,7-tetrahydro-5,7-dimethylthieno[2,3-c]pyridine;
cis-4,5,6,7-Tetrahydro-5,7-dimethyl-6-[2-(4-methanesulfonylaminobenzamido)ethyl]thieno[2,3]pyridine;
trans-4,5,6,7-Tetrahydro-5,7-dimethyl-6-[2-(4-methanesulfonylaminobenzamido)ethyl]thieno[2,3-c]pyridine;
cis-4,5,6,7-Tetrahydro-6-{2-(4-methanesulfonylamino)-benzenesulfonamido]ethyl}-5,7-dimethylthieno[2,3-c]pyridine;
cis-4,5,6,7-Tetrahydro-5,7-dimethyl-6-[3-(4-methansulfonylaminobenzamido)propyl]thieno[2,3-c]pyridine;
cis-4,5,6,7-Tetrahydro-6-[4-(4-methanesulfonylamidobenzamido)butyl]-5,7-dimethylthieno[2,3-c]pyridine;
cis-4,5,6,7-Tetrahydro-6-[4-(4-methanesulfonamidobenzenesulfonamido)butyl]-5,7-dimethylthieno[2,3-c]pyridine;
4-(4,5,6,7-Tetrahydrothieno[2,3-c]pyridin-6-yl)-1-(4-methanesulfonylaminobenzoyl)piperidine;
cis-4,5,6,7-Tetrahydro-6-[2-(4-methanesulfonamidobenzamido)ethyl]-N-methyl-5,7-dimethylthieno[2,3-c]pyridine;
cis-4,5,6,7-tetrahydro-6-[2-(4-methane-sulfonamidophenylsulfonamido)ethyl]-5,7-dimethyl-N-(1-methylethyl)thieno[2,3-c]pyridine;
cis-7-Butyl-4,5,6,7-tetrahydro-5-methyl-6-[2-(4-methanesulfonamidobenzamido)ethyl]thieno[2,3-c]pyridine;
cis-4,5,6,7-Tetrahydro-7-methyl-6-[2-(4-methanesulfonamidobenzamido)ethyl]-5-propylthieno[2,3-c]pyridine;
cis-4,5,6,7-Tetrahydro-6-[3-(4-methanesulfonamidobenzamido)propyl]-7-methyl-5-propylthieno[2,3-c]pyridine;
cis-4,5,6,7-Tetrahydro-4,6-dimethyl-5-[2-(4-nitrobenzamido)ethyl]-thieno[3,2-c]pyridine;
cis-2-Chloro-4,5,6,7-tetrahydro-4,6-dimethyl-5-[2-(4-nitrobenzamido)ethyl]thieno[3,2-c[pyridine;
cis-4,5,6,7-Tetrahydro-4,6-dimethyl-2-nitro-5-[2-(4-nitrobenzamido)ethyl]thieno[3,2-c]pyridine;
cis-4,5,6,7-Tetrahydro-5,7-dimethyl-6-[2-(4-methanesulfonamidobenzamido)ethyl]thieno[3,2]pyridine;
cis-2-Bromo-4,5,6,7-tetrahydro-5-[2-(4-methanesulfonamidobenzamido)ethyl]-4,6-dimethylthieno[3,2-c]pyridine;
cis-4,5,6,7-Tetrahydro-5-[2-(4-methanesulfonylaminophenoxy)-ethyl]-4,6-dimethylthieno[3,2-c]pyridine;
cis-1-Chloro-4,5,6,7-tetrahydro-4,6-dimethyl-5-[2-(4-nitrobenzamido)ethyl]thieno[3,4-c]pyridine; and
trans-1-Chloro-4,5,6,7-tetrahydro-4,6-dimethyl-5-[2-(4-nitrobenzamido)ethyl]thieno[3,4-c]pyridine.

5. The compound according to claim 1 selected from the group consisting of:
cis-4,5,6,7-Tetrahydro-5,7-dimethyl-6-[3-(4-nitrobenzamido)propyl]thieno[2,3]pyridine;
cis-4,5,6,7-Tetrahydro-6-{2-[4-(methanesulfonylamino)-benzenesulfonamido)]ethyl}-5,7-dimethylthieno[2,3-c]pyridine;
cis-7-Butyl-4,5,6,7-tetrahydro-5-methyl-6-[2-(4-methanesulfonamidobenzamido)ethyl]thieno[2,3-c]pyridine; and
cis-4,5,6,7-Tetrahydro-7-methyl-6-[2-(4-methanesulfonamidobenzamido)ethyl]-5-propylthieno[2,3-c]pyridine.

6. A compound of the following formula:

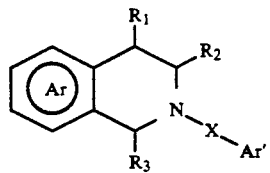

where
Ar' is selected from the group consisting of pyridine, thiophene, furan, pyrrole or

;

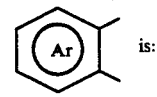 is:

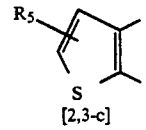

[2,3-c]

$R_1$ is hydrogen or $C_1$–$C_3$ alkyl;
$R_2$ is hydrogen, $C_1$–$C_6$ alkyl, $C_3$–$C_7$ branched chain alkyl;
$R_3$ is hydrogen, $C_1$–$C_6$ alkyl, $C_3$–$C_7$ branched chain alkyl, aryl or substituted aryl wherein the aryl substituents are $C_1$–$C_6$ alkyl or $C_1$–$C_6$ alkoxy;
$R_4$ is hydrogen, $C_1$–$C_5$ alkyl, $C_3$–$C_7$ branched chain alkyl, halogen, $C_1$–$C_3$ alkoxy, nitro, amino, imidazole, cyano, $CO_2R_1$, $SO_2R_1$, $CF_3$, $NHCOR_8$, $NR_7SO_2R_8$, $CH_2SO_2R_1$, $CH_2PO(OR_1)_2$ or $CH_2$-imidazole;
X is $(CH_2)_mNR_7CO$, $(CH_2)_mNR_7SO_2$ or $(CH_2)_mNHCH_2$;

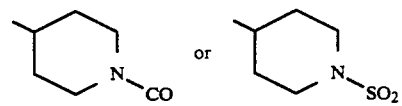

$R_5$ is hydrogen, halogen or nitro;
$R_7$ is hydrogen or $C_1$–$C_3$ alkyl;
$R_8$ is hydrogen, $CF_3$, $C_1$–$C_4$alkyl, $C_3$–$C_5$ branched chain alkyl, aryl or substituted aryl;
m is 2–4; and
when $R_1$ is alkyl and $R_2$ is hydrogen and when $R_1/R_3$ or $R_2/R_3$ are both alkyl; $R_1/R_3$ is cis or trans and $R_2/R_3$ is cis or trans,

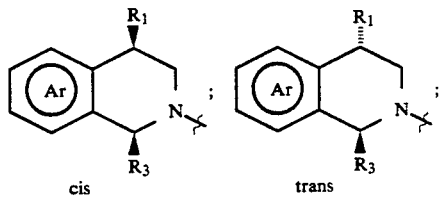

cis    trans

-continued

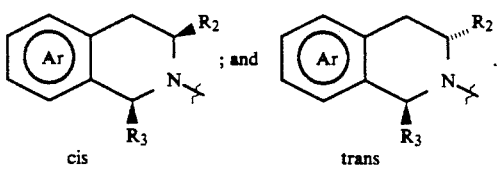

7. The compound according to claim 1 wherein:
$R_1$ is hydrogen or methyl;
$R_2$ is hydrogen or $C_1$-$C_4$ alkyl;
$R_3$ is hydrogen, $C_1$-$C_6$ alkyl, branched propyl, phenyl, thiophene or 4-methoxy-phenyl;
$R_4$ is hydrogen, chloro, fluoro, methyl, methoxy, nitro, amino, cyano, $NHCOCH_3$, $NHSO_2CH_3$ or $CO_2CH_3$;
$R_5$ may be hydrogen, halogen or nitro;
$R_7$ is hydrogen, methyl or ethyl;
$R_8$ is phenyl or substituted phenyl;
X is $(CH_2)_mNR_7CO$, $(CH_2)_mNR_7SO_2$ or $(CH_2)_mNHCH_2$; and
$R_5$ is hydrogen, halogen or nitro; and
m is 2 or 3.

8. A compound of the following formula:

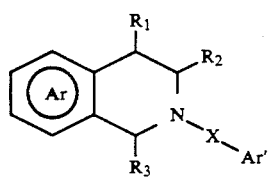

where
Ar' is selected from the group consisting of pyridine, thiophene, furan, pyrrole or

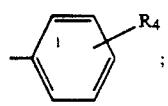

  is:

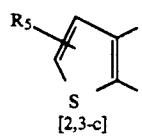
[2,3-c]

$R_1$ is hydrogen or $C_1$-$C_3$ alkyl;
$R_2$ is hydrogen, $C_1$-$C_6$ alkyl, $C_3$-$C_7$ branched chain alkyl;
$R_3$ is hydrogen, $C_1$-$C_6$ alkyl, $C_3$-$C_7$ branched chain alkyl, aryl or substituted aryl wherein the aryl substituents are $C_1$-$C_6$ alkyl or $C_1$-$C_6$ alkoxy;
$R_4$ is hydrogen, $C_1$-$C_5$ alkyl, $C_3$-$C_7$ branched chain alkyl, halogen, $C_1$-$C_3$ alkoxy, nitro, amino, imidazole, cyano, $CO_2R_1$, $SO_2R_1$, $CF_3$, $NHCOR_8$, $NR_7SO_2R_8$, $CH_2SO_2R_1$, $CH_2PO(OR_1)_2$ or $CH_2$-imidazole;
X is $CH_2$, $(CH_2)_n$, $(CH_2)_nO$, $(CH_2)_mNR_7CO$, $(CH_2)_mNR_7SO_2$, $(CH_2)_mNHCH_2$,

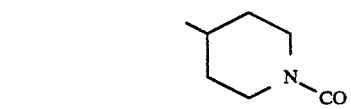

or

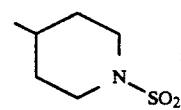  ;

n is 2-5;
$R_5$ is hydrogen, halogen or nitro;
$R_7$ is hydrogen or $C_1$-$C_3$ alkyl;
$R_8$ is hydrogen, $CF_3$, $C_1$-$C_4$alkyl, $C_3$-$C_5$ branched chain alkyl, aryl or substituted aryl;
m is 2-4; and,
when $R_1$ is alkyl and $R_2$ is hydrogen and when $R_1/R_3$ or $R_2/R_3$ are both alkyl; $R_1/R_3$ is cis or trans and $R_2/R_3$ is cis or trans,

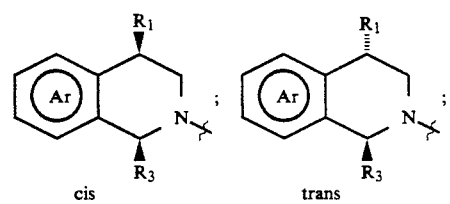

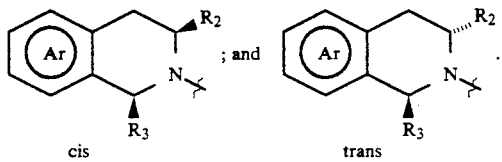

9. The compound according to claim 8 wherein:
$R_1$ is hydrogen or methyl;
$R_2$ is hydrogen or $C_1$-$C_4$ alkyl;
$R_3$ is hydrogen, $C_1$-$C_6$ alkyl, branched propyl, phenyl, thiophene or 4-methoxy-phenyl;
$R_4$ is hydrogen, chloro, fluoro, methyl, methoxy, nitro, amino, cyano, $NHCOCH_3$, $NHSO_2CH_3$ or $CO_2CH_3$;
$R_5$ may be hydrogen, halogen or nitro;
$R_7$ is hydrogen, methyl or ethyl;
$R_8$ is phenyl or substituted phenyl;
X is $(CH_2)_n$, $(CH_2)_2O$, $(CH_2)_mNR_7CO$, $(CH_2)_mNR_7SO_2$ or $(CH_2)_mNHCH_2$;
n is 2-4; and
m is 2 or 3.

10. The compound:
cis-7-Butyl-4,5,6,7-tetrahydro-5-methyl-6-[2-(4-methanesulfonamidobenzamido)ethyl]thieno[2,3-c]pyridine and the intermediates 2-[3-(cis-4,5,6,7-tetrahydro-5,7-dimethylthieno[2,3-c]pyridin-6-yl)propyl]-1H-isoindole-1,3-dione and 2-[4-(cis-4,5,6,7-tetrahydro-5,7-dimethylthieno[2,3-c]pyridine-6-yl)butyl]-1H-isoindole-1,3-dione.

11. An antiarrhythmic agent comprising one or more compounds according to claim 1 and a pharmaceutically inert carrier.

12. An antiarrhythmic agent comprising one or more compounds according to claim 2 and a pharmaceutically inert carrier.

13. An antiarrhythmic agent comprising one or more compounds according to claim 3 and a pharmaceutically inert carrier.

14. A method of increasing the effective refractory period in a mammal comprising administering to a mammal an amount of a compound according to claim 1 which is effective to increase said effective refractory period.

15. A method of increasing the effective refractory period in a mammal comprising administering to a mammal an amount of a compound according to claim 2 which is effective to increase said effective refractory period.

16. A method of increasing the effective refractory period in a mammal comprising administering to a mammal an amount of a compound according to claim 3 which is effective to increase said effective refractory period.

17. A pharmaceutical composition comprising one or more compounds of claim 1 and a pharmaceutically inert carrier.

* * * * *